(12) United States Patent
Packard et al.

(10) Patent No.: US 6,893,868 B2
(45) Date of Patent: May 17, 2005

(54) HOMO-DOUBLY LABELED COMPOSITIONS FOR THE DETECTION OF ENZYME ACTIVITY IN BIOLOGICAL SAMPLES

(75) Inventors: Beverly Packard, Rockville, MD (US); Akira Komoriya, Rockville, MD (US)

(73) Assignee: Onco Immunin, Inc., Gaithersburg, MD (US)

( * ) Notice: Subject to any disclaimer, the term of this patent is extended or adjusted under 35 U.S.C. 154(b) by 0 days.

(21) Appl. No.: 09/747,287

(22) Filed: Dec. 22, 2000

(65) Prior Publication Data

US 2003/0207264 A1 Nov. 6, 2003

Related U.S. Application Data

(63) Continuation-in-part of application No. 09/394,019, filed on Sep. 10, 1999, which is a continuation-in-part of application No. 08/802,981, filed on Feb. 20, 1997, now Pat. No. 6,037,137, application No. 09/747,287, which is a continuation-in-part of application No. PCT/US00/24882, filed on Sep. 11, 2000, which is a continuation-in-part of application No. 09/394,019, which is a continuation-in-part of application No. 08/802,981, filed on Feb. 20, 1997.

(51) Int. Cl.$^7$ ............................. C12N 5/00; C12Q 1/37; A61K 38/00
(52) U.S. Cl. ........................ 435/325; 435/23; 435/7.72; 436/172; 514/2; 530/300
(58) Field of Search ........................ 435/325, 23, 7.72; 530/300; 514/2; 436/172; 536/172

(56) References Cited

U.S. PATENT DOCUMENTS

| | | | |
|---|---|---|---|
| 4,557,862 A | 12/1985 | Mangel et al. |
| 4,648,893 A | 3/1987 | Roux |
| 4,708,929 A | 11/1987 | Henderson |
| 4,780,421 A | 10/1988 | Kameda et al. |
| 4,897,444 A | 1/1990 | Brynes et al. |
| 5,011,910 A | 4/1991 | Marshall et al. |
| 5,110,801 A | 5/1992 | Leveen et al. |
| 5,118,801 A | 6/1992 | Lizardi et al. |
| 5,212,298 A | 5/1993 | Rademacher et al. |
| 5,312,728 A | 5/1994 | Lizardi et al. |
| 5,506,115 A | 4/1996 | Toth et al. |
| 5,539,082 A | 7/1996 | Nielsen et al. |
| 5,605,809 A | 2/1997 | Komoriya et al. |
| 5,652,107 A | 7/1997 | Lizardi et al. |
| 5,698,411 A | 12/1997 | Lucas et al. |
| 5,714,342 A | 2/1998 | Komoriya et al. |
| 5,723,288 A | 3/1998 | Dykstra et al. |
| 5,759,773 A | 6/1998 | Tyagi et al. |
| 5,776,720 A | 7/1998 | Jaffe et al. |
| 5,804,395 A | 9/1998 | Schade et al. |
| 5,807,674 A | 9/1998 | Tyagi et al. |
| 5,912,137 A | 6/1999 | Tsien et al. |
| 5,925,517 A | 7/1999 | Tyagi et al. |
| 5,925,558 A | 7/1999 | Tsien et al. |
| 5,998,204 A | 12/1999 | Tsien et al. |
| 6,037,130 A | 3/2000 | Tyagi et al. |
| 6,037,137 A | 3/2000 | Komoriya et al. |
| 6,103,476 A | 8/2000 | Tyagi et al. |
| 6,150,097 A | 11/2000 | Tyagi et al. |
| 6,410,255 B1 | 6/2002 | Pollok et al. |

FOREIGN PATENT DOCUMENTS

| WO | WO 96/13607 | 5/1996 |
|---|---|---|
| WO | WO 97/39008 A1 | 10/1997 |
| WO | WO 98/10096 | 3/1998 |
| WO | WO 98/37226 A1 | 8/1998 |
| WO | WO 00/06778 A1 | 2/2000 |
| WO | WO 00/71562 A1 | 11/2000 |
| WO | WO 00/71740 A1 | 11/2000 |
| WO | WO 01/18238 A1 | 3/2001 |
| WO | WO 01/31062 A1 | 5/2001 |

OTHER PUBLICATIONS

Packard et al., Proc. Natl. Acad. Sci. 93, 11640–11645, Oct. 1996.*
Knight et al. "A novel coumarin–labelled peptide for sensitive continuous assats of the matrix metalloproteinases." *FEBBS Letters* 296(3):263–266 (1992).
Carmel et al. "Use of Substrates with Fluorescent Donor and Acceptor Chromophores for the Kinetic Assay of Hydrolases." *FEBBS Letters* 30(1):11–14 (1973).
Isaac et al. "Use of Flurescence Resonance Energy Transfer to Estimate Intramolecular Distances in the Msx–1 Homeodomain." *Biochemistry* 34(1):15276–15281 (1995).
Keller et al. "Mode of Insertion of the Signal Sequence of a Bacterial Precusor Protein into Phospholipid Bilayers As Revealed by Cysteine–Based Site Directed Spectroscopy." *Biochemistry* 35:3063–3071 (1996).
Latt et al. "Flourescence Determination of Carboxypeptidase A Activity Based on Electronic Energy Transfer," *Analytical Biochemistry* 50:56 (1972).
Matayoshi et al. "Novel Fluorogenic Substrates for Assaying Retroviral Proteases by Resonance Energy Transfer." *Science* 247 (1990) p 954–958.
Matsuzaki et al. "Translocation of a Channel–Forming Antimicrobial Peptide, Maganin 2, across Lipid Bilayers by Forming a Pore." *Biochemistry* 34:6521–6526 (1995).

(Continued)

*Primary Examiner*—Jon Weber
*Assistant Examiner*—Chih-Min Kam
(74) *Attorney, Agent, or Firm*—Quine I.P. Law Group. P.C.

(57) ABSTRACT

The present invention provides for novel reagents whose fluorescence changes upon cleavage or a change in conformation of a backbone. The reagents comprise a backbone (e.g. nucleic acid, polypeptide, etc.) joining two fluorophores of the same species whereby the fluorophores form an H-dimer resulting in quenching of the fluorescence of the fluorophores. When the backbone is cleaved or changes conformation, the fluorophores are separated, no longer forming an H-type dimer, and are de-quenched thereby providing a detectable signal. The use of a single fluorophore rather than an "acceptor-donor" fluoresecence resonance energy transfer system offers synthesis and performance advantages.

18 Claims, 10 Drawing Sheets-

OTHER PUBLICATIONS

Nagase et al. "Design and Characterization of a Fluorogenic Substrate Selectively Hydrolyzed by Stromelysin 1 (Matrix Metalloproteinase–3)" *J. of Biol. Chem* 269:20952 (1994).

Packard et al. Intramolecular Excitonic Dimers in Protease Substrated: Modfication of the Backbone Moiety to Probe the H–Dimer Structure. J. Phys. Chem. B 1820–1827 (1998).

Parkhurst et al. "Donor–Accoptor Distance Distributions in a Double–Labeled Fluorescent Oligonucleotide Both as a Single Strand and in Duplexes." *Biochemistry* 34(1):293–300 (1995).

Parkhurst et al. Kinetic Studies by Fluorescence Resonance Energy Transfer Employing a Double–Labeked Oligonucleotide: Hybridization to the Oligonucleotide Complement and to Single Strand DNA *Biochemistry* 34:285–292 (1995).

Wang et al. "Design and Synthesis of New Flourogenic HIV Protease Substrates Based on Resonance Energy Transfer." *Tetrahedron Letters* 31:6493 (1990).

Wu et al. "Resonance Energy Transfer: Methods and Applications." *Analytical Biochemistry* 218:1–13 (1994).

Yang et al. "Conformational Flexibality of Three–Way DNA Junctions Containing Inpaired Nucleotides." *Biochemistry* 35:7959–7967 (1996).

Ekert et al. *EMBO J.* 18(2):330–338 (1999).

Finucane et al. Abstract *J. Biol. Chem* 274(4):2225–2233 (1999).

Harvey et al. *Jol. Of Cell Biol.* 148(1) (2000), pp. 57–92.

Hirata et al. *J. of Exp Med.* 187(4) (1998), pp. 587–600.

Kanuka et al. *PNAS USA* 96:145–150 (1999).

Komoriya et al. *J. of Exp. Mel* 191(11):1819–1829 (2000).

Packard et al. *Biophysical Chemistry* 67 167–176 (1997).

Packard et al. *J. Phys. Chem B*, 101:5070–5074 (1997).

Packard et al. *J. Phys. Chem B* 752–758 (1998).

Packard et al. *J. Phys. Chem. B* 1820–1827 (1998).

Packard et al. *Methods in Enzymology* 278:15–23 (1997).

Perez et al. *Molecular Human Reproduction* 5(5):414–420 (1999).

Robles et al. *Endocrinology* (1999) ABSTRACT, vol 140, No 6, p 2641–2644.

Zapata et al. *Jol. Of Biol Chem.* 273(12):6916–6920 (1998).

\* cited by examiner

US 6,893,868 B2

HOMO-DOUBLY LABELED COMPOSITIONS FOR THE DETECTION OF ENZYME ACTIVITY IN BIOLOGICAL SAMPLES

CROSS-REFERENCE TO RELATED APPLICATIONS

This is a continuation-in-part of U.S. Ser. No. 09/394,019; filed on Sep. 10, 1999, which is a continuation-in-part of U.S. Ser. No. 08/802,981, filed on Feb. 20, 1997, now U.S. Pat. No. 6,037,137. This is also a continuation-in-part of PCT/US00/24882, filed on Sep. 11, 2000 designating the United States, which is a continuation-in-part of U.S. Ser. No. 09/394,019, filed on Sep. 10, 1999, which is a continuation-in-part of U.S. Ser. No. 08/802,981, filed on Feb. 20, 1997, now U. S. Pat. 6,037,137. All of these documents are herein incorporated by reference in their entirety for all purposes.

FIELD OF THE INVENTION

This invention pertains to a class of novel fluorogenic compositions whose fluorescence level increases in the presence active proteases. These fluorogenic protease indicators typically fluoresce at visible wavelengths and are thus highly useful for the detection and localization of protease activity in biological samples.

BACKGROUND OF THE INVENTION

Proteases represent a number of families of hydrolytic enzymes that catalytically hydrolyze peptide bonds. Principal groups of proteases include metalloproteases, serine proteases, cysteine proteases and aspartic proteases. Proteases, in particular serine proteases, are involved in a number of physiological processes such as blood coagulation, fertilization, inflammation, hormone production, the immune response and fibrinolysis.

Numerous disease states are caused by and can be characterized by alterations in the activity of specific proteases and their inhibitors. For example emphysema, arthritis, thrombosis, cancer metastasis and some forms of hemophilia result from the lack of regulation of serine protease activities (see, for example, *Textbook of Biochemistry with Clinical Correlations*, John Wiley and Sons, Inc. N.Y. (1993)). In case of viral infection, the presence of viral proteases have been identified in infected cells. Such viral proteases include, for example, HIV protease associated with AIDS and NS3 protease associated with Hepatitis C. These viral proteases play a critical role in the virus life cycle.

Proteases have also been implicated in cancer metastasis. Increased synthesis of the protease urokinase has been correlated with an increased ability to metastasize in many cancers. Urokinase activates plasmin from plasminogen which is ubiquitously located in the extracellular space and its activation can cause the degradation of the proteins in the extracellular matrix through which the metastasizing tumor cells invade. Plasmin can also activate the collagenases thus promoting the degradation of the collagen in the basement membrane surrounding the capillaries and lymph system thereby allowing tumor cells to invade into the target tissues (Dano, et al. (1985) *Adv. Cancer. Res.*, 44: 139.

Clearly measurement of changes in the activity of specific proteases is clinically significant in the treatment and management of the underlying disease states. Proteases, however, are not easy to assay. Typical approaches include ELISA using antibodies that bind the protease or RIA using various labeled substrates. With their natural substrates assays are difficult to perform and expensive. With currently available synthetic substrates the assays are expensive, insensitive and nonselective. In addition, many "indicator" substrates require high quantities of protease which results, in part, in the self destruction of the protease.

Recent approaches to protease detection rely on a cleavage-induced spectroscopic change in a departing chromogen or fluorogen located in the P1' position (the amino acid position on the carboxyl side of the cleavable peptide bond) (see, for example U.S. Pat. Nos. 4,557,862 and 4,648,893). However, many proteases require two or four amino acid residues on either side of the scissile bond for recognition of the protease (a specific protease may require up to 6 amino acid residues) and thus, these approaches lack protease specificity.

Recently however, fluorogenic indicator compositions have been developed in which a "donor" fluorophore is joined to an "acceptor" chromophore by a short bridge containing a (7 amino acid) peptide that is the binding site for an HIV protease and linkers joining the fluorophore and chromophore to the peptide (Wang et al. (1990) *Tetra. Letts.* 45: 6493–6496). The signal of the donor fluorophore was quenched by the acceptor chromophore through a process believed to involve resonance energy transfer (RET). Cleavage of the peptide resulted in separation of the chromophore and fluorophore, removal of the quench and a subsequent signal was measured from the donor fluorophore.

The design of the bridge between the donor and the acceptor led to relatively inefficient quenching limiting the sensitivity of the assay. In addition, the chromophore and/or fluorophore absorbed light in the ultraviolet range reducing the sensitivity for detection in biological samples which typically contain molecules that absorb strongly in the ultraviolet. Broad utility of these substrates was also limited by the modifications to existing equipment required for optimal measurements.

Clearly fluorogenic protease indicators that show a high signal level when cleaved, and a very low signal level when intact, that show a high degree of protease specificity, and that operate exclusively in the visible range thereby rendering them suitable for use in biological samples are desirable. The compositions of the present invention provide these and other benefits.

SUMMARY OF THE INVENTION

The present invention provides for novel reagents whose fluorescence increases in the presence of particular proteases. These fluorogenic protease indicators provide a high intensity fluorescent signal at a visible wavelength when they are digested by a protease. Because of their high fluorescence signal in the visible wavelengths, these protease indicators are particularly well suited for detection of protease activity in biological samples, in particular, in frozen tissue section and cultured or freshly isolated cells. The measurement can be carried out, e.g., using a fluorescence microscope for histological samples, cells, and the like and using a flow cytometer or microscope for cell suspensions and adherent cell cultures. Hence, the fluorogenic compositions of this invention allow detection of intracellular protease activity.

The fluorogenic protease indicators of the present invention are compositions suitable for detection of the activity of a protease. These compositions have the general formula:

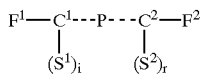

$$\text{I}$$

in which P is a peptide comprising a protease binding site for said protease consisting of 2 to about 15, preferably 2 to about 12, preferably 2 to about 10, preferably 2 to about 8, 2 to about 6, or 2 to about 4 amino acids; $F^1$ and $F^2$ are fluorophores; $S^1$ and $S^2$ are peptide spacers ranging in length from 1 to about 50 amino acids; i and r are independently 0 or 1; and $C^1$ and $C^2$ are conformation determining regions comprising peptides ranging in length from 1 to about 8, amino acids, more preferably from 1 to about 6 amino acids. The conformation determining regions each introduce a bend into the composition or otherwise restrict the degrees of freedom of the peptide backbone, thereby juxtaposing the fluorophores with a separation of less than about 100 Å. When either of the spacers ($S^1$ and $S^2$) are present they are linked to the protease binding site by a peptide bond to the alpha carbon of the terminal amino acid. Thus, when i is 1, $S^1$ is joined to $C^1$ by a peptide bond through a terminal α-amino group of $C^1$, and when r is 1, $S^2$ is joined to $C^2$ by a peptide bond through a terminal alpha carboxyl group of $C^2$.

The amino acid residues comprising a protease binding site are, by convention, numbered relative to the peptide bond hydrolyzed by a particular protease. Thus the first amino acid residue on the amino side of the cleaved peptide bond is designated $P_1$ while the first amino acid residue on the carboxyl side of the cleaved peptide bond is designated $P_1'$. The numbering of the residues increases with distance away from the hydrolyzed peptide bond. Thus a four amino acid protease binding region would contain amino acids designated:

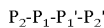

and the protease would cleave the binding region between $P_1$ and $P_1'$.

In particularly preferred embodiments, the fluorogenic compositions of this invention are compositions of Formula II and Formula V as described herein. Preferred fluorogenic indicators according to this invention have conformation determining regions and, optionally, spacers as described herein. In a most preferred embodiment, the compositions bear a single species of fluorophore. Fluorophores suitable for these "homolabeled" compositions include fluorophores that form H-type dimers. It was a surprising discovery of this invention that a single species of fluorophore is capable of "self-quenching" when it participates in the formation of an H-type dimer. Such self-quenching dimer formation is not limited to a particular backbone, but may be accomplished in a wide variety of configurations and thus the principle can be applied in many contexts. Thus, in one embodiment, this invention provides a fluorogenic composition comprising a polypeptide backbone or a nucleic acid backbone joining two fluorophores of the same species where the fluorophores form an H-dimer resulting in quenching of fluorescence of the fluorophores. Preferred polypeptide backbones range comprise a protease binding site ranging in length from about 2 to about 8, more preferably from about 2 to about 15 amino acids and certain polypeptide backbones range in length from about 4 to about 31 amino acids.

Similarly, preferred nucleic acid backbones range in length from about 10 to about 100 nucleotides, more preferably from about 15 to about 50 nucleotides. Certain preferred nucleic acid backbones comprise a restriction site.

In certain embodiments, the fluorogenic compositions are attached to a solid support, while in other embodiments, the fluorogenic compositions are inside a cell (e.g. a mammalian cell, an insect cell, a yeast cell, etc.). The fluorogenic compositions can also bear one or more hydrophobic groups (e.g. Fmoc, 9-fluoreneacetyl group, 1-fluorenecarboxylic group, 9-florenecarboxylic group, and 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4'-dimethoxybenzhydryl (Mbh),Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), Benzyloxymethyl (Bom), t-butoxycarbonyl (Boc), cyclohexyloxy (cHxO),t-butoxymethyl (Bum), t-butoxy (tBuO), t-Butyl (tBu), Acetyl (Ac), and Trifluoroacetyl (TFA), etc.). In certain particularly preferred embodiments, the hydrophobic group is attached to a terminus of the backbone (e.g. the carboxyl or amino terminus of a polypeptide backbone).

Particularly preferred fluorophores used in the compositions of this invention have an excitation wavelength between about 300 and 800 nm, more preferably between about 310 nm and about 750 nm, most preferably between about 315 nm and about 700 nm. In certain preferred embodiments, the fluorophores include, but are not limited to, carboxytetramethylrhodamine, carboxyrhodamine-X, carboxyrhodamine 110, diethylaminocoumarin, and carbocyanine dyes.

In still another embodiment, this invention provides a cell (e.g. mammalian cell, insect cell, yeast cell, etc.) comprising one or more of the fluorogenic indicators of this invention (e.g. as described above).

This invention also provides a method of detecting the activity of a protease. The method typically involves contacting the protease with a fluorogenic composition comprising a polypeptide backbone joining two fluorophores of the same species whereby the fluorophores form an H-dimer resulting in quenching of the fluorescence of said fluorophores (e.g. a peptide-backbone fluorogenic composition as described above); and detecting a change in fluorescence or absorbance of said fluorogenic composition where an increase in fluorescence or a change in absorbance indicates that the protease cleaves the polypeptide backbone. In certain preferred embodiments, the fluorogenic composition is attached to a solid support and/or is inside a cell (e.g. a mammalian cell). In certain embodiments, the contacting is in a histological section, a cell culture, a seeded or cultured adherent cell, or a cell suspension derived from a biological sample (e.g tissue, blood, urine, saliva, lymph, biopsy). Detection is by any of a number of methods known to those of skill in the art. Such methods include, but are not limited to fluorescence microscopy, confocal microscopy, fluorescence microplate reader, flow cytometry, fluorometry, and absorption spectroscopy.

In still another embodiment, this invention provides a method of detecting the activity of a nuclease or the presence of a nucleic acid. The method involves contacting the nuclease or the nucleic acid with a fluorogenic composition comprising a nucleic acid backbone joining two fluorophores of the same species whereby said fluorophores form an H-dimer resulting in quenching of the fluorescence of said fluorophores (e.g. a nucleic acid-backbone fluorogenic composition as described above); and detecting a change in fluorescence or absorbance of the fluorogenic composition where an increase in fluorescence or a change in absorbance indicates that the nuclease cleaves said nucleic acid backbone or that the nucleic acid hybridizes to the backbone. In certain preferred embodiments, the fluorogenic composition is attached to a solid support and/or is inside a cell (e.g. a mammalian cell). In certain embodiments, the contacting is in a histological section, a cell culture, a seeded or cultured adherent cell, or a cell suspension derived from a biological sample (e.g., tissue, blood, urine, saliva, lymph, biopsy). Detection is by any of a number of methods known to those of skill in the art. Such methods include, but are not limited to fluorescence microscopy, confocal microscopy, fluorescence microplate reader, flow cytometry, fluorometry, and absorption spectroscopy.

In yet another embodiment, this invention provides a method of detecting the interaction of a first and a second molecule. The method involves providing a first molecule having a first fluorophore attached thereto; providing a second molecule having a second fluorophore attached thereto wherein the first and second fluorophore are the same species of fluorophore and, when juxtaposed, form an H-dimer thereby quenching fluorescence produced by the fluorophores; and iii) detecting a change in fluorescence or absorbance produced by the fluorophores where a decrease in fluorescence or a change in absorbance indicates that the first molecule and the second molecule are interacting. Preferred first and second molecules include, but are not limited to a receptor and a receptor ligand, an antibody and an antigen, a lectin and a carbohydrate, a first protein and a second protein, and a nucleic acid and a nucleic acid binding protein. In particularly preferred embodiments, the fluorophore is linked to the first molecule by a linker. Preferred fluorophores include, but are not limited to, those described above.

This invention also provides a method of detecting a change in conformation or cleavage of a macromolecule. The method involves providing a macromolecule having attached thereto two fluorophores of the same species where the fluorophores form an H-dimer resulting in quenching of fluorescence of the fluorophores; and detecting a change in fluorescence or absorbance of the fluorophores wherein a change in fluorescence or fluorescence indicates a change in conformation or cleavage of the macromolecule. Preferred macromolecules, include, but are not limited to a polypeptide, a nucleic acid, a lipid, a polysaccharide, or an oligosaccharide. In various embodiments, the macromolecule is attached to a solid support or is inside a cell (e.g. a mammalian cell, an insect cell, a yeast cell, etc.). The macromolecule can, optionally, bear one or more hydrophobic groups e.g. a described above. Preferred fluorophores include, but are not limited to those described above. In certain embodiments, the contacting is in a histological section, a cell culture, a seeded or cultured adherent cell, or a cell suspension derived from a biological sample (e.g., tissue, blood, urine, saliva, lymph, biopsy). Detection is by any of a number of methods known to those of skill in the art. Such methods include, but are not limited to fluorescence microscopy, confocal microscopy, fluorescence microplate reader, flow cytometry, fluorometry, and absorption spectroscopy.

In still another embodiment, this invention provides a method of screening a test agent for the ability to modulate a protease (or a nuclease, lipase, etc.). The method involves contacting a protease or a cell comprising a protease with the test agent; contacting the protease with a fluorogenic indicator composition as described herein; and detecting a signal or lack of signal produced by the fluorogenic composition where a difference in the signal produced by the protease or cell contacted with the test agent compared to a control (e.g. a negative control) in which the protease or cell is contacted by said test agent at a lower concentration indicates that the test agent modulates activity of the protease. In preferred embodiments, the control comprises the absence of the test agent. Typically, an increase in signal produced by the protease or cell contacted with the test agent as compared to the control indicates that the test agent increases the activity of said protease, while a decrease in signal (e.g. fluorescence) produced by the protease or cell contacted with the test agent as compared to the control indicates that the test agent decreases the activity of said protease. The protease is contacted with the fluorogenic composition in the presence of the test agent in certain embodiments. In certain other embodiments, the protease is contacted with the fluorogenic composition after removal of the test agent. The method can further entail entering test agents that modulate activity of said protease into a database comprising a list of test agents modulating said protease. In various embodiments, the detecting comprises detecting an intracellular signal (e.g., via microscopy, flow cytometry, etc.). In certain particularly preferred embodiments, the detecting comprises high-throughput screening of whole cells.

Definitions

The term "protease binding site" is used herein to refer to an amino acid sequence that is characteristically recognized and cleaved by a protease. The protease binding site contains a peptide bond that is hydrolyzed by the protease and the amino acid residues joined by this peptide bond are said to form the cleavage site. These amino acids are designated $P_1$ and $P_1'$ for the residues on the amino and carboxyl sides of the hydrolyzed bond respectively.

A fluorophore is a molecule that absorbs light at a characteristic wavelength and then re-emits the light most typically at a characteristic different wavelength. Fluorophores are well known to those of skill in the art and include, but are not limited to rhodamine and rhodamine derivatives, fluorescein and fluorescein derivatives, coumarins and chelators with the lanthanide ion series. A fluorophore is distinguished from a chromophore which absorbs, but does not characteristically re-emit light.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variants on the traditional peptide linkage joining the amino acids making up the polypeptide. Preferred "peptides", "polypeptides", and "proteins" are chains of amino acids whose a carbons are linked through peptide bonds. The terminal amino acid at one end of the chain (amino terminal) therefore has a free amino group, while the terminal amino acid at the other end of the chain (carboxy terminal) has a free carboxyl group. As used herein, the term "amino terminus" (abbreviated N-terminus) refers to the free α-amino group on an amino acid at the amino terminal of a peptide or to the a α-amino group (imino group when participating in a peptide bond) of an amino acid at any other location within the peptide. Similarly, the term "carboxy terminus" refers to the free carboxyl group on the carboxy terminus of a peptide or the carboxyl group of an amino acid at any other location within the peptide. Peptides also include essentially any polyamino acid including, but not limited to peptide mimetics such as amino acids joined by an ether as opposed to an amide bond.

The polypeptides described herein are preferably written with the amino terminus at the left and the carboxyl terminus at the right. The amino acids comprising the peptide components of this invention are numbered with respect to the protease cleavage site, with numbers increasing consecutively with distance in both the carboxyl and amino direction from the cleavage site. Residues on the carboxyl site are either notated with a "'" as in $P_1$', or with a letter and superscript indicating the region in which they are located. The "'" indicates that residues are located on the carboxyl side of the cleavage site.

The term "residue" or "amino acid" as used herein refers to an amino acid that is incorporated into a peptide. The amino acid may be a naturally occurring amino acid and, unless otherwise limited, may encompass known analogs of natural amino acids that can function in a similar manner as naturally occurring amino acids.

The term "domain" or "region" refers to a characteristic region of a polypeptide. The domain may be characterized by a particular structural feature such as a β turn, an alpha helix, or a β pleated sheet, by characteristic constituent amino acids (e.g. predominantly hydrophobic or hydrophilic amino acids, or repeating amino acid sequences), or by its localization in a particular region of the folded three dimensional polypeptide. As used herein, a region or domain is composed of a series of contiguous amino acids.

The terms "protease activity" or "activity of a protease" refer to the cleavage of a peptide by a protease. Protease activity comprises the "digestion" of one or more peptides into a larger number of smaller peptide fragments. Protease activity of particular proteases may result in hydrolysis at particular peptide binding sites characteristically recognized by a particular protease. The particular protease may be characterized by the production of peptide fragments bearing particular terminal amino acid residues.

The terms "nucleic acid" or "oligonucleotide" refer to at least two nucleotides covalently linked together. A nucleic acid of the present invention is preferably single-stranded or double stranded and will generally contain phosphodiester bonds, although in some cases, as outlined below, nucleic acid analogs are included that may have alternate backbones, comprising, for example, phosphoramide (Beaucage et al. (1993) *Tetrahedron* 49(10):1925) and references therein; Letsinger (1970) *J. Org. Chem.* 35:3800; Sprinzl et al. (1977) *Eur. J. Biochem.* 81: 579; Letsinger et al. (1986) *Nucl. Acids Res.* 14: 3487; Sawai et al. (1984) *Chem. Lett.* 805, Letsinger et al. (1988) *J. Am. Chem. Soc.* 110: 4470; and Pauwels et al. (1986) *Chemica Scripta* 26: 1419), phosphorothioate (Mag et al. (1991) *Nucleic Acids Res.* 19:1437; and U.S. Pat. No. 5,644,048), phosphorodithioate (Briu et al. (1989) *J. Am. Chem. Soc.* 111 :2321, O-methylphosphoroamidite linkages (see Eckstein, *Oligonucleotides and Analogues: A Practical Approach*, Oxford University Press), and peptide nucleic acid backbones and linkages (see Egholm (1992) *J. Am. Chem. Soc.* 114:1895; Meier et al. (1992) *Chem. Int. Ed. Engl.* 31: 1008; Nielsen (1993) *Nature*, 365: 566; Carlsson et al. (1996) *Nature* 380: 207). Other analog nucleic acids include those with positive backbones (Denpcy et al. (1995) *Proc. Natl. Acad. Sci. USA* 92: 6097; non-ionic backbones (U.S. Pat. Nos. 5,386,023, 5,637,684, 5,602,240, 5,216,141 and 4,469,863; Angew. (1991) *Chem. Intl. Ed. English* 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghui and P. Dan Cook; Mesmaeker et al. (1994), *Bioorganic & Medicinal Chem. Lett.* 4: 395; Jeffs et al. (1994) *J. Biomolecular NMR* 34:17; *Tetrahedron Lett.* 37:743 (1996)) and non-ribose backbones, including those described in U.S. Pat. Nos. 5,235,033 and 5,034,506, and Chapters 6 and 7, ASC Symposium Series 580, *Carbohydrate Modifications in Antisense Research*, Ed. Y. S. Sanghui and P. Dan Cook. Nucleic acids containing one or more carbocyclic sugars are also included within the definition of nucleic acids (see Jenkins et al. (1995), *Chem. Soc. Rev.* pp169–176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments. Preferred nucleic acid backbones used in this invention range from about 5 nucleotides to about 500 nucleotides, preferably from about 10 nucleotides to about 100 nucleotides, more preferably from about 10 nucleotides to about 50 nucleotides, and most preferably from about 12 or 15 nucleotides to about 30, 40, or 50 nucleotides in length.

The term "test agent" refers to an agent that is to be screened in one or more of the assays described herein. The agent can be virtually any chemical compound. It can exist as a single isolated compound or can be a member of a chemical (e.g. combinatorial) library. In a particularly preferred embodiment, the test agent will be a small organic molecule.

The term "small organic molecule" refers to a molecule of a size comparable to those organic molecules generally used in pharmaceuticals. The term excludes biological macromolecules (e.g., proteins, nucleic acids, etc.). Preferred small organic molecules range in size up to about 3000 Da, more preferably up to 2000 Da, and most preferably up to about 1000 Da.

The term macromolecule refers to a "large" molecule. Biopolymers (e.g. proteins, glycoproteins, carbohydrates, lipids, polysaccharides, and the like) are typical macromolecules. Typical macromolecules have a molecular weight greater than about 1000 Da, preferably greater than about 2000 Da, more preferably greater than about 3000 Da, and most preferably greater than about 4,000 or 5,000 Da.

The term database refers to a means for recording and retrieving information. In preferred embodiments the database also provides means for sorting and/or searching the stored information. The database can comprise any convenient media including, but not limited to, paper systems, card systems, mechanical systems, electronic systems, optical systems, magnetic systems or combinations thereof. Preferred databases include electronic (e.g. computer-based) databases. Computer systems for use in storage and manipulation of databases are well known to those of skill in the art and include, but are not limited to "personal computer systems", mainframe systems, distributed nodes on an inter- or intra-net, data or databases stored in specialized hardware (e.g. in microchips), and the like.

The term "biological sample", as used herein, refers to a sample obtained from an organism, from components (e.g., cells or tissues) of an organism, and/or from in vitro cell or tissue cultures. The sample may be of any biological tissue or fluid (e.g. blood, serum, lymph, cerebrospinal fluid, urine, sputum, etc.). Biological samples can also include whole organisms, organs or sections of tissues such as frozen sections taken for histological purposes.

The term "specifically binds", when referring to the interaction of a nucleic acid binding protein and a nucleic acid binding site or two proteins or other binding pairs refers to a binding reaction which is determinative of the presence of the one or other member of the binding pair in the presence of a heterogeneous population of molecules (e.g., proteins and other biologics). Thus, for example, in the case of a receptor/ligand binding pair the ligand would specifically and/or preferentially select its receptor from a complex mixture of molecules, or vice versa. An enzyme would specifically bind to its substrate, etc. The binding may be by one or more of a variety of mechanisms including, but not limited to ionic interactions, covalent interactions, hydrophobic interactions, van der Waals interactions, etc.

The terms "binding partner", or a member of a "binding pair", or "cognate ligand" refers to molecules that specifically bind other molecules to form a binding complex such as antibody/antigen, lectin/carbohydrate, nucleic acid/nucleic acid, receptor/receptor ligand (e.g. IL-4 receptor and IL-4), avidin/biotin, etc.

The term ligand is used to refer to a molecule that specifically binds to another molecule. Commonly a ligand is a soluble molecule, e.g. a hormone or cytokine, that binds to a receptor. The decision as to which member of a binding pair is the ligand and which the "receptor" is often a little arbitrary when the broader sense of receptor is used (e.g., where there is no implication of transduction of signal). In these cases, typically the smaller of the two members of the binding pair is called the ligand. Thus, in a lectin-sugar interaction, the sugar would be the ligand (even if it is attached to a much larger molecule, recognition is of the saccharide).

The terms "hybridizing specifically to" and "specific hybridization" and "selectively hybridize to," as used herein refer to the binding, duplexing, or hybridizing of a nucleic acid molecule preferentially to a particular nucleotide sequence under stringent conditions. The term "stringent conditions" refers to conditions under which a probe will hybridize preferentially to its target subsequence, and to a lesser extent to, or not at all to, other sequences. Stringent hybridization and stringent hybridization wash conditions in the context of nucleic acid hybridization are sequence dependent, and are different under different environmental parameters. An extensive guide to the hybridization of nucleic acids is found in, e.g., Tijssen (1993) *Laboratory Techniques in Biochemistry and Molecular Biology—Hybridization with Nucleic Acid Probes part I, chapt 2, Overview of principles of hybridization and the strategy of nucleic acid probe assays*, Elsevier, N.Y. (Tijssen). Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on an array or on a filter in a Southern or northern blot is 42° C. using standard hybridization solutions (see, e.g., Sambrook (1989) *Molecular Cloning: A Laboratory Manual* (2nd ed.) Vol. 1–3, Cold Spring Harbor Laboratory, Cold Spring Harbor Press, NY, and detailed discussion, below), with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, e.g., Sambrook supra.) for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example of a low stringency wash for a duplex of, e.g., more than 100 nucleotides, is 4× to 6×SSC at 40° C. for 15 minutes.

The term "nucleic acid array" refers to a collection of nucleic acids comprising a multiplicity of different nucleic acids (nucleic acid species). The nucleic acids are typically attached to a solid support. The support can be contiguous and of virtually any convenient geometry (e.g. a glass or quartz slide). In other embodiments, the support is not contiguous, e.g., where the array nucleic acids are disposed on a collection of particles, e.g. beads. The nucleic acids comprising the array can be chemically synthesized nucleic acids, naturally occurring nucleic acids, cloned nucleic acids, or any combination thereof. Preferred nucleic acid arrays are "high density arrays" or "microarrays". Typically such microarrays have a density of greater than about 100, preferably greater than about 1000, more preferably greater than about 10,000, and most preferably greater than about 100,000 array elements per square centimeter.

The term "array element" refers to a domain of an array comprising substantially one species of nucleic acid.

Two fluorophores are said to quench each other in an H-dimer when their aggregate fluorescence in an H-dimer formation is detectably less than the aggregate fluorescence of the fluorophores when they are separated (e.g. in solution at approximately 10 $\mu$M or less). In preferred embodiments the fluorophores quench by at least 50%, preferably by at least 70%, more preferably by at least 80%, and most preferably by at least 90%, 95%, or even at least 99%.

Certain amino acids referred to herein are described by shorthand designations as shown in Table 1.

TABLE 1

Amino acid nomenclature.

| Name | Abbreviation | |
|---|---|---|
| | 3 Letter | 1 Letter |
| Alanine | Ala | A |
| βAlanine (NH$_2$—CH$_2$—CH$_2$—COOH) | βAla | |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Homoserine | Hse | — |
| Isoleucine | Ile | I |
| Leucine | Leu | L |
| Lysine | Lys | K |
| Methionine | Met | M |
| Methionine sulfoxide | Met (O) | — |
| Methionine methylsulfonium | Met (S—Me) | — |
| Norleucine | Nle | — |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| episilon-aminocaproic acid (NH$_2$—(CH$_2$)$_5$—COOH) | Ahx | J |
| 4-aminobutanoic acid (NH$_2$—(CH$_2$)$_3$—COOH) | gAbu | — |
| tetrahydroisoquinoline-3-carboxylic acid | — | O |
| 8-aminocaprylic acid | — | C7 |

TABLE 1-continued

Amino acid nomenclature.

| Name | Abbreviation | |
|---|---|---|
| | 3 Letter | 1 Letter |
| 4-aminobutyric acid | — | C3 |
| Lys(N(epsilon)-trifluoroacetyl) | — | K[TFA] |
| α-aminoisobutyric acid | Aib | B |

Other abbreviations used herein include "Fm" for Fmoc (9-fluorenylmethoxycarbonyl) group, "Ac" for N(alpha)-acetyl group, "daa" or (d-aa) where "d" indicates the d isomer of the aa, and "Z" for benzyloxycarbonyl group.

BRIEF DESCRIPTION OF THE DRAWINGS

FIG. 1A: HPLC before the addition of elastase showing the late eluting peak representing the intact indicator molecule. FIG. 1B: HPLC after the addition of elastase with detection at 550 nm where both fluorophores absorb. FIG. 1C HPLC after the addition of elastase with detection at 580 nm where $F^2$ absorbs maximally.

FIG. 4A: The fluorogenic protease indicator of FIG. 1. FIG. 4B: The peptide backbone of the fluorogenic protease of FIG. 1 singly labeled with each of the two fluorophores. D-NorFES-A is the $F^1$-Asp-Ala-Ile-Pro-Nle-Ser-Ile-Pro-Cys-$F^2$ protease indicator where $F^1$ is a donor fluorophore (5'-carboxytetramethylrhodamine (C2211) and $F^2$ is an acceptor fluorophore (rhodamine X acetamide (R492). D-NorFES and A-NorFES each designate a molecule having the same peptide backbone, but bearing only one of the two fluorophores.

DETAILED DESCRIPTION

I. Fluorogenic Indicators of Protease Activity

Figure 1A:
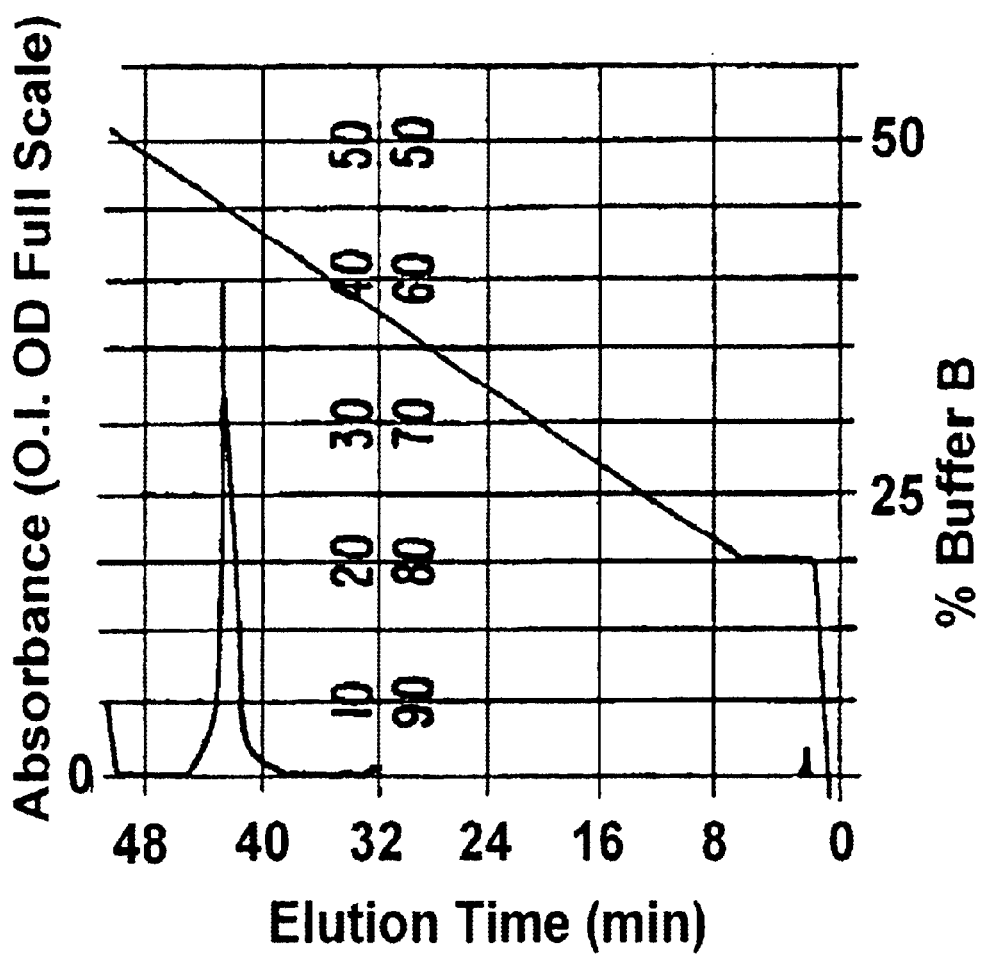
FIGS. 1A, 1B, and 1C show an HPLC analysis of the D-NorFES-A protease indicator ($F^1$-Asp-Ala-Ile-Pro-Nle-Ser-Ile-Pro-Cys-$F^2$, SEQ ID NO:1) where $F^1$ is a donor (D) fluorophore (5'-carboxytetramethyirhodamine (C2211) and $F^2$ is an acceptor (A) fluorophore (rhodamine X acetamide (R492))) before and after the addition of elastase.

This invention provides for novel fluorogenic molecules useful for detecting protease activity in a sample. In certain embodiments, the fluorogenic protease indicators of the present invention generally comprise a fluorophore (donor) linked to an "acceptor" molecule by a peptide having an amino acid sequence that is recognized and cleaved by a particular protease. The donor fluorophore typically is excited by incident radiation at a particular wavelength which it then re-emits at a different (longer) wavelength. When the donor fluorophore is held in close proximity to the acceptor molecule, the acceptor absorbs the light re-emitted by the fluorophore thereby quenching the fluorescence signal of the donor molecule, or the putative donor and acceptor form a complex which absorbs the incident light and does not release radiative energy until the complex is disrupted. In this latter embodiment, the quench occurs whether the two fluorophores are different or the same species. Thus, in addition to peptides double labeled with two different fluorophores as shown in Example 1, peptides double labeled with the same fluorophore (or chromophore) may also be used as protease indicators (see, e.g., Example 6). Cleavage of the (e.g. peptide) backbone joining the two fluorophores or chromophores results in separation of the two molecules, release of the quenching effect and increase in fluorescence or a change in spectral characteristics.

In one basic application, the fluorogenic molecules of this invention may be used to assay the activity of purified protease made up as a reagent (e.g. in a buffer solution) for experimental or industrial use. Like many other enzymes, proteases may loose activity over time, especially when they are stored as their active forms. In addition, many proteases exist naturally in an inactive precursor form (e.g. a zymogen) which itself must be activated by hydrolysis of a particular peptide bond to produce the active form of the enzyme prior to use. Because the degree of activation is variable and because proteases may loose activity over time, it is often desirable to verify that the protease is active and to often quantify the activity before using a particular protease in a particular application.

Previous approaches to verifying or quantifying protease activity involve combining an aliquot of the protease with its substrate, allowing a period of time for digestion to occur and then measuring the amount of digested protein, most typically by HPLC. This approach is time consuming, utilizes expensive reagents, requires a number of steps and entails a considerable amount of labor. In contrast, the fluorogenic reagents of the present invention allow rapid determination of protease activity in a matter of minutes in a single-step procedure. An aliquot of the protease to be tested is simply added to, or contacted with, the fluorogenic reagents of this invention and the subsequent change in fluorescence is monitored (e.g., using a fluorimeter or a fluorescence microplate reader).

In addition to determining protease activity in "reagent" solutions, the fluorogenic compositions of the present invention may be utilized to detect protease activity in biological samples. The term "biological sample", as used herein, refers to a sample obtained from an organism or from components (e.g., cells) of an organism. The sample may be of any biological tissue or fluid. Frequently the sample will be a "clinical sample" which is a sample derived from a patient. Such samples include, but are not limited to, sputum, blood, blood cells (e.g., white cells), tissue or fine needle biopsy samples, urine, peritoneal fluid, and pleural fluid, or cells therefrom. Biological samples may also include sections of tissues such as frozen sections taken for histological purposes.

Previously described fluorogenic protease indicators typically absorb light in the ultraviolet range (e.g., Wang et al., supra.). They are thus unsuitable for sensitive detection of protease activity in biological samples which typically contain constituents (e.g., proteins) that absorb in the ultraviolet range. In contrast, in preferred embodiments, the fluorescent indicators of the present invention both absorb and emit in the visible range (400 nm to about 750 nm). These signals are therefore not readily quenched by, nor is activation of the fluorophores, that is, absorption of light, interfered with by background molecules; therefore they are easily detected in biological samples.

In addition, unlike previous fluorogenic protease indicators which often utilize a fluorophore and a quenching chromophore, the indicators of the present invention may utilize two fluorophores (i.e., fluorophore as both donor and acceptor), a fluorophore and a chromophore, or the same two fluorophores effectively forming a ground-state dimer when joined by the one of the peptide backbones of this invention. Pairs of fluorophores may be selected that show a much higher degree of quenching than previously described chromophore/fluorophore combinations. In fact, previous compositions have been limited to relatively low efficiency fluorophores because of the small degree of quenching obtainable with the matching chromophore (Wang et al. supra.). In contrast, the fluorogenic protease indicators of this invention utilize high efficiency fluorophores and are able to achieve a high degree of quenching while providing a strong signal when the quench is released by cleavage of the peptide substrate. The high signal allows detection of very low levels of protease activity. Thus the fluorogenic protease indicators of this invention are particularly well suited for in situ detection of protease activity.

Preferred fluorogenic protease indicators of the present invention have the general formula:

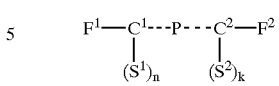

I where P is a peptide comprising a protease binding site, $F^1$ and $F^2$ are fluorophores, $C^1$ and $C^2$ are conformation determining regions, and $S^1$ and $S^2$ are optional peptide spacers. $F^1$ may be the donor fluorophores or chromophore while $F^2$ is the acceptor fluorophores or chromophore, or conversely, $F^2$ may be the donor fluorophore or chromophore while $F^1$ is the acceptor fluorophores or chromophore, or $F^1$ and $F^2$ may be identical (fluorophores or chromophores). The protease binding site provides an amino acid sequence (a peptide) that is recognized and cleaved by the protease whose activity the indicator is designed to reveal. The protease binding site is typically a peptide ranging in length from 2 amino acids to about 12 amino acids, 2 to about 10, 2 to about 8, 2 to about 6 or 2 to about 4 amino acids in length.

A preferred conformation determining region is an amino acid sequence that allows a bend into the molecule, restricts the degrees of freedom of the peptide backbone, or otherwise results in the two ends of the backbone being in close proximity. The combined effect of the two conformation determining regions is to juxtapose the fluorophores or chromophores attached to the amino and carboxyl termini of $C^1$ and $C^2$ respectively. The fluorophores are thus preferably positioned adjacent to each other at a distance less than about 100 angstroms. The fluorophores ($F^1$ and $F^2$) are typically conjugated directly to the conformation determining regions, although they may be joined by linkers. The optional spacers ($S^1$ and $S^2$), when present, can be used to link the composition to a solid support or to anchor the composition to a component of a biological sample (e.g., to a cellular membrane). The spacers can also provide additional, or alternative, functionality. For example, a spacer can comprise the amino acids GY to provide an optical signature for ready detection of the peptide by HPLC.

The substantially conformation determining regions increases the protease specificity of the composition. The amino acid sequences comprising the conformation determining regions are typically less accessible to the enzyme due to steric hindrance with each other and with the attached fluorophores. Conversely, the protease binding site is relatively unobstructed by either the fluorophore or the conformational determining region and is thus readily accessible to the protease.

II. Protease Binding Site

In preferred embodiments, the protease binding site and conformation determining regions form a contiguous amino acid sequence (peptide). The protease binding site is an amino acid sequence that is recognized and cleaved by a particular protease. It is well known that various proteases cleave peptide bonds adjacent to particular amino acids. Thus, for example, trypsin cleaves peptide bonds following basic amino acids such as arginine and lysine and chymotrypsin cleaves peptide bonds following large hydrophobic amino acid residues such as tryptophan, phenylalanine, tyrosine and leucine. The serine protease elastase cleaves peptide bonds following small hydrophobic residues such as alanine.

A particular protease, however, will not cleave every bond in a protein that has the correct adjacent amino acid. Rather, the proteases are specific to particular amino acid sequences which serve as recognition domains for each particular protease. Without being bound by a particular theory, it is believed that a specific protease's preference for a particular cleavage site over many other potential sites in a folded globular protein may be largely determined by the potential cleavage site's amino acid sequences and also their conformation and conformational flexibility.

Thus, for example, one obtains limited proteolysis products, e.g., ribonuclease-S (a noncovalent complex consisting of two polypeptide chains) from a single chain folded protein ribonuclease-A using a protease called subtilisin. Similarly, one obtains a two chain noncovalent complex, Staphylococal nuclease-T, from single chain Staphylococcal nuclease by trypsin digestion. Another example of a specific protease's preference for one substrate over others is the human fibroblast-type collagenase. This protease prefers type I over type III soluble collagen even though both substrates contain the same collagenase sensitive Gly-Ile or Gly-Leu bonds (see, e.g., Birkedal-Hansen et. al. (1993) *Crit. Rev. in Oral Biology and Medicine* 4:197–250).

Any amino acid sequence that comprises a recognition domain and can thus be recognized and cleaved by a protease is suitable for the "protease binding site" of the fluorogenic protease indicator compositions of this invention. Known protease substrate sequences and peptide inhibitors of proteases posses amino acid sequences that are recognized by the specific protease they are cleaved by or that they inhibit. Thus known substrate and inhibitor sequences provide the basic sequences suitable for use in the protease recognition region. A number of protease substrates and inhibitor sequences suitable for use as protease binding domains in the compositions of this invention are indicated in Table 2. One of skill will appreciate that this is not a complete list and that other protease substrates or inhibitor sequences may be used.

The amino acid residues comprising the protease binding site are, by convention, numbered relative to the peptide bond hydrolyzed by a particular protease. Thus the first amino acid residue on the amino side of the cleaved peptide bond is designated $P_1$ while the first amino acid residue on the carboxyl side of the cleaved peptide bond is designated $P_1'$. The numbering of the residues increases with distance away from the hydrolyzed peptide bond. Thus a four amino acid protease binding region would contain amino acids designated:

$P_2$-$P_1$-$P_1'$-$P_2'$ and the protease would cleave the binding region between $P_1$ and $P_1'$.

In certain preferred embodiments, the protease binding region of the protease indicators of the present invention is selected to be symmetric about the cleavage site. Thus, for example, where a binding region is:

Ile-Pro-Met-Ser-Ile            (SEQ ID NO:2)

(e.g. α-1 anti-trypsin) and the cleavage occurs between Met and Ser then a four amino acid residue binding region based on this sequence would be:

—$P_2$-$P_1$-$P_1'$-$P_2'$—

—Pro-Met-Ser-Ile—            (SEQ ID NO:3)

Other examples of binding domains selected out of longer sequences are provided in Table 2. The remaining amino or carboxyl residues that are not within the protease binding domain may remain as part of the conformation determining regions subject to certain limitations as will be explained below. Thus, in the instant example, the amino terminal Ile may be incorporated into the $C^1$ conformation determining region.

Various amino acid substitutions may be made to the amino acids comprising the protease binding domain to increase binding specificity, to eliminate reactive side chains, or to reduce the conformational entropy (decrease degrees of freedom) of the molecule. Thus, for example, it is often desirable to substitute methionine (Met) residues, which bear a oxidizable sulfur, with norleucine. Thus, in the example given, a preferred protease binding region will have the sequence:

—$P_2$-$P_1$-$P_1'$-$P_2'$—

—Pro-Nle-Ser-Ile—            (SEQ ID NO:4)

III. Conformation Determining Regions

Conformation determining regions ($C^1$ and $C^2$) are peptide regions on either end of the protease cleavage region that both stiffen and allow bends into the peptide backbone of the fluorogenic protease indicator molecules of this invention. In certain embodiments the conformation determining regions can introduce flexibility at particular locations, e.g, to permit the cleavage site to sit in a protein cleft. The combination of the two conformation determining regions and the relatively straight protease cleavage region produces a roughly U-shaped molecule with the cleavage site at the base (middle) of the "U". The term U-shaped is, of course, approximate, the point being that, as described below, the fluorophores are held relatively rigidly in close juxtaposition (e.g., less than about 100 angstroms).

In one preferred embodiment, amino acids such as proline (Pro) and α-aminoisobutyric acid (Aib) are selected both to introduce bends into the peptide molecule and to increase the rigidity of the peptide backbone. The $C^1$ and $C^2$ domains are selected such that the "arms" of the U are rigid and the attached fluorophores are localized adjacent to each other at a separation of less than about 100 angstroms. In order to maintain the requisite stiffness of the peptide backbone and/or to provide the flexibility of adjacent residues such that a local bend at the binding site is possible to improve substrate specificity, the conformation determining regions are preferably 4 amino acids in length or less, or alternatively are greater than about 18 amino acids in length and form a stable alpha helix conformation, a β-pleated sheet, or loop.

A) Tetrapeptide Binding Site Compositions.

In a preferred embodiment, the peptide backbone of the fluorogenic protease indicators of the present invention will comprise a tripeptide $C^1$ region, a tetrapeptide P region and a single amino acid or dipeptide $C^2$ region. These compounds may be represented by the formula:

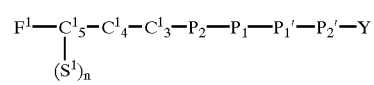
                                                            II where Y is either

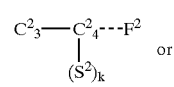
                                                            III or

-continued

IV

In these formulas the peptide binding region is designated —$P_2$-$P_1$-$P_1'$-$P_2'$—, while the amino acid residues of conformation determining regions $C^1$ and $C^2$ are designated —$C^1_5$-$C^1_4$-$C^1_3$— and —$C^2_3$-$C^2_4$— respectively. The $C^2$ region may either be an amino acid or a dipeptide. Whether the $C^2$ region is a dipeptide or an amino acid, the $F^2$ fluorophore and the $S^2$ spacer, when present, are always coupled to the carboxyl terminal residue of $C^2$. When a spacer is present on the $C^2$ region, it is attached the carboxyl terminal residue of $C^2$ by a peptide bond to the α carboxyl group.

As indicated above, the conformation determining regions typically contain amino acid residues such as a proline (Pro) that introduce a bend into the molecule and increase its stiffness. One of skill in the art will appreciate, however, that where the terminal residues of the protease binding region (P) are themselves bend-creating residues such as proline, it is not necessary to locate a bend-creating residue at the position closest to P in the C region attached to that terminus. The conformation determining regions are thus designed by first determining the protease binding region, as described above, determining the "left-over" residues that would lie in the conformation determining regions, and if necessary, modifying those residues according to the following guidelines:

1. If the $P_2'$ site is not a Pro then $C^2$ is a dipeptide (Formula III) Pro-Cys, Aib-Cys, Pro-Lys, or Aib-Lys, while conversely, if the $P_2'$ site is a Pro then $C^2$ is a single amino acid residue (Formula IV) Cys or Lys.
2. If the $P_2$ site is not a Pro then $C^1$ is a tripeptide consisting of Asp-$C^1_4$-Pro, Asp-$C^1_4$-Aib, Asp-Aib-Pro, Asp-Pro-$C^1_3$, Asp-Aib-$C^1_3$, Asp-Pro-Aib, or Asp-Aib-Aib, while if the $P_2$ site is a Pro residue then group $C^1$ is a tripeptide consisting of Asp-$C^1_4$-$C^1_3$ or Asp-$C^1_4$-Aib.
3. If the $P_3$ ($C^1_3$) residue is a Pro then $C^1$ is a tripeptide consisting of Asp-$C^1_4$-Pro or Asp-Aib-Pro.
4. If the $P_4$ ($C^1_4$) residue is a Pro then $C^1$ is a tripeptide consisting of Asp-Pro-$C^1_3$ or Asp-Pro-Aib.
5. If $P_2$ and $C^1_3$ are both not prolines then $C^1$ is a tripeptide consisting of Asp-Pro-$C^1_3$, Asp-Aib-$C^1_3$, Asp-$C^1_4$-Pro, Asp-$C^1_4$-Aib, Asp-Pro-Aib, or Asp-Aib-Pro.

As indicated above, any methionine (Met) may be replaced with a norleucine (Nle). A number of suitable peptide backbones consisting of $C^1$, P and $C^2$ are provided in Table 2.

TABLE 2

Illustration of the design of the conformation determining regions and protease binding site based on known protease substrate and inhibitor sequences. Italics indicate residues that are added to create a bend and to increase rigidity of the conformation determining regions. Normal font indicates residues of the substrate or inhibitor that forms the protease binding site. The thick line indicates the location at which the protease binding site is cleaved.

| Substrate/Inhibitor | CDR ($C^1$) | | | Protease Binding Site (P) | | | | CDR ($C^2$) | | SEQ ID NO |
|---|---|---|---|---|---|---|---|---|---|---|
| | $C^1_5$ | $C^1_4$ | $C^1_3$ | $P_2$ | $P_1$ | $P_1'$ | $P_2'$ | $C^2_3$ | $C^2_4$ | |
| α-1 anti-trypsin | Asp | Ala | Ile | Pro | Met Nle | Ser | Ile | Pro Aib | Cys Lys | 5 |
| plasminogen activator inhibitor 2 | Asp | Met Aib Pro | Thr Aib Pro | Gly | Arg | Thr | Gly | Pro Aib | Cys Lys | 6 |
| neutrophil leukocyte elastase inhibitor | Asp | Ala Aib | Thr Aib Pro | Phe | Cys | Met Nle | Leu | Pro Aib | Cys Lys | 7 |
| anti-plasmin inhibitor | Asp | Aib | Ser Aib Pro | Arg | Met Nle | Ser | Leu | Pro Aib | Cys Lys | 8 |
| anti α-1 thrombin | Asp | Ile Aib | Ala Aib Pro | Gly | Arg | Ser | Leu | Pro Aib | Cys Lys | 9 |
| α-1 antichymotrypsin | Asp | Aib | Thr Aib Pro | Leu | Leu | Ser | Leu | Pro Aib | Cys Lys | 10 |
| interstitial type III (human liver) collagen | Asp | Gly Aib | Pro Aib | Leu | Gly | Ile | Ala | Pro Aib | Cys Lys | 11 |

TABLE 2-continued

Illustration of the design of the conformation determining regions and protease binding site based on known protease substrate and inhibitor sequences. Italics indicate residues that are added to create a bend and to increase rigidity of the conformation determining regions. Normal font indicates residues of the substrate or inhibitor that forms the protease binding site. The thick line indicates the location at which the protease binding site is cleaved.

| | | | | | | | | | | |
|---|---|---|---|---|---|---|---|---|---|---|
| type I collagen for collagenase Bovine α1 | Asp | Gly *Aib Pro* | Pro *Aib* | Gln | Gly | Ile | Leu | Pro *Aib* | Cys Lys | 12 |
| type I collagen chick α2 | Asp | Gly *Aib Pro* | Pro *Aib* | Gln | Gly | Leu | Leu | Pro *Aib* | Cys Lys | 13 |
| human α1 type II collagen | Asp | Gly *Aib Pro* | Pro *Aib* | Gln | Gly | Ile | Ala | Pro *Aib* | Cys Lys | 14 |
| type III collagen-AIA | Asp | Gly *Aib Pro* | Pro *Aib* | Gln | Ala | Ile | Ala | Pro *Aib* | Cys Lys | 15 |
| type III collagen (human skin) | *Asp* | Gly *Aib Pro* | Pro *Aib* | Gln | Gly | Ile | Ala | Pro *Aib* | Cys Lys | 16 |
| human α2 macroglobulin | *Asp* | Gly *Aib Pro* | Pro *Aib* | Glu | Gly | Leu | Arg | Pro *Aib* | Cys Lys | 17 |
| stromelysin cleavage sites of stromelysin-1d | *Asp* | Asp *Aib Pro* | Val *Aib Pro* | Gly | His | Phe | Arg | Pro *Aib* | Cys Lys | 18 |
| stromelysin cleavage sites of stromelysin-1 | *Asp* | Asp *Aib Pro* | Thr *Aib Pro* | Leu | Glu | Val | Met *Nle* | Pro *Aib* | Cys Lys | 19 |
| stromelysin cleavage site of proteoglycan link protein | *Asp* | Arg *Aib Pro* | Ala *Aib Pro* | Ile | His | Ile | Gln | Pro *Aib* | Cys Lys | 20 |
| gelatinase type IV collagenase site of 72 K gelatinases | *Asp* | Asp *Aib Pro* | Val *Aib Pro* | Ala | Asn | Tyr | Asn | Pro *Aib* | Cys Lys | 21 |
| gelatinase type IV cleavage of gelatin | *Asp* | Gly *Aib Pro* | Pro *Aib* | Ala | Gly | Glu | Arg | Pro *Aib* | Cys Lys | 22 |
| gelatinase type IV cleavage of gelatin | *Asp* | Gly *Aib Pro* | Pro *Aib* | Ala | Gly | Phe | Ala | Pro *Aib* | Cys Lys | 23 |
| type III collagen (human skin) | *Asp* | Gly *Aib Pro* | Pro *Aib* | Gln | Gly | Leu | Ala | Pro *Aib* | Cys Lys | 24 |
| Human FIB-CL propeptide | *Asp* | Asp *Aib Pro* | Val *Aib Pro* | Ala | Gln | Phe | Val | Pro *Aib* | Cys Lys | 25 |
| Cathepsin D (Thyroglobulin Fragment Tg1) | *Asp* | Asp *Aib Pro* | Gly *Pro Aib* | His | Phe | Leu | Arg | Pro *Aib* | Cys Lys | 26 |
| Cathepsin D (Thyroglobulin Fragment Tg2) | *Asp* | Thr *Aib Pro* | Thr *Pro Aib* | Glu | Leu | Phe | Ser | Pro *Aib* | Cys Lys | 27 |
| Cathepsin D (Thyroglobulin Fragment Tg3) | *Asp* | Lys *Aib Pro* | Phe *Pro Aib* | leu | Ala | Phe | Leu | Pro *Aib* | Cys Lys | 28 |
| Cathepsin D (Thyroglobulin Fragment Tg4) | *Asp* | Phe *Aib Pro* | Ser *Pro Aib* | His | Phe | Val | Arg | Pro *Aib* | Cys Lys | 29 |

TABLE 2-continued

Illustration of the design of the conformation determining regions and protease binding site based on known protease substrate and inhibitor sequences. Italics indicate residues that are added to create a bend and to increase rigidity of the conformation determining regions. Normal font indicates residues of the substrate or inhibitor that forms the protease binding site. The thick line indicates the location at which the protease binding site is cleaved.

| | | | | | | | | | | |
|---|---|---|---|---|---|---|---|---|---|---|
| Prostate Specific Antigen (PSA) (Seminolgelin, Sg) Sg1 | Asp | Gln *Aib* *Pro* | Gln *Pro* *Aib* | Leu | Leu | His | Asn | *Pro* *Aib* | Cys Lys | 30 |
| Prostate Specific Antigen (PSA) (Seminolgelin, Sg) Sg2 | Asp | Ser *Aib* *Pro* | Ile *Pro* *Aib* | Gln | Tyr | Thr | Tyr | *Pro* *Aib* | Cys Lys | 31 |
| Prostate Specific Antigen (PSA) (Seminolgelin, Sg) Sg3 | Asp | Ser *Aib* *Pro* | Ser *Pro* *Aib* | Gln | Tyr | Ser | Asn | *Pro* *Aib* | Cys Lys | 32 |
| Prostate Specific Antigen (PSA) (Seminolgelin, Sg) Sg4 | Asp | Ser *Aib* *Pro* | Ser *Pro* *Aib* | Ile | Tyr | Ser | Gln | *Pro* *Aib* | Cys Lys | 33 |
| Gelatin α1 (type 1) | *Asp* | Gly *Aib* *Pro* | Pro *Aib* | Ala | Gly | Val | Gln | *Pro* *Aib* | Cys Lys | 34 |

In a preferred embodiment, the sequence may be followed by an $S_2$ spacer of Gly-Tyr. Thus, for example, where $C^2{}_4$ is Lys, $C^2{}_4$-$S_2$ is Lys-Gly-Tyr.

B) Indicators Having Other Binding Sites.

In another preferred embodiment, the binding site (P) ranges from 2 to about 12 amino acids in length. It was a discovery of this invention, that somewhat larger conformation determining regions can sufficiently restrict the degrees of freedom of the indicator molecule, that the fluorophores are suitably quenched regardless of the amino acid sequence of the binding (recognition) domain (P). In one preferred embodiment, these compositions are include the compounds represented by the Formula V:

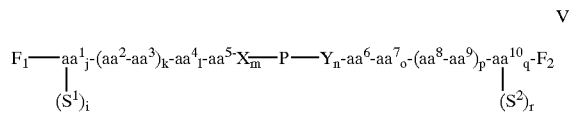

V

In this formula, P is a peptide comprising a protease binding site and consists of 2 to about 12 amino acids, $F^1$ and $F^2$ are fluorophores where $F^1$ is attached to the amino terminal amino acid and $F^2$ is attached to the carboxyl terminal amino acid of the composition (excluding spacers). $S^1$ and $S^2$, when present, are peptide spacers ranging in length from 1 to about 50 amino acids and $S^1$, when present, is attached to the amino terminal amino acid, while $S^2$, when present, is attached to the carboxyl terminal amino acid. The subscripts i, j, k, l, m, n, o, p, q, and r are independently 0 or 1.

In a particularly preferred embodiment, $aa^1$ and $aa^{10}$ are independently selected from the group consisting of lysine, ornithine and cysteine; $aa^2$, $aa^3$, $aa^8$ and $aa^9$ are independently selected from the group consisting of an amino acid or a dipeptide consisting of Asp, Glu, Lys, Ornithine, Arg, Citulline, homocitrulline, Ser, homoserine, Thr, and Tyr; $aa^5$, $aa^4$, $aa^6$, and $aa^7$ are independently selected from the group consisting of proline, 3,4-dehydroproline, hydroxyproline, alpha aminoisobutyric acid and N-methyl alanine; X is selected from the group consisting of Gly, βAla, γAbu ,Gly-Gly, Ahx, βAla-Gly, βAla-βAla, γAbu-Gly, βAla-γAbu, Gly-Gly-Gly, γAbu-γAbu, Ahx-Gly, βAla-Gly-Gly, Ahx-βAla, βAla-βAla-Gly, Gly-Gly-Gly-Gly (SEQ ID NO:35), Ahx-γAbu, βAla-βAla-βAla, γAbu-βAla-Gly, γAbu-γAbu-Gly, Ahx-Ahx, γAbu-γAbu-βAla, and Ahx-Ahx-Gly; Y is selected from the group consisting of Gly, βAla, γAbu, Gly-Gly, Ahx, Gly-βAla, βAla-βAla, Gly-γAbu, γAbu-βAla, Gly-Gly-Gly, γAbu-γAbu, Gly-Ahx, Gly-Gly-βAla, βAla-Ahx, Gly-βAla-βAla, Gly-Gly-Gly-Gly (SEQ ID NO:35), γAbu-Ahx, βAla-βAla-βAla, Gly-βAla-γAbu, Gly-γAbu-γAbu, Ahx-Ahx, βAla-γAbu-γAbu, and Gly-Ahx-Ahx.

When i is 1, $S^1$ is joined to $aa^1$ by a peptide bond through a terminal alpha amino group of $aa^1$; and when r is 1, $S^2$ is joined to $aa^{10}$ by a peptide bond through a terminal alpha carboxyl group of $aa^{10}$. It will be appreciated that amino acids 1–4 or 7–10 may be absent. When one or more of these amino acids are absent, the fluorophores are attached to the remaining terminal amino acids.

The amino acid backbones of such particularly preferred compositions are listed in Tables 3 and 4.

TABLE 3

Illustration of the design of the conformation determining regions and protease binding sites in molecules having P domains larger that 4 amino acids. The P1 residue is underlined. Z is benzyloxycarbonyl group, K[TFA] means Lys(N(epsilon)trifluoroacetyl), Fm is Fmoc (preferably attached to the alpha amino group of the amino terminal residue e.,g., Lysine (K). O indicates tetrahydroisoquinoline-3-carboxylic acid. Aib, designated as B, can be replaced by Pro.

| Name | $aa^1$ | $aa^2$-$aa^3$ | $aa^4$ | $aa^5$ | X | P | Y | $aa^6$ | $aa^7$ | $aa^8$-$aa^9$ | $aa^{10}$ | $S^2$ | SEQ ID NO |
|---|---|---|---|---|---|---|---|---|---|---|---|---|---|
| PAI-2 | K | D | | B | | TGRTG | | P | | | K | GY | 36 |
| PAI-2(b) | K | D | P | P | | TGRTG | | P | P | | K | GY | 37 |
| DEVD | K | D | | B | | DEVDGID | | P | | | K | GY | 38 |
| DevN | K | D | | B | | DEVNGID | | P | | | K | GY | 39 |
| PARP | K | D | | B | | EVDGID | | P | | | K | GY | 40 |
| ICE | K | DY | | B | | ADGID | | P | | | K | GY | 41 |
| Fm-DEVD | Fm-K | D | | B | | DEVDGID | | P | | | K | GY | 42 |
| Fm-DEVN | Fm-K | D | | B | | DEVNGID | | P | | | K | GY | 43 |
| Fm-PARP | Fm-K | D | | B | | EVDGID | | P | | | K | GY | 44 |
| Fm-KNFES | Fm-K | D | | — | | AIPMSI | | P | | | K | GY | 45 |
| | Fm-K | D | | | | AIPNluSI | | P | | | K | GY | 46 |
| Fm-G2D2D | Fm-K | D | | B | | GDEVDGID | G | P | | | K | GY | 47 |
| Fm-CGD2D | Fm-K | D | | B | J | GDEVDGID | GJ | P | | | K | GY | 48 |
| Z-CGD2D | Z-K | D | | B | J | GDEVDGID | GJ | P | | | K | GY | 49 |
| Fm-ICE | Fm-K | DY | | B | | ADGID | | P | | | K | GY | 50 |

TABLE 4

Illustration of the design of the conformation determining regions and protease binding sites in molecules having P domains larger that 4 amino acids. The P1 residue is underlined. Z is benzyloxycarbonyl group, K[TFA] means Lys(N(epsilon)trifluoroacetyl), Fm is Fmoc (preferably attached to the alpha amino group of the amino terminal residue e.,g., Lysine (K). O indicates tetrahydroisoquinoline-3-carboxylic acid. Aib, designated as B, can be replaced by Pro. J is a C

| Substrate class | $aa^1$ | $aa^2$-$aa^3$ | $aa^4$ | $aa^5$ | X | P | Y | $aa^6$ | $aa^7$ | $aa^8$-$aa^9$ | $aa^{10}$ | $S^2$ | SEQ ID NO |
|---|---|---|---|---|---|---|---|---|---|---|---|---|---|
| CPP32 | Fa-K | D | | P | JG | DEVDGIN | GJ | P | | | K | GY | 51 |
| CPP32 | Fm-K | D | | P | JG | DEVDGIN | GJ | P | | | K amide | | 52 |
| CPP32 | Fm-K | D | | P | JG | (d-O)DEVDGIN | GJ | P | | | K | GY | 53 |
| CPP32 | Fm-K | D | | P | JG | DEVDGIN | G | P | | | K | GY | 54 |
| CPP32 | Fm-K | D | | P | G | DEVDGIN | GJ | P | | | K | GY | 55 |
| CPP32 | Fm-K | D | | P | JG | DEVDGID | GJ | P | | | K amide | | 56 |
| CPP32 | Fm-K | D | | P | JG | EEVEGIN | GJ | P | | | K | GY | 57 |
| CPP32 | Fm-K | D | | P | JG | D(dF)VDGIN | GJ | P | | | K | GY | 58 |
| CPP32 | Fm-K | D | | P | JG | (d-D)EV(d-D)GIN | GJ | P | | | K | GY | 59 |
| CPP32 | Fm-K | D | | P | JG | DEVDGIN | GJ | P | | | K | GY | 60 |
| CPP32 | Fm-K | DB | | | JG | DEVNGIN | GJ | P | | | K | GY | 61 |
| CPP32 | Fm-K | DB | | | JG | DEVDGID | GJ | P | | | K | GY | 62 |
| CPP32 | Fm-K | DB | | | JG | DEVDGIN | GJ | P | | | K | GY | 63 |
| CPP32 | Fm-K | DB | | | JG | DEVNGIN | GJ | P | | | K | GY | 64 |
| CPP32 | K | D | | B | JJ | GDEVDGID | JJ | P | | | K | GY | 65 |
| CPP32 | K | D | | B | J | GNEVDGID | GJ | P | | | K | GY | 66 |
| CPP32 | K | D | | B | J | GDEVDGIN | GJ | P | | | K | GY | 67 |
| CPP32 | K | D | | B | J | GNEVDGIN | GJ | P | | | K | GY | 68 |
| CPP32 | K | D | | B | J | GDEVNGIN | GJ | P | | | K | GY | 69 |
| CPP32 | K | D | | B | J | GNEVNGIN | GJ | P | | | K | GY | 70 |
| CPP32 | K | D | | B | JG | ODEVDGID | GJ | P | | | K | GK | 71 |
| CPP32 | K | D | | B | JG | dODEVDGID | GJ | P | | | K | GY | 72 |
| CPP32 | K | D | | B | JG | WDEVDGID | GJ | P | | | K | GY | 73 |
| CPP32 | K | D | | B | JG | dWDEVDGID | GJ | P | | | K | GY | 74 |
| CPP32 | K | D | | B | JG | dOdODEVDGID | GJ | P | | | K | GY | 75 |
| CPP32 | K | D | | B | JG | dWdWDEVDGID | GJ | P | | | K | GY | 76 |
| CPP32 | K | D | | B | | YVADGID | | P | | | K | GY | 77 |
| CPP32 | K | D | | B | | YVADGIN | | P | | | K | GY | 78 |
| CPP32 | K | D | | B | | YVANGIN | | P | | | K | GY | 79 |
| CPP32 | K | D | | B | G | YVADGID | G | P | | | K | GY | 80 |
| CPP32 | K | D | | B | G | YVADGIN | G | P | | | K | GY | 81 |
| CPP32 | K | D | | B | G | YVANGIN | G | P | | | K | GY | 82 |
| CPP32 | K | D | | B | JG | YVADGID | GJ | P | | | K | GY | 83 |
| CPP32 | K | D | | B | JG | YVANGID | GJ | P | | | K | GY | 84 |

TABLE 4-continued

Illustration of the design of the conformation determining regions and protease binding sites in molecules having P domains larger that 4 amino acids. The P1 residue is underlined. Z is benzyloxycarbonyl group, K[TFA] means Lys(N(epsilon)trifluoroacetyl), Fm is Fmoc (preferably attached to the alpha amino group of the amino terminal residue e.g., Lysine (K). O indicates tetrahydroisoquinoline-3-carboxylic acid. Aib, designated as B, can be replaced by Pro. J is a C

| Substrate class | $aa^1$ | $aa^2$-$aa^3$ | $aa^4$ | $aa^5$ | X | P | Y | $aa^6$ | $aa^7$ | $aa^8$-$aa^9$ | $aa^{10}$ | $S^2$ | SEQ ID NO |
|---|---|---|---|---|---|---|---|---|---|---|---|---|---|
| CPP32 | K | D | | B | JG | YVANGIN | GJ | | P | | K | GY | 85 |
| CPP32 | K | D | | B | JG | YVADGIN | GJ | | P | | K | GY | 86 |
| CPP32 | K | D | | B | JG | dYVADGIN | GJ | | P | | K | GY | 87 |
| CPP32 | K | D | | B | | YVHDAPV | | | P | | K | GY | 88 |
| CPP32 | K | D | | B | | YVHDAPV | | | P | | K | GY | 89 |
| CPP32 | K | D | | B | | YVHDAPV | | | P | | K | GY | 90 |
| CPP32 | K | D | | B | G | YVHDAPV | G | | P | | K | GY | 91 |
| CPP32 | K | D | | B | G | YVHDAPV | G | | P | | K | GY | 92 |
| CPP32 | K | D | | B | G | YVHDAPV | G | | P | | K | GY | 93 |
| CPP32 | K | D | | B | JG | YVHDAPV | GJ | | P | | K | GY | 94 |
| CPP32 | K | D | | B | JG | YVHDAPV | GJ | | P | | K | GY | 95 |
| CPP32 | K | D | | B | JG | YVHDAPV | GJ | | P | | K | GY | 96 |
| CPP32 | K | D | | B | JG | YVHDAPV | GJ | | P | | K | GY | 97 |
| CPP32 | K | D | | B | JG | YVHDAPV | GJ | | P | | K | GY | 98 |
| CPP32 | K | D | | B | JG | dYVHDAPV | GJ | | P | | K | GY | 99 |
| Lamin-A | Fm-K | D | | P | JG | LVEIDNG | J | | P | | K | GY | 100 |
| Lamin-A | FM-K | DP | | | JG | LVEIENG | J | | P | | K | GY | 101 |
| Lamin-A | K | D | | B | | LVEIDNG | | | P | | K | GY | 102 |
| Lamin-A | K | D | | B | G | LVEIDNG | G | | P | | K | GY | 103 |
| Lamin-A | K | D | | B | JG | LVEIDNG | GJ | | P | | K | GY | 104 |
| Lamin-A | K | D | | B | JG | LVEINNG | GJ | | P | | K | GY | 105 |
| ProCPP32Asp175 | Fm-K | D | | P | J | GIETESGV | GJ | | P | | K | GY | 106 |
| ProCPP32Asp175 | Fm-K | D | | P | J | GIETDSG | J | | P | | K | GY | 107 |
| ProCPP32Asp175 | Fm-K | D | | P | J | GIETESG | J | | P | | K | GY | 108 |
| ProCPP32Asp175 | K | D | | B | | GIETDSGVDD | | | P | | K | GY | 109 |
| ProCPP32Asp175 | K | D | | B | | GIETNSGVDD | | | P | | K | GY | 110 |
| ProCPP32Asp175 | K | D | | B | G | GIETDSGVDD | G | | P | | K | GY | 111 |
| ProCPP32Asp175 | K | D | | B | G | GIETNSGV | G | | P | | K | GY | 112 |
| ProCPP32Asp175 | K | D | | B | J | GIETDSGV | J | | P | | K | GY | 113 |
| ProCPP32Asp175 | K | D | | B | J | GIETNSGV | J | | P | | K | GY | 114 |
| ProCPP32Asp175 | K | D | | B | JG | GIETDSGV | GJ | | P | | K | GY | 115 |
| ProCPP32Asp175 | K | D | | B | JG | GIETNSGV | GJ | | P | | K | GY | 116 |
| ProCPP32Asp28 | K | D | | B | | GSESMDSGISLD | | | P | | K | GY | 117 |
| ProCPP32Asp28 | K | D | | B | G | GSESMDSG | G | | P | | K | GY | 118 |
| ProCPP32Asp28 | K | D | | B | JG | GSESMDSG | GJ | | P | | K | GY | 119 |
| NS3 NS5A/5B | K | D | | B | JG | DVVCCSMS | GJ | | P | | K | GY | 120 |
| NS3 NS5A/5B | K | D | | B | JG | DVVCDSMS | GJ | | P | | K | GY | 121 |
| NS3 NS5A/5B | K | D | | B | JG | DVVCCSdMS | GJ | | P | | K | GY | 122 |
| NS3 NS5A/5B | K | D | | B | JG | DVVCDSdMS | GJ | | P | | K | GY | 123 |
| NS3 NS5A/5B | K | D | | B | JG | DVVCCPdMS | GJ | | P | | K | GY | 124 |
| NS3 NS5A/5B | K | D | | B | JG | EDVVCCS | GJ | | P | | K | GY | 125 |
| NS3 NS5A/5B | K | D | | B | JG | EDVVCDS | GJ | | P | | K | GY | 126 |
| NS3 NS5A/5B | K | D | | B | JG | EDdVVCCP | GJ | | P | | K | GY | 127 |
| NS3 NS5A/5B | K | D | | B | JG | EDdVVCDP | GJ | | P | | K | GY | 128 |
| NS3 NS5A/5B | K | D | | B | JG | DdVVCCSdMS | GJ | | P | | K | GY | 129 |
| NS3 NS5A/5B | K | D | | B | JG | DVdVCDSdMS | GJ | | P | | K | GY | 130 |
| NS3 NS5A/5B | K | D | | B | JG | DdVVCCPdMS | GJ | | P | | K | GY | 131 |
| NS3 NS5A/5B | K | D | | B | JG | DVVCCSM | GJ | | P | | K | GY | 132 |
| NS3 NS5A/5B | K | D | | B | JG | DVVCDSM | GJ | | P | | K | GY | 133 |
| NS3 NS5A/5B | K | D | | B | JG | VCCSM | GJ | | P | | K | GY | 134 |
| NS3 NS5A/5B | K | D | | B | JG | VCDSM | GJ | | P | | K | GY | 135 |
| NS3 NS4A/4B | K | D | | B | JG | DEMEECSQHL | | | P | | K | GY | 136 |
| NS3 NS4A/4B | K | D | | B | JG | DEMEECPQHL | | | P | | K | GY | 137 |
| NS3 NS4A/4B | K | D | | B | JG | DEMEEDSQHL | | | P | | K | GY | 138 |
| NS3 NS4A/4B | K | D | | B | JG | EMEECSQHL | | | P | | K | GY | 139 |
| NS3 NS4A/4B | K | D | | B | JG | EMEECPQHL | | | P | | K | GY | 140 |
| NS3 NS4A/4B | K | D | | B | JG | EMEEDSQHL | | | P | | K | GY | 141 |
| NS3 NS4A/4B | K | D | | B | JG | EMEECSQHL | G | | P | | K | GY | 142 |
| NS3 NS4A/4B | K | D | | B | JG | EMEECPQHL | G | | P | | K | GY | 143 |
| NS3 NS4A/4B | K | D | | B | JG | EMEEDSQHL | G | | P | | K | GY | 144 |
| NS3 NS4A/4B | K | D | | B | JG | EMEECSQHL | GJ | | P | | K | GY | 145 |
| NS3 NS4A/4B | K | D | | B | JG | EMEECPQHL | GJ | | P | | K | GY | 146 |
| NS3 NS4A/4B | K | D | | B | JG | EMEEDSQHL | GJ | | P | | K | GY | 147 |
| Ext. PAI-2 | K | D | | B | JG | VMTGRTG | J | | P | | K | GY | 148 |
| Ext. PAI-2 | K | D | | B | JG | VdMTGRTG | J | | P | | K | GY | 149 |
| Ext. PAI-2 | K | D | | B | JG | VMTGRTG | J | | P | | K | GY | 150 |
| Ext. PAI-2 | K | D | | B | JG | VMTGRTG | J | | P | | K | GY | 151 |
| Thromb | K | D | | B | JG | VMTGRG | J | | P | | K | GY | 152 |

TABLE 4-continued

Illustration of the design of the conformation determining regions and protease binding sites in molecules having P domains larger that 4 amino acids. The P1 residue is underlined. Z is benzyloxycarbonyl group, K[TFA] means Lys(N(epsilon)trifluoroacetyl), Fm is Fmoc (preferably attached to the alpha amino group of the amino terminal residue e.,g., Lysine (K). O indicates tetrahydroisoquinoline-3-carboxylic acid. Aib, designated as B, can be replaced by Pro. J is a C

| Substrate class | $aa^1$ | $aa^2$-$aa^3$ | $aa^4$ | $aa^5$ | X | P | Y | $aa^6$ | $aa^7$ | $aa^8$-$aa^9$ | $aa^{10}$ | $S^2$ | SEQ ID NO |
|---|---|---|---|---|---|---|---|---|---|---|---|---|---|
| Thromb | K | D | B | JG | VMTGRG | GJ | P | | | | K | GY | 153 |
| Thromb | K | D | B | JG | VdmTGRG | GJ | P | | | | K | GY | 154 |
| Urokinase | Fm-K | D | P | J | TGRT | | | | | | | | 155 |
| Urokinase | | Fm-D | P | | TGRT | G | P | | | | K | GY | 156 |
| Urokinase | Fm-K | D | P | | VMTGRT | GJ | P | | | | K | GY | 157 |
| Urokinase | Fm-K | D | P | | TGRT | GJ | P | | | | K | GY | 158 |
| Urokinase | Fm-K | D | P | JG | TGRT | GJ | P | | | | K | GY | 159 |
| Urokinase | Fm-K | D | P | JG | TGRT | G | P | | | | K | GY | 160 |
| Urokinase | Fm-K | D | P | G | TGRT | G | P | | | | K | GY | 161 |
| Urokinase | K | D | P | J | TGRTG | J | P | | | | K | GY | 162 |
| Urokinase | K | D | P | C3 | TGRTG | | P | | | | K | GY | 163 |
| Urokinase | K | D | P | C7 | TGRTG | | P | | | | K | GY | 164 |
| Urokinase | K | D | B | JG | VMTGRVG | J | P | | | | K | GY | 165 |
| Urokinase | K | D | B | JG | VdMTGRVG | J | P | | | | K | GY | 166 |
| F12A | K | D | B | JG | VMTGRAG | J | P | | | | K | GY | 167 |
| F12A | K | D | B | JG | VdMTGRAG | J | P | | | | K | GY | 168 |
| Swedish KM/NL amyloid | Fm-K | D | P | JG | SEVKLDAEF GC5PKGY | GJ | P | | | | K | GY | 169 |
| Swedish KM/NL amyloid | Fm-K | D | P | JG | S(d-E)VK(d-L) DAE(d-F) | GJ | P | | | | K | GY | 170 |
| Swedish KM/NL amyloid | Fm-K | D | P | JG | S(d-E)VK(d-L) DAE(d-F) | GJ | P | | | | K | GY | 171 |
| Swedish KM/NL amyloid | K | D | B | JG | SEVNLDAEF | GJ | P | | | | K | DDY | 172 |
| Swedish KM/NL amyloid | Fm-K | D | B | JG | SEVNLDAEF | GJ | P | | | | K | DDY | 173 |
| Swedish KM/NL amyloid | K | D | B | JG | SEVKLDAEF | GJ | P | | | | K | DDY | 174 |
| Native Amyloid | K | D | B | JG | SEVKMDAEF | GJ | P | | | | K | DDY | 175 |
| Cathepsin G | K | D | B | JG | SEVKMDDEF | GJ | P | | | | K | DDY | 176 |
| Cathepsin G | K | D | B | JG | SEVNLDDEF | GJ | P | | | | K | DDY | 177 |
| APP[709–710] | K | D | B | JG | GVVIATVIVIT | GJ | P | | | | K | DDY | 178 |
| APP[708–719] | K | D | B | JG | YGVVIATVIVIT | GJ | P | | | | K | DDY | 179 |
| APP[711–716] | K | D | B | JG | VIATVI | GJ | P | | | | K | DDY | 180 |
| APP[708–713] | K | D | B | JB | YGVVIA | GJ | P | | | | K | DDY | 181 |
| PSA Sg1 | K | D | B | JJ | QQLLHN | JJ | P | | | | K | | 182 |
| PSA Sg1 | K | D | B | JG | QQLLHN | GJ | P | | | | K | | 183 |
| PSA Sg1 | K | D | B | G | QQLLHN | G | P | | | | K | | 184 |
| PSA Sg1 | K | D | B | | QQLLHN | | P | | | | K | | 185 |
| PSA Sg2 | K | D | B | JJ | SIQYTY | JJ | P | | | | K | | 186 |
| PSA Sg2 | K | D | B | JG | SIQYTY | GJ | P | | | | K | | 187 |
| PSA Sg2 | K | D | B | G | SIQYTY | G | P | | | | K | | 188 |
| PSA Sg2 | K | D | B | | SIQYTY | | P | | | | K | | 189 |
| PSA Sg3 | K | D | B | JJ | SSQYSN | JJ | P | | | | K | | 190 |
| PSA Sg3 | K | D | B | JG | SSQYSN | GJ | P | | | | K | | 191 |
| PSA Sg3 | K | D | B | G | SSQYSN | G | P | | | | K | | 192 |
| PSA Sg3 | K | D | B | | SSQYSN | | P | | | | K | | 193 |
| PSA Sg4 | K | D | B | JJ | SSIYSQ | JJ | P | | | | K | | 194 |
| PSA Sg4 | K | D | B | JG | SSIYSQ | GJ | P | | | | K | | 195 |
| PSA Sg4 | K | D | B | G | SSIYSQ | G | P | | | | K | | 196 |
| PSA Sg4 | K | D | B | | SSIYSQ | | P | | | | K | | 197 |
| Cathepsin D | Fm-K | D | P | JG | SEVNLDAEF | GJ | P | | | | K | GY | 198 |
| Caspase-9 | Fm-K | D | P | JG | LEHDGIN | GJ | P | | | | K | GY | 199 |
| Caspase-8 | Fm-K | D | P | JG | LETDGIN | GJ | P | | | | K | GY | 200 |
| Caspase-1 | Fm-K | D | P | JG | WEHDGIN | GJ | P | | | | K | GY | 201 |
| Caspase-1 | Fm-K | D | P | JG | YVHDG | J | P | | | | K | GY | 202 |
| Caspase-1 | Fm-K | D | P | JG | YVHDGIN | GJ | P | | | | K | GY | 203 |
| Caspase-1 | Fm-K | D | P | JG | YVHDAPV | GJ | P | | | | K | GY | 204 |
| Caspase-1 | Fm-K | D | P | JG | YVHDAPV | | P | | | | K | GY | 205 |
| Caspase-1 | Fm-K | D | P | | YVHDAPV | GJ | P | | | | K | GY | 206 |
| Caspase-1 | Fm-K | D | P | JG | YVHDA | | P | | | | K | GY | 207 |
| Granzyme B | Fm-K | DP | | JG | IEPDS | GJ | P | | | | K | GY | 208 |
| Collagenase | Fm-K | DP | | JG | PLGIAGI | GJ | P | | | | K | GY | 209 |

TABLE 4-continued

Illustration of the design of the conformation determining regions and protease binding sites in molecules having P domains larger that 4 amino acids. The P1 residue is underlined. Z is benzyloxycarbonyl group, K[TFA] means Lys(N(epsilon)trifluoroacetyl), Fm is Fmoc (preferably attached to the alpha amino group of the amino terminal residue e.,g., Lysine (K). O indicates tetrahydroisoquinoline-3-carboxylic acid. Aib, designated as B, can be replaced by Pro. J is a C

| Substrate class | $aa^1$ | $aa^2$-$aa^3$ | $aa^4$ | $aa^5$ | X | P | Y | $aa^6$ | $aa^7$ | $aa^8$-$aa^9$ | $aa^{10}$ | $S^2$ | SEQ ID NO |
|---|---|---|---|---|---|---|---|---|---|---|---|---|---|
| HIV-1 protease | Fm-K | DP | | | JG | SQNYPIVQ | GJ | P | | | K | GY | 210 |
| Hepatitis C protease | Fa-K | DP | | | JG | EDVVCCS | GJ | P | | | K | GY | 211 |

* In certain embodiments, the Fm or Fa groups identified in the above sequences are optional or can be substituted with other hydrophobic groups. Conversely any of the sequences listed without a hydrophobic group can have one added. In addition, in certain embodiments, the carboxyl terminal amino acid can have the carboxylic acid group replaced with an amide.

IV. Fluorophores

A fluorophore excited by incident radiation absorbs light and then subsequently re-emits that light at a different (longer) wavelength. However, in the presence of a second class of molecules, known as "acceptors" the light emitted by a so-called donor fluorophore is absorbed by the acceptor thereby quenching the fluorescence signal of the donor. Thus, use of two fluorophores, as opposed to a fluorophore/chomophore pair, allows a clearer assessment of the overlap between the emission spectrum of the donor and the excitation spectrum of the acceptor. This facilitates the design of a peptide backbone that allows optimization of the quenching. This results in a high efficiency donor/acceptor pair facilitating the detection of low concentrations of protease activity. Thus, although a fluorophore/chromophore combination can be suitable, in certain preferred embodiments, the fluorogenic protease inhibitors of this invention will comprise two fluorophores.

The "donor" and "acceptor" molecules are typically selected as a matched pair such that the absorption spectrum of the acceptor molecule overlaps the emission spectrum of the donor molecule as much as possible. In addition, the donor and acceptor fluorophores are preferably selected such that both the absorption and the emission spectrum of the donor molecule are in the visible range (400 nm to about 700 nm). The fluorophores thereby provide a signal that is detectable in a biological sample thus facilitating the detection of protease activity in biological fluids, tissue homogenates, in situ in tissue sections, cultured or freshly isolated cells, and the like. The emission spectra, absorption spectra and chemical composition of many fluorophores are well known to those of skill in the art (see, for example, *Handbook of Fluorescent Probes and Research Chemicals*, R. P. Haugland, ed. which is incorporated herein by reference).

Preferred fluorophore pairs include, but are not limited to the rhodamine derivatives. Thus, for example 5- and/or 6-carboxytetramethylrhodamine or the succinimidyl ester of 5- and/or 6-carboxytetramethylrhodamine (9-(2,5-dicarboxyphenyl)-3,6-bis-(dimethylamino)xanthylium chloride (5-TMR) and 9-(2,6-dicarboxyphenyl)-3,6-bis-(dimethylamino)xanthylium chloride (6-TMR)), (C2211 is the succinimidyl ester of 5-TMR and C1171 is the isomeric mixture of the succinimidyl esters of 5-TMR and 6-TMR respectively, available from Molecular Probes, Eugene, Oreg., USA) (Formula VI is 5-TMR) is one particularly preferred donor molecule

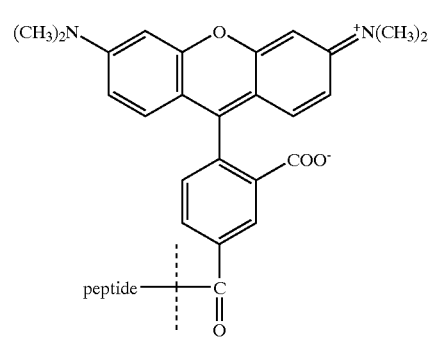

and carboxyrhodamine X acetamide (R 492 from Molecular Probes) (Formula VII)

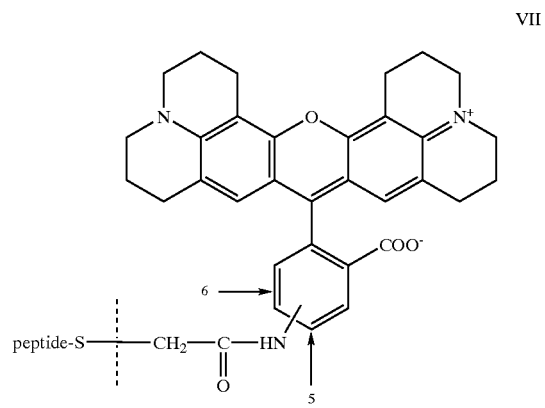

or the succinimidyl ester of 5- and/or 6-carboxy-X-rhodamine [9-(2,5-dicarboxyphenyl)-2,7-dimethyl-3,6-bis(ethylamino)xanthene (5-DER) and 9-(2,6-dicarboxyphenyl)-2,7-dimethyl-3,6-bis(ethylamino)xanthene (6-DER), mixed isomer available as C1309 (designated herein as DER) from Molecular Probes] is one particularly preferred acceptor molecule. The excitation and emission of both members of this donor/acceptor pair are in the visible wavelengths, the molecules have high extinction coefficients, and the molecules have high fluorescence yields in solution. The extinction coefficient is a measure of the light absorbance at a particular wavelength by the chromophore and is therefore related to its ability to quench a signal, while the fluorescence yield is the ratio of light absorbed to light re-emitted and is a measure of the efficiency of fluorescence of the fluorophore and thus effects the sensitivity of the protease indicator.

Other preferred fluorophores include, but are not limited to rhodamine 110 (Molecular Probes), rhodamine X, 9-(2,5 (or 2,6)-dicarboxyphenyl)-3,6-bis(dimethylamino) xanthyliumhalide or other anion (TMR), 9-(2,5)-dicarboxyphenyl)-2,7-dimethyl-3,6-bis(ethylamino) xanthylium halide or other anion (Rh6G), 9-(2,6)-dicarboxyphenyl)-2,7-dimethyl-3,6-bis(ethylamino) xanthylium halide or other anion, 9-(2,5(or 2,6)-dicarboxyphenyl)-3,6-bisamino-xanthylium halide or other anion (Rh110), 9-(2,5(or 2,6)-dicarboxyphenyl)-3-amino-6-hydroxy-xanthylium halide or other anion (Blue Rh), 9-(2-carboxyphenyl)-2,7-dimethyl-3,6-bis(ethylamino) xanthylium, 9-(2-carboxyphenyl)-3,6-bis(dimethylamino) xanthylium, and 9-(2-carboxyphenyl)-xanthylium.

In one particularly preferred embodiment a peptide backbone will have two amino acid side chain amino groups or two sulfhydryl groups, or one amino plus one sulfhydryl group, on either side of a cleavage site available for covalent bond formation resulting from interaction with fluorophores containing succinimidyl and/or maleimidyl and/or iodoacetamidyl groups where the fluorophore to peptide ratio is ca. 3:1 in the reaction mixture enabling the product to contain 2 fluorophores per peptide backbone.

In certain embodiments, fluorophores that absorb and emit in the ultraviolet may also be used in the protease indicators of the present invention. One particularly preferred ultraviolet absorbing pair of fluorophores is 7-hydroxy-4-methylcoumarin-3-acetic acid as the donor molecule (Formula VIII)

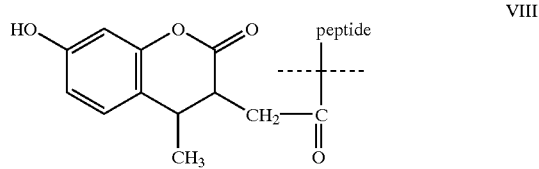

and 7-diethylamino-3-((4'-iodoacetyl)amino)phenyl)-4-methylcoumarin (Formula IX) as the acceptor molecule.

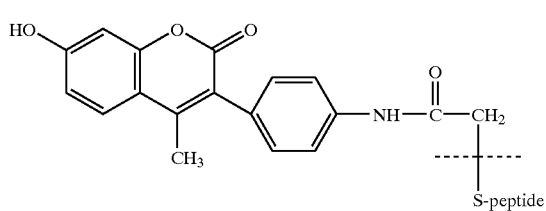

These and other fluorophores are commercially available from a large number of manufacturers such as Molecular Probes (Eugene, Oreg., USA).

It was a surprising discovery that fluorophores having matched absorption and emission spectra are not required in the practice of the present invention. In fact, a single species of fluorophore, when joined to the polypeptide backbones of this invention in the positions occupied by $F^1$ and $F^2$, is capable of quenching itself. Moreover, this quenching is fully released when the peptide backbone is cleaved.

Without being bound to a particular theory, it is believed that quenching is accomplished by the formation of ground state dimers wherein the fluorescence of the dimer is largely quenched. It is the limited conformational entropy of the peptide backbones of this invention that forces fluorophores into close enough proximity to effectively form a ground state dimer.

Particularly preferred molecules form H-type dimers. The formation of H-type dimers by fluorescent molecules is described by Packard et al. (1996) Proc. Natl. Acad. Sci. USA, 93: 11640–11645; Packard et al. (1997) J. Phys. Chem. B, 101: 5070–5074. The H-type dimer is characterized by exciton bands in the absorption spectra and fluorescence quenching (see, e.g., Valdes-Aguilera et al. (1989) Acc. Chem. Res., 22: 171–177 and Packard et al. (1996) Proc. Natl. Acad. Sci. USA, 93: 11640–11645).

Thus, in a preferred embodiment, the protease indicators of this invention include only a single species of fluorophore, more preferably a fluorophore capable of forming H-type dimers.

NorFes is an undecapeptide that contains a recognition sequence and cleavage site for the serine protease elastase. When NorFes was doubly labeled with a variety of fluorophores on opposite sites of the amino acid sequence, the fluorescence was quenched due to formation of intramolecular ground-state dimers. The spectral characteristics of these dimers were predictable by exciton theory.

The decrease in dimer/monomer ratios as the temperature was raised indicated an intermolecular attraction between the dye molecules. The free energy of activation of disruption of homodimers composed of tetramethylrhodamine was at least 1.7 kcal/mole and for those of diethylrhodamine was 2.4 kcal/mnole (Packard et al. (1998) J. Phys. Chem. 102:1820–1827). Because of the intermolecular attraction of fluorophores that form exciton dimers the connecting amino acid sequences can deviate from the optimal sequences described herein. Thus, when exciton-forming fluorophores are used, amino acid substitutions can be made in the "backbones" described herein and activity can still be maintained.

Particularly preferred exciton-forming fluorophores include, but are not limited to carboxytetramethylrhodamine, carboxyrhodamine-X, carboxyrhodamine 110, diethylaminocoumarin, and carbocyanine dyes. In this embodiment, there is no need to match emission or absorption spectra since only a single fluorophore is used. Thus a wide variety of fluorophores can be used effectively. In addition, the use of a single fluorophore greatly simplifies synthetic chemistry and simplifies detection.

Figure 6:
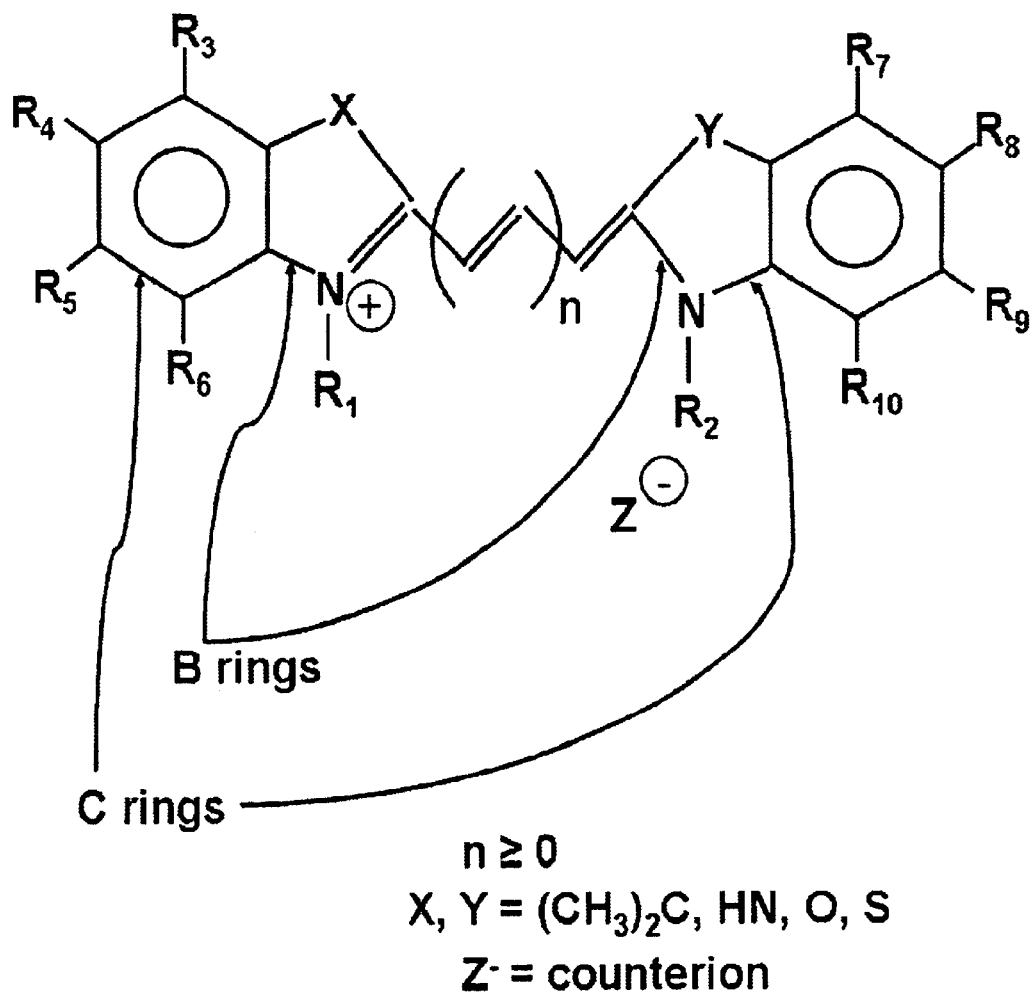
FIG. 6. Preferred dialkylated carbocyanine dyes for use in the methods of this invention. X and Y are independently selected from the group consisting of $(CH_3)_2C$, NH, O, S, and the like. N is preferably greater than or equal to zero. Preferably n is greater than zero and less than 20, more preferably N is greater than zero and less than 10, and most preferably n is greater than zero and less than about 5. In certain embodiments n is one or two. $R^1$ and $R^2$ are independently selected alkyl groups. $R^3$ through $R^{10}$ are independently selected from the group consisting of H, alkyl, O alkyl, alhalide, alkylated amines, amines, and the like. Z is any counterion (e.g., a halide, a perchlorate, etc.) In IC5 $R^1$ is ethyl and $R^2$ is 5-(N"-carbonylpentyl). $R^3$ through $R^{10}$ are H, X and Y are 3,3,3',3'-tetramethyl (see, e.g., IC5-OSu from Dojindo Laboratories, Inc).

The use of homo-doubly labeled indicators (indicators doubly labeled with a single species of fluorophore) of this invention also permits detection of enzymatic activity by absorbance measurements in addition to fluorescence measurements. Since blue-shifted exciton bands (or blue-shifted absorption maxima or shoulders) in absorption spectra denote H-dimer formation and fluorescence quenching is concomitant with the latter, measurement of absorption spectra may be sufficient as a diagnostic tool in the proper setting. When a doubly labeled protease indicator is cleaved by a specific protease, the H-type dimer is disrupted. The blue shifted absorption maximum, or shoulders, associated with the H-type dimer is then lost. Hence, if one measures the intensity of absorption at this blue shifted exciton band then as the H-type dimer is disrupted the absorption intensity is expected to decrease whereas the absorption intensity at the monomer maximum peak wavelength is expected to increase, i.e., the wavelength of the absorption peak is increased or the blue shoulder decreases such that the average wavelength of the band is increased Preferred for use in certain high throughput screening systems are indicators of this invention formulated with rhodamine or cyanine dyes, including cyanines and cyanine analogues. Particular preferred embodiments utilize carbocyanine dyes, more preferably dialkylated carbocyanine dyes, e.g. as illustrated in FIG. 6. Suitable cyanine dyes include, but are not limited to N-ethyl-N'-[5-(N"-succinimidyloxycarbonyl)pentyl]indocarbocyanine chloride, and N-ethyl-N'-[5-(N"-carbonyl)pentyl]-3,3,3',3-tetramethyl-2,2'-indodicarbocyanine chloride.

V. Preparation of Fluorogenic Protease Indicators

The fluorogenic protease indicators of the present invention are preferably prepared by first synthesizing the peptide backbone, i.e. the protease cleavage site (P), the two conformation determining regions ($C^1$ and $C^2$), and the spacers ($S^1$ and $S^2$) if present. The fluorophores are then chemically conjugated to the peptide. The fluorophores are preferably conjugated directly to the peptide however, they may also be coupled to the peptide through a linker. Finally, where the fluorogenic protease indicator is to be bound to a solid support, it is then chemically conjugated to the solid support via the spacer ($S^1$ or $S^2$) either directly or through a linker.

A) Preparation of the Peptide Backbone

Solid phase peptide synthesis in which the C-terminal amino acid of the sequence is attached to an insoluble support followed by sequential addition of the remaining amino acids in the sequence is the preferred method for preparing the peptide backbone of the compounds of the present invention. Techniques for solid phase synthesis are described by Barany and Merrifield, *Solid-Phase Peptide Synthesis*; pp. 3–284 in *The Peptides: Analysis, Synthesis, Biology. Vol. 2: Special Methods in Peptide Synthesis, Part a.*, Merrifield, et al. *J. Am. Chem. Soc.* 85, 2149–2156 (1963), and Gross and Meienhofer, eds. Academic press, N.Y., 1980 and Stewart et al., *Solid Phase Peptide Synthesis*, 2nd ed. Pierce Chem. Co., Rockford, Ill. (1984) which are incorporated herein by reference. Solid phase synthesis is most easily accomplished with commercially available peptide synthesizers utilizing FMOC or TBOC chemistry. The chemical synthesis of the peptide component of a fluorogenic protease indicator is described in detail in Examples 1 and 2.

In a particularly preferred embodiment, peptide synthesis is performed using Fmoc synthesis chemistry. The side chains of Asp, Ser, Thr and Tyr are preferably protected using t-Butyl and the side chain of Cys residue using S-trityl and S-t-butylthio, and Lys residues are preferably protected using t-Boc, Fmoc and 4-methyltrityl for lysine residues. Appropriately protected amino acid reagents are commercially available. The use of multiple protecting groups allows selective deblocking and coupling of a fluorophore to any particular desired side chain. Thus, for example, t-Boc deprotection is accomplished using TFA in dichloromethane, Fmoc deprotection is accomplished using 20% (v/v) piperidine in DMF or N-methylpyrolidone, and 4-methyltrityl deprotection is accomplished using 1 to 5% (v/v) TFA in water or 1% TFA and 5% triisopropylsilane in DCM, S-t-butylthio deprotection is accomplished in aqueous mercaptoethanol (10%), t-butyl and t-boc and S-trityl deprotection is accomplished using TFA:phenol:water:thioanisol:ethanedithiol (85:5:5:2.5:2.5), and t-butyl and t-Boc deprotection is accomplished using TFA:phenol:water (95:5:5). Detailed synthesis, deprotection and fluorophore coupling protocols are provided in Examples 1 and 2.

Alternatively, the peptide components of the fluorogenic protease indicators of the present invention may be synthesized utilizing recombinant DNA technology. Briefly, a DNA molecule encoding the desired amino acid sequence is synthesized chemically by a variety of methods known to those of skill in the art including the solid phase phosphoramidite method described by Beaucage and Carruthers, *Tetra. Letts.* 22: 1859–1862 (1981), the triester method according to Matteucci, et al., *J. Am. Chem. Soc.,* 103:3185 (1981), both incorporated herein by reference, or by other methods known to those of skill in the art. It is preferred that the DNA be synthesized using standard β-cyanoethyl phosphoramidites on a commercially available DNA synthesizer using standard protocols.

The oligonucleotides may be purified, if necessary, by techniques well known to those of skill in the art. Typical purification methods include, but are not limited to gel electrophoresis, anion exchange chromatography (e.g. Mono-Q column, Pharmacia-LKB, Piscataway, N.J., USA), or reverse phase high performance liquid chromatography (HPLC). Method of protein and peptide purification are well known to those of skill in the art. For a review of standard techniques see, *Methods in Enzymology Volume 182: Guide to Protein Purification*, M. Deutscher, ed. (1990), pages 619–626, which are incorporated herein by reference.

The oligonucleotides may be converted into double stranded DNA either by annealing with a complementary oligonucleotide or by polymerization with a DNA polymerase. The DNA may then be inserted into a vector under the control of a promoter and used to transform a host cell so that the cell expresses the encoded peptide sequence. Methods of cloning and expression of peptides are well known to those of skill in the art. See, for example, Sambrook, et al., *Molecular Cloning: a Laboratory Manual* (2nd Ed., Vols. 1–3, Cold Spring Harbor Laboratory (1989)), *Methods in Enzymology*, Vol. 152: *Guide to Molecular Cloning Techniques* (Berger and Kimmel (eds.), San Diego: Academic Press, Inc. (1987)), or *Current Protocols in Molecular Biology*, (Ausubel, et al. (eds.), Greene Publishing and Wiley-Interscience, New York (1987), which are incorporated herein by reference.

B) Linkage of the Fluorophores to the Peptide Backbone

The fluorophores are linked to the peptide backbone by any of a number of means well known to those of skill in the art. In a preferred embodiment, the fluorophore is linked directly from a reactive site on the fluorophore to a reactive group on the peptide such as a terminal amino or carboxyl group, or to a reactive group on an amino acid side chain such as a sulfur, an amino, a hydroxyl, or a carboxyl moiety. Many fluorophores normally contain suitable reactive sites. Alternatively, the fluorophores may be derivatized to provide reactive sites for linkage to another molecule. Fluorophores derivatized with functional groups for coupling to a second molecule are commercially available from a variety of manufacturers. The derivatization may be by a simple substitution of a group on the fluorophore itself, or may be by conjugation to a linker. Various linkers are well known to those of skill in the art and are discussed below. The fluorophores may also be covalently linked to the peptide prior to its cleavage off of the solid support.

As indicated above, in a preferred embodiment, the fluorophores are directly linked to the peptide backbone of the protease indicator. Thus, for example, the 5'-carboxytetramethylrhodamine (5-TMR) fluorophore may be linked to aspartic acid via the alpha amino group of the amino acid as shown in Formula V. The iodoacetamide group of rhodamine X acetamide (R492)) may be linked by reaction with the sulfhydryl group of a cysteine as indicated in formula VI. Means of performing such couplings are well known to those of skill in the art, and the details of one such coupling are provided in Example 1.

One of skill in the art will appreciate that when the peptide spacers ($S^1$ or $S^2$) are present (as is discussed below), the fluorophores are preferably linked to the conformation determining regions through a reactive group on the side chain of the terminal amino acid of $C^1$ or $C^2$ as the spacers themselves form a peptide linkage with the terminal amino and carboxyl groups of $C^1$ or $C^2$ respectively.

C) Selection of Spacer Peptides and Linkage to a Solid Support

The fluorogenic protease indicators of the present invention may be obtained in solution or linked to a solid support. A "solid support" refers to any solid material that does not dissolve in or react with any of the components present in the solutions utilized for assaying for protease activity using the fluorogenic protease indicator molecules of the present invention and that provides a functional group for attachment of the fluorogenic molecule. Solid support materials are well known to those of skill in the art and include, but are not limited to silica, controlled pore glass (CPG), polystyrene, polystyrene/latex, carboxyl modified teflon, dextran, derivatized polysaccharides such as agar bearing amino, carboxyl or sulfhydryl groups, various plastics such as polyethylene, acrylic, and the like. Also of use are "semi-solid" supports such as lipid membranes as found in cells and in liposomes. One of skill will appreciate that the solid supports may be derivatized with functional groups (e.g. hydroxyls, amines, carboxyls, esters, and sulfhydryls) to provide reactive sites for the attachment of linkers or the direct attachment of the peptide.

The fluorogenic protease indicators may be linked to a solid support directly through the fluorophores or through the peptide backbone comprising the indicator. Linkage through the peptide backbone is most preferred.

When it is desired to link the indicator to a solid support through the peptide backbone, the peptide backbone may comprise an additional peptide spacer (designated $S^1$ or $S^2$ in Formula I). The spacer may be present at either the amino or carboxyl terminus of the peptide backbone and may vary from about 1 to about 50 amino acids, more preferably from 1 to about 20 and most preferably from 1 to about 10 amino acids in length. Particularly preferred spacers include Asp-Gly-Ser-Gly-Gly-Gly-Glu-Asp-Glu-Lys (SEQ ID NO:243), Lys-Glu-Asp-Gly-Gly-Asp-Lys (SEQ ID NO:244), Asp-Gly-Ser-Gly-Glu-Asp-Glu-Lys (SEQ ID NO:245), and Lys-Glu-Asp-Glu-Gly-Ser-Gly-Asp-Lys (SEQ ID NO:246).

The amino acid composition of the peptide spacer is not critical as the spacer just serves to separate the active components of the molecule from the substrate thereby preventing undesired interactions. However, the amino acid composition of the spacer may be selected to provide amino acids (e.g. a cysteine or a lysine) having side chains to which a linker or the solid support itself, is easily coupled. Alternatively the linker or the solid support itself may be attached to the amino terminus of $S^1$ or the carboxyl terminus of $S^2$. In a preferred embodiment, the peptide spacer is actually joined to the solid support by a linker. The term "linker", as used herein, refers to a molecule that may be used to link a peptide to another molecule, (e.g. a solid support, fluorophore, etc.). a linker is a hetero or homobifunctional molecule that provides a first reactive site capable of forming a covalent linkage with the peptide and a second reactive site capable of forming a covalent linkage with a reactive group on the solid support. The covalent linkage with the peptide (spacer) may be via either the terminal carboxyl or amino groups or with reactive groups on the amino acid side-chain (e.g. through a disulfide linkage to a cysteine).

Suitable linkers are well known to those of skill in the art and include, but are not limited to, straight or branched-chain carbon linkers, heterocyclic carbon linkers, or peptide linkers. As indicated above, the linkers may be joined to the carboxyl and amino terminal amino acids through their terminal carboxyl or amino groups or through their reactive side-chain groups.

Particularly preferred linkers are capable of forming covalent bonds to amino groups, carboxyl groups, or sulfhydryl. Amino-binding linkers include reactive groups such as carboxyl groups, isocyanates, isothiocyanates, esters, haloalkyls, and the like. Carboxyl-binding linkers are capable of forming include reactive groups such as various amines, hydroxyls and the like. Finally, sulfhydryl-binding linkers include reactive groups such as sulfhydryl groups, acrylates, isothiocyanates, isocyanates and the like. Particularly preferred linkers include sulfoMBS (m-maleimidobenzoyl-N-hydroxysulfosuccinimide ester) for linking amino groups (e.g. an amino group found on a lysine residue in the peptide) with sulfhydryl groups found on the solid support, or vice versa, for linking sulfhydryl groups (e.g. found on a cysteine residue of the peptide) with amino groups found on the solid support. Other particularly preferred linkers include EDC (1-ethyl-3-(3-dimethylaminopropryl)-carbodiimide) and bis-(sulfosuccinimidyl suberate). Other suitable linkers are well known to those of skill in the art.

The fluorogenic compounds of the present invention may be linked to the solid support through either the $S^1$ or the $S^2$ spacer such that the donor fluorophore is either retained on the solid support after cleavage of the molecule by a protease or such that the donor fluorophore goes into solution after cleavage. In the former case, the substrate is then assayed for fluorescence to detect protease activity, while in the later case the solution is assayed for fluorescence to detect protease activity.

VI. Detection of Protease Activity

The present invention also provides methods for utilizing the fluorogenic protease indicators to detect protease activity in a variety of contexts. Thus, in one embodiment, the present invention provides for a method of using the fluorogenic indicators to verify or quantify the protease activity of a stock solution of a protease used for experimental or industrial purposes. Verification of protease activity of stock protease solutions before use is generally recommended as proteases often lose activity over time (e.g. through self-hydrolysis) or to show varying degrees of activation when activated from zymogen precursors.

Assaying for protease activity of a stock solution simply requires adding a quantity of the stock solution to a fluorogenic protease indicator of the present invention and measuring the subsequent increase in fluorescence or decrease in exciton band in the absorption spectrum. The stock solution and the fluorogenic indicator may also be combined and assayed in a "digestion buffer" that optimizes activity of the protease. Buffers suitable for assaying protease activity are well known to those of skill in the art. In general, a buffer will be selected whose pH corresponds to the pH optimum of the particular protease. For example, a buffer particularly suitable for assaying elastase activity consists of 50 mM sodium phosphate, 1 mM EDTA at pH 8.9. The measurement is most easily made in a fluorometer, and instrument that provides an "excitation" light source for the fluorophore and then measures the light subsequently emitted at a particular wavelength. Comparison with a control indicator solution lacking the protease provides a measure of the protease activity. The activity level may be precisely quantified by generating a standard curve for the protease/indicator combination in which the rate of change in fluorescence produced by protease solutions of known activity is determined.

While detection of the fluorogenic compounds is preferably accomplished using a fluorometer, detection may by a variety of other methods well known to those of skill in the art. Thus for example, since the fluorophores of the present invention emit in the visible wavelengths, detection may be simply by visual inspection of fluorescence in response to excitation by a light source. Detection may also be by means of an image analysis system utilizing a video camera interfaced to a digitizer or another image acquisition system. Detection may also be by visualization through a filter as under a fluorescence microscope. The microscope may just provide a signal that is visualized by the operator. However the signal may be recorded on photographic film or using a video analysis system. The signal may also simply be quantified in real-time using either an image analysis system or simply a photometer.

Thus, for example, a basic assay for protease activity of a sample will involve suspending or dissolving the sample in a buffer (at the pH optimum of the particular protease being assayed), adding to the buffer one of the fluorogenic protease indicators of the present invention, and monitoring the resulting change in fluorescence using a spectrofluorometer. The spectrofluorometer will be set to excite the donor fluorophore at the excitation wavelength of the donor fluorophore and to detect the resulting fluorescence at the emission wavelength of the donor fluorophore.

In another embodiment, the protease activity indicators of the present invention may be utilized for detection of protease activity in biological samples. Thus, in a preferred embodiment, this invention provides for methods of detecting protease activity in isolated biological samples such as sputum, blood, blood cells, tumor biopsies, and the like, or in situ, in cells or tissues in culture, or in section where the section is embedded and unfixed. The signal may be quantified using a fluorescence microscope, a fluorescence microplate reader, a fluorometer, or a flow cytometer.

A) Ex vivo Assays of Isolated Biological Samples

In one embodiment, the present invention provides for methods of detecting protease activity in a biological sample. This may be determined by simply contacting the sample with a fluorogenic protease indicator of the present invention and monitoring the change in fluorescence of the indicator over time. The sample may be suspended in a "digestion buffer" as described above. The sample may also be cleared of cellular debris, e.g. by centrifugation before analysis.

Where the fluorogenic protease indicator is bound to a solid support the assay may involve contacting the solid support bearing the indicator to the sample solution. Where the indicator is joined to the solid support by the side of the molecule bearing the donor fluorophore, the fluorescence of the support resulting from digestion of the indicator will then be monitored over time by any of the means described above. Conversely, where the acceptor molecule fluorophore is bound to a solid support, the test solution may be passed over the solid support and then the resulting luminescence of the test solution (due to the cleaved fluorophore) is measured. The donor and acceptor pair may be substituted with the same fluorophore on both the solid support and in the solution. This latter approach may be particularly suitable for high throughput automated assays.

B) In situ Assays of Histological Sections.

In another embodiment, this invention provides for a method of detecting in situ protease activity in histological sections. This method of detecting protease activity in tissues offers significant advantages over prior art methods (e.g. specific stains, antibody labels, etc.) because, unlike simple labeling approaches, in situ assays using the protease indicators indicate actual activity rather than simple presence or absence of the protease. Proteases are often present in tissues in their inactive precursor (zymogen) forms which are capable of binding protease labels. Thus traditional labeling approaches provide no information regarding the physiological state, vis a vis protease activity, of the tissue.

The in situ assay method generally comprises providing a tissue section (preferably a frozen section), contacting the section with one of the fluorogenic protease indicators of the present invention, and visualizing the resulting fluorescence. Visualization is preferably accomplished utilizing a fluorescence microscope. The fluorescence microscope provides an "excitation" light source to induce fluorescence of the "donor" fluorophore. The microscope is typically equipped with filters to optimize detection of the resulting fluorescence. Thus, for example, for the fluorogenic protease indicators described in Example 1, a typical filter cube for a Nikon microscope would contain an excitation filter ($\lambda=550\pm12$ nm), a dichroic mirror ($\lambda=580$ nm) and an interference-emission filter ($\lambda=580\pm10$ nm). As indicated above, the microscope may be equipped with a camera, photometer, or image acquisition system.

The sections are preferably cut as frozen sections as fixation or embedding will destroy protease activity in the sample.

The fluorogenic indicator may be introduced to the sections in a number of ways. For example, the fluorogenic protease indicator may be provided in a buffer solution, as described above, which is applied to the tissue section. Alternatively, the fluorogenic protease indicator may be provided as a semi-solid medium such as a gel or agar which is spread over the tissue sample. The gel helps to hold moisture in the sample while providing a signal in response to protease activity. The fluorogenic protease indicator may also be provided conjugated to a polymer such as a plastic film which may be used in procedures similar to the development of Western Blots. The plastic film is placed over the tissue sample on the slide and the fluorescence resulting from cleaved indicator molecules is viewed in the sample tissue under a microscope.

Typically, the tissue sample must be incubated for a period of time to allow the endogenous proteases to cleave the fluorogenic protease indicators. Incubation times will range from about 10 to 60 minutes at temperatures up to and including 37° C.

C) In situ Assays of Cells in Culture and Cell Suspensions Derived from Tissues and Biopsy Samples.

In yet another embodiment, this invention provides for a method of detecting in situ protease activity of cells in culture, cell suspensions, or adherent cell layers where the cells are derived from one or more biological samples (e.g. derived from tissues, biopsy samples, or biological fluids such as saliva, blood, urine, lymph, plasma, etc.). In preferred embodiments, the cultured cells are grown either in suspension or adherent culture and can be to histology slides for visualization, e.g., by cytocentrifugation.

In one preferred embodiment, slide preparations are washed with phosphate buffered saline and coated with a semi-solid polymer or a solution containing the fluorogenic protease indicator. The slide is incubated at 37° C. for the time necessary for the endogenous proteases to cleave the protease indicator. The slide is then examined, e.g., under a fluorescence microscope equipped with the appropriate filters as described above.

In another preferred embodiment, the cells are incubated with the protease indications at 37° C., then washed with buffer and transferred to a glass capillary tube and examined under a fluorescence microscope or viewed directly (without washing) by fluorescence microscopy. When a flow cytometer is used to quantitate the intracellular enzyme activity, the cells with the fluorogenic indicator can be simply diluted with buffer after 37° C. incubation and analyzed.

VII. Screening for Modulators of Protease Activity.

In certain preferred embodiments, this invention provides methods of screening for modulators of protease activity. A modulator of protease activity is an agent (e.g. compound) that increases, decreases, or eliminates the activity of a protease or that increases, decreases or eliminates the availability of a protease at a particular site (e.g. in a particular cell or location in a cell). The modulator of protease activity can act directly on the protease or it can act indirectly, for example, by altering availability or activity of enzymes that activate the subject protease.

In a preferred embodiment, the methods basically involve contacting the "subject" protease or a cell containing the subject protease with one or more test agents. The protease, or cell is also contacted with one or more of the indicator compounds of this invention. A difference in signal produced by the indicator compound in the presence of the test agent as compared to the signal produced where the test agent has been used as a lower concentration or where no test agent is used indicates that the test agent modulates the activity of the protease.

The assays of this invention are typically scored as positive where there is a difference between the activity seen with the test agent present or where the test agent has been previously applied, and the (usually negative) control, preferably where the difference is statistically significant (e.g. at greater than 80%, preferably greater than about 90%, more preferably greater than about 98%, and most preferably greater than about 99% confidence level). Most preferred "positive" assays show at least a 1.2 fold, preferably at least a 1.5 fold, more preferably at least a 2 fold, and most preferably at least a 4 fold or even a 10-fold difference from the negative control.

The assays can be run in vitro with the protease(s) in question and one or more indicator compounds of this invention in an appropriate buffer system. The test agent can be added to the buffer system and a change in indicator signal can be detected. In addition, or alternatively, the "test" assay can simply be compared to the same system lacking the test agent (a negative control) assay.

The assays can also be run in vivo in cells in culture, in tissues in culture, or in cells/tissues in an organism. One or more cell-permeable indicators of this invention are introduced into the subject cells. The cells, tissues, or organisms are contacted with one or more test agents and the change in indicator signal brought about by the test agent(s) are detected as described herein.

A) Test Agents.

Virtually any agent can be screened according to the methods of this invention. Such agents include, but are not limited to nucleic acids, proteins, sugars, polysaccharides, glycoproteins, lipids, and small organic molecules. The term small organic molecules typically refers to molecules of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da.

Conventionally, new chemical entities with useful properties are generated by identifying a chemical compound (called a "lead compound") with some desirable property or activity, creating variants of the lead compound, and evaluating the property and activity of those variant compounds. However, the current trend is to shorten the time scale for all aspects of drug discovery. Because of the ability to test large numbers quickly and efficiently, high throughput screening (HTS) methods are replacing conventional lead compound identification methods.

In one preferred embodiment, high throughput screening methods involve providing a library containing a large number of potential therapeutic compounds (candidate compounds). Such "combinatorial chemical libraries" are then screened in one or more assays, as described herein to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis by combining a number of chemical "building blocks" such as reagents. For example, a linear combinatorial chemical library such as a polypeptide (e.g., mutein) library is formed by combining a set of chemical building blocks called amino acids in every possible way for a given compound length (i.e., the number of amino acids in a polypeptide compound). Millions of chemical compounds can be synthesized through such combinatorial mixing of chemical building blocks. For example, one commentator has observed that the systematic, combinatorial mixing of 100 interchangeable chemical building blocks results in the theoretical synthesis of 100 million tetrameric compounds or 10 billion pentameric compounds (Gallop et al. (1994) 37(9): 1233–1250).

Preparation of combinatorial chemical libraries is well known to those of skill in the art. Such combinatorial chemical libraries include, but are not limited to, peptide libraries (see, e.g., U.S. Pat. No. 5,010,175, Furka (1991) *Int. J. Pept. Prot. Res.*, 37: 487–493, Houghton et al. (1991) *Nature*, 354: 84–88). Peptide synthesis is by no means the only approach envisioned and intended for use with the present invention. Other chemistries for generating chemical diversity libraries can also be used. Such chemistries include, but are not limited to: peptoids (PCT Publication No WO 91/19735, Dec. 26, 1991), encoded peptides (PCT Publication WO 93/20242, Oct. 14, 1993), random biooligomers (PCT Publication WO 92/00091, Jan. 9, 1992), benzodiazepines (U.S. Pat. No. 5,288,514), diversomers such as hydantoins, benzodiazepines and dipeptides (Hobbs et al., (1993) *Proc. Nat. Acad. Sci. USA* 90: 6909–6913), vinylogous polypeptides (Hagihara et al. (1992) *J. Amer. Chem. Soc.* 114: 6568), nonpeptidal peptidomimetics with a Beta-D-Glucose scaffolding (Hirschmann et al., (1992) *J. Amer. Chem. Soc.* 114: 9217–9218), analogous organic syntheses of small compound libraries (Chen et al. (1994) *J. Amer. Chem. Soc.* 116: 2661), oligocarbamates (Cho, et al., (1993) *Science* 261:1303), and/or peptidyl phosphonates (Campbell et al., (1994) *J. Org. Chem.* 59: 658). See, generally, Gordon et al., (1994) *J. Med. Chem.* 37:1385, nucleic acid libraries (see, e.g., Strategene, Corp.), peptide nucleic acid libraries (see, e.g., U.S. Pat. No. 5,539,083) antibody libraries (see, e.g., Vaughn et al. (1996) *Nature Biotechnology*, 14(3): 309–314), and PCT/US96/10287), carbohydrate libraries (see, e.g., Liang et al. (1996) *Science*, 274: 1520–1522, and U.S. Pat. No. 5,593,853), and small organic molecule libraries (see, e.g., benzodiazepines, Baum (1993) *C&EN*, January 18, page 33, isoprenoids U.S. Pat.

No. 5,569,588, thiazolidinones and metathiazanones U.S. Pat. No. 5,549,974, pyrrolidines U.S. Pat. Nos. 5,525,735 and 5,519,134, morpholino compounds U.S. Pat. No. 5,506,337, benzodiazepines U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

A number of well known robotic systems have also been developed for solution phase chemistries. These systems include, but are not limited to, automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.) which mimic the manual synthetic operations performed by a chemist and the Venture™ platform, an ultra-high-throughput synthesizer that can run between 576 and 9,600 simultaneous reactions from start to finish (see Advanced ChemTech, Inc. Louisville, Ky.)). Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

B) High Throughput Screening

Any of the assays for protease activity and/or for modulators of protease activity, or for other cleaving activity or for modulators of other cleaving activity (e.g. glycosylase activity, nuclease activity, lipase activity, and the like) described herein are amenable to high throughput screening. Preferred assays detect alterations of a signal produced by an indicator of this invention in response to the presence of a test compound.

The assays need not screen a single test agent at a time. To the contrary, to facilitate high-throughput screening, a single assay may be run with at least two, preferably at least 5, more preferably at least 10, and most preferably at least 20 test compounds. If the assay positive, subsequent assays can be run with a subset of the test agents until the agents having the activity are identified.

C) High-throughput Assays for Optical Signals (e.g. Fluorescence, Altered Spectra, etc.)

High throughput assays for various reporters are well known to those of skill in the art. For example, flow cytometers and multi-well fluorimeters are commercially available.

Example 17 illustrates the use of a PE Biosystems FMAT™ System 8100, automated, macro-confocal high-throughput screening (HTS) system for fluorescent, homogeneous, multiplexed, live cell- and bead-based screening assays for the assays of this invention.

VIII. Other Indicator Compositions.

As explained above, it was a discovery of this invention that fluorescent molecules covalently attached on opposite sides of a backbone (e.g., peptide cleavage site) can quench by self-interaction (e.g., through the formation of dimers). Thus, in one embodiment, indicator molecules can be made using a single fluorophore rather than a matched donor-acceptor pair. Also, as explained above, particularly preferred fluorophores are those that form H-type dimers (e.g., carboxyrhodamine 110, carboxytetramethylrhodamine, carboxyrhodamine-X, diethylaminocoumarin and carbocyanine dyes).

While, in preferred embodiments, the peptide indicators doubly labeled with a single species of flurophore, are fabricated with conformation determining regions (CDRs) according to this invention, the use of such doubly-labeled fluorophore systems is not limited to peptide substrates comprising conformation determining regions. To the contrary, homo-doubly labeled indicator systems as described herein can be used with virtually any peptide backbone providing the backbone permits "dimer" formation (reciprocal quenching) of the fluorophores. Thus, according to the methods described herein, previously known peptide backbone indicators that used fluorescence resonant energy transfer systems (FRET) (acceptor/donor) systems, can instead be designed with single fluorophores.

The use of single species labeled indicators, however, is not restricted to peptide-based compositions. To the contrary, "homo-double labeled" indicator molecules can utilize a variety of backbones including, but not limited to nucleic acid backbones, oligosaccharide backbones, lipid backbones, and the like. Methods of coupling fluorophores to such backbones are well known to those of skill in the art. For example, conjugation methods for attaching fluorophores to amino acids, peptides, proteins, nucleic acids, oligonucleotides, sugars, polysaccharides, proteoglycans, lipids, glycolipids and lipopolysaccharides, are described by Hermanson, (1995) *Bioconjugate Techniques*, Academic Press New York, N.Y., Kay M. et al., (1995) *Biochemistry*, 34: 293–300, and by Stubbs, et al. (1996) *Biochemistry* 35: 937–947.

A) Nucleic Acid Indicators.

Homo-doubly labeled nucleic acid backbones provide effective indicators for nucleic acid hybridizations and/or endonuclease activity. In this embodiment, a nucleic acid backbone is labeled with a self-quenching (e.g., H-type dimer-forming) fluorophore at the 3' and 5' end (either through a direct attachment or indirectly through (e.g., a peptide) linker). The nucleic acid backbone is selected to include self-complementary regions and thereby form a hairpin or other self-hybridized conformation that brings the fluorophores into proximity so that self-quenching occurs. When the indicator (probe) thus formed is hybridized to a complementary target nucleic acid, the self-hybridization is eliminated, the fluorophores are separated and the fluorescence signal produced by the molecule increases. Alternatively, the fluorescently labeled nucleic acid backbone can be used to assay for nuclease activity (e.g., restriction endonuclease or ribozyme activity). When the nucleic acid backbone is cleaved by a nuclease (e.g., by restriction endonuclease recognition of a target site in the backbone) the fluorophores are separated again increasing the fluorescence signal. Methods of selecting appropriate nucleic acid backbones are described by Tyagi and Kramer et al. (1996) *Nature Biotechnology*, 14: 303–308.

The homo-doubly fluorescently labeled DNA probes can be used for detection, localization, or quantification of target DNA sequences in a variety of contexts. Thus, for example, the nucleic acid indicators of this invention can be used for rapid detection of amplification products in nucleic acid amplification (e.g., PCR) reactions. Here the indicator is selected with a backbone complementary to a region of the amplification product. As amplification product is produced the indicator hybridizes to the product and the fluorescence signal activity of the PCR solution increases. The nucleic acid indicators can be used as hybridization or nuclease activity indicators in a variety of other contexts. For example, in in situ hybridization (e.g., FISH) mapping of genomic DNA sequences can be accomplished using fluorescent probes to target particular regions within chromosomes (see, e.g., Meyne(1993) *Chromosome mapping by fluorescent in situ hybridization*, pp 263–268 In: *Methods in Nonradioactive Detection* G. C. Howard, ed., Appleton & Lange, Norwalk, Conn.; Morrison (1992) *Detection of energy transfer and fluorescence quenching*, pp. 311–352 In: *Nonisotopic DNA Probes Techniques* L. J. Kricka, ed. Academic Press, New York; and Varani (1995) *Annu. Rev. Biophys. Biomol. Struct.* 24: 379–404).

In another embodiment, the self-quenching fluorophores can be used to assay two molecule interactions (e.g., protein-protein, protein-nucleic acid, ligand-receptor, etc.). In this embodiment, one fluorophore is attached to one molecule (e.g., a protein) while the second fluorophore is attached to a second molecule (e.g., a second nucleic acid or a nucleic acid binding protein). When the two molecules bind, the fluorophores are juxtaposed and quench each other (e.g., through the formation of H-type dimers). The use of donor-acceptor resonance energy transfer systems to measure two molecule interactions is described by Bannwarth et al., *Helvetica Chimica Acta*. (1991) 74: 1991–1999, Bannwarth et al. (1991), *Helvetica Chimica Acta*. 74: 2000–2007, and Bannwarth et al., European Patent Application No. 0439036A2.

B) Oligosaccharide Indicators.

Homo-doubly labeled oligosaccharide backbone indicators permit the detection of glycosidase activity and lecithin binding protein identification. The fluorophores can be conjugated directly to an oligosaccharide or glycopeptide backbone or attached indirectly through (e.g., peptide) linkers. The oligosaccharides and/or glycopeptides can be chemically synthesized, recombinantly expressed, or isolated from natural sources such as fetuin and other glycoproteins by proteolytic fragmentation of the parent glycoproteins.

As in the case for oligonucleotides, an oligosaccharide specific structure may be selected for detection of a specific glycosidase, an enzyme that hydrolyzes bonds between two sugar molecules.

When a specific oligosaccharide or lecithin is selected to look for its lecithin binding protein, then the increased fluorescence indicates the complexation events that disrupt the H-type dimer, either by separating two dyes or distorting the relative orientation of two dyes. These effects result in increased fluorescence from the homo-double labeled probe. Alternatively, complexation can be measured by quenching due to the dimerization from one fluorophore on the oligosaccharide or lecithin and the other on the binding protein.

C) Lipid Indicators

When a lipid, glycolipid or lipopolysaccharide are labeled with a self-quenching (e.g., H-type dimer forming) fluorophore and added to liposomes or other lipid (e.g., biological) membranes, a decrease in fluorescence will indicate H-type dimer formation and the degree of such fluorescence intensity will be an indication of the amount of H-type dimer formation. Because of the relative fluidity of a lipid membrane, the self-quenching fluorophores are able to interact (e.g. approach to a spacing of about 6 to about 10 Å) a stable H-type dimer results. When a membrane active agent, for example, an agent that affects either membrane fluid dynamics or permeabilization to a test compound, is added, then the observed fluorescence intensity changes indicate the test compound's ability to modify membrane fluidity or permeabilization. Hence, such labeled lipids are useful in drug screening and in development of lipid-drug delivery vehicles.

Similarly, the lipid-based probes of this invention can be used to similarly investigate the degree of lipid/protein interaction.

The technique can also be used to detect lipase activity if two parts of lipase target, e.g., phospholipid or triglyceride, are homodoubly fluorescently labeled.

IX. Cellular Uptake of Polypeptides.

It was also a discovery of this invention that attachment of a hydrophobic protecting group to a polypeptide enhances uptake of that polypeptide by a cell. The effect is most pronounced when the polypeptide also bears a fluorophore, more preferably two fluorophores (see, Example 9). In certain preferred embodiments, however, the fluorophore(s) may double as the hydrophobic group. Preferred hydrophobic groups include, but are not limited to Fmoc, 9-fluoreneacetyl group (Fa), 1-fluorenecarboxylic group, 9-florenecarboxylic group, and 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4'-dimethoxybenzhydryl (Mbh),Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), Benzyloxymethyl (Bom), t-butoxycarbonyl (Boc), cyclohexyloxy (cHxO),t-butoxymethyl (Bum), t-butoxy (tBuO), t-Butyl (tBu), Acetyl (Ac), and Trifluoroacetyl (TFA).

The hydrophobic group can be coupled to the subject (e.g. indicator or inhibitor) molecule at essentially any convenient position. In preferred embodiments, the hydrophobic group is coupled at a position such that it does not interfere with recognition/binding of the subject molecule by a cognate binding partner (e.g., a protease). In a particularly preferred embodiment, where the subject molecule is a polypeptide, the hydrophobic group is attached to a terminus. The hydrophobic group can be attached directly to the subject molecule or it can be coupled via a linker. Linkers suitable for coupling hydrophobic groups are well know to those of skill in the art.

This invention thus provides a method of delivering a molecule (e.g., a polypeptide, oligonucleotide, oligosaccharide, a lipid, etc.) into a cell. The method involves providing the molecule to be delivered (e.g., polypeptide) having attached at least two fluorophore molecules and a hydrophobic group, more preferably an Fmoc group and then contacting the cell with the molecule.

It will be appreciated that where the peptide, oligonucleotide, oligosaccharide, or lipid is to be delivered in vivo for diagnostic end point or for therapeutic purposes, fluorophores and a hydrophobic group having reduced or no toxicity are preferred. Thus, in a preferred embodiment, the fluorophores are replaced with non-toxic molecules having little or no biological activity. Preferred molecules are fused ring compounds that act as a linker joining the two ends of the molecule that is to be delivered. Particularly preferred fused ring compounds approximate the spacing of the exciton dimer.

Certain preferred fused ring compounds include, but are not limited to steroids. The relatively flat and hydrophobic fluorophores that are known for H-type dimer formation can be replaced with similarly hydrophobic and structurally rigid and/or flat fused rings found, for example, in steroid molecules. A steroid derivative, e.g., a smaller than full steroid molecule, two to three fused six member ring molecules can be cross linked via usual cross linkers to provide a size and an over all hydrophobicity comparable to the Fmoc and other hydrophobic groups described herein. Since safe metabolic pathways exist for larger molecule consisting of these smaller building blocks, the toxicity of such hybrid molecules is expected to be small. In a preferred embodiment, the hydrophobic molecules are in a size range of about 17 by 12 Angstroms. It will be appreciated that where the peptide is to be delivered in vivo fluorophores of reduced or no toxicity are preferred. Toxicities of numerous fluorophores are well known to those of skill in the art (see, e.g., Haugland, *Handbook of Fluorescent Probes and Research Chemicals*, 6th Ed., Molecular Probes, Eugene, Oreg. (1996). In addition, toxicity (e.g., $LD_{50}$) can be readily determined according to standard methods well known to those of skill in the art. In a most preferred embodiment, the fused ring compound is a fused steroid such as structures XI and XII illustrated in Latt et al.(1965) *J. Am. Chem. Soc.*, 87: 995–1003, where —$OR_1$ and —$OR_2$ can serve as activated points of attachment for the ends of peptides, nucleic acids or other molecules it is desired to transport into the cell.

As indicated above, the cellular uptake of almost any molecule will be enhanced by the attachment of the hydrophobic group and fluorophore or steroid cross-linkers. Thus, suitable molecules include virtually any molecule it is desired to introduce into the cell. Particularly preferred molecules include, but are not limited to, polypeptides (e.g., the protease inhibitors of this invention) and nucleic acids (e.g. oligonucleotide HIV inhibitors (see, e.g., Jing (1997) *Biochem.*, 36: 12498–12505), ribozymes, peptide nucleic acids, and the like).

X. Activity Detection Kits

The present invention also provides for kits for the detection of protease or other activity in samples or for the identification of modulators of such activity. The kits comprise one or more containers containing the fluorogenic protease indicators of the present invention. The indicators may be provided in solution or bound to a solid support. Thus the kits may contain indicator solutions or indicator "dipsticks", blotters, culture media, and the like. The kits may also contain indicator cartridges (where the fluorogenic indicator is bound to the solid support by the "acceptor" fluorophore side) for use in automated protease activity detectors.

The kits additionally may include an instruction manual that teaches the method and describes use of the components of the kit. In addition, the kits may also include other reagents, buffers, various concentrations of protease inhibitors, stock proteases (for generation of standard curves, etc), culture media, disposable cuvettes and the like to aid the detection of protease activity utilizing the fluorogenic protease indicators of the present invention.

It will be appreciated that kits may additionally or alternatively comprise any of the other indicators described herein (e.g., nucleic acid based indicators, oligosaccharide indicators, lipid indicators, etc). In this instance the kit will facilitate detection of the particular activities/compounds/interactions for which the particular indicator backbone is a substrate or binding agent.

XI. Protease Inhibitors

It was also a discovery of this invention that the protease indicators can also act as protease inhibitors. Protease inhibitors and protease substrates share several basic properties such as ability to bind to protease's catalytic substrate binding site, and form a relatively stable complex with a protease. Hence, many normal substrates or their fragments exhibit competitive substrate inhibition at higher concentrations. The inhibition is competitive since the inhibitor binds to the same substrate binding site of the protease whereby it competes with the native substrate in binding to the protease's catalytic domain.

This invention provides three novel approaches for protease inhibitor design. In the first approach, a normal substrate is redesigned such that it binds to protease well, but has a reduced (slow or non-existent) hydrolysis rate. The slow hydrolysis rate is achieved by introducing an altered (different) conformation and/or conformational flexibility into the protease recognition domain. After the (e.g., native) substrate binds to the protease's substrate binding site, the conformation of the peptide bond between $P_1$ and $P_1'$ is distorted into a transition conformation of a given protease's peptide bond hydrolysis reaction. If this peptide bond as well as adjacent peptide bonds are altered such that they are not distortable then the hydrolysis rate will be reduced as compared to a substrate whose cleavage site peptide bond is easily distorted into the desired transition conformation. This approach is illustrated in Example 16 which shows how one can vary the hydrolysis rate of a substrate without changing the protease recognition amino acid sequences.

Figure 5:
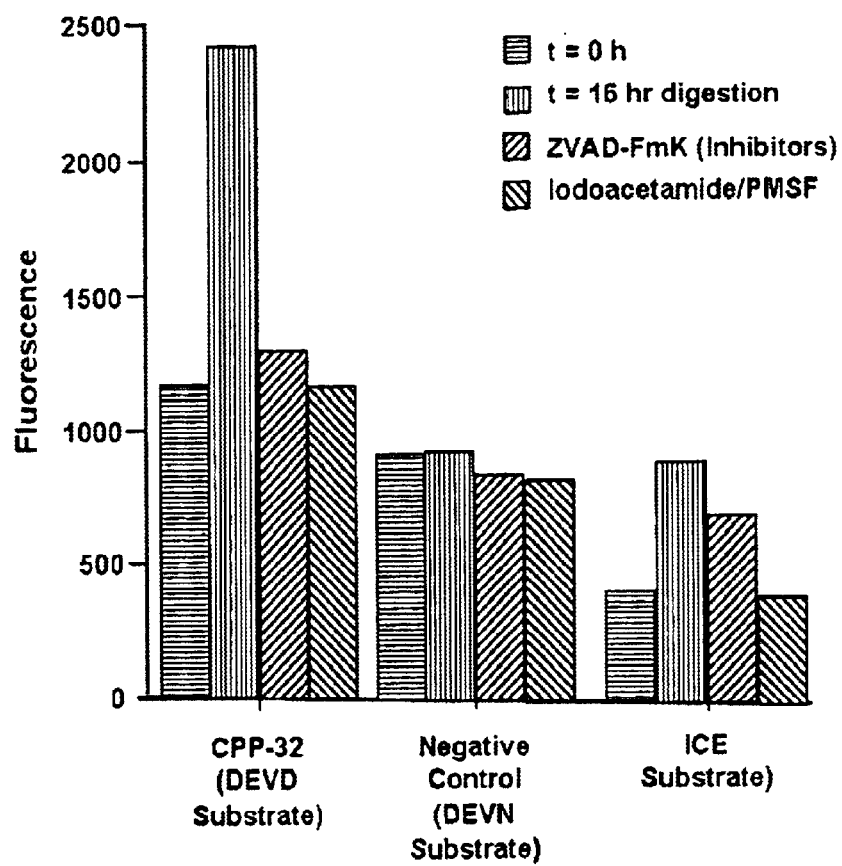
FIG. 5 illustrates fluorescence of a DEVD, a DEVN, and an ICE substrate. To one hundred μl of assay buffer (50 mM HEPES buffer pH 7.5, 10% (w/v) sucrose and 0.1% (w/v) CHAPS) containing 1 μM of a DEVD substrate a DEVN substrate, and an ICE substrate 10 μl of Jurkat cell lysate was added and incubated for 16 hours at 37° C. The Jurkat cells' lysate was prepared from the cells that had been stimulated by antiFas antibody at 1 μg/ml concentration for 6 hours. The fluorescence intensity for the substrate solution alone is indicated in FIG. 5 as a horizontal lined bar marked as t=0 hr and the fluorescence intensity of the lysate and substrate solution mixture after 16 hr is indicated by vertical line bar and is marked as t=16 hr digestion. 10 μl cell lysate was pre-incubated with 50 μm ZVAD-FMK (benzyoxycarbonyl valanyl alanyl aspartyl-fluoromethylketone) at 37° C. for 30 min. then added to the substrate solution. The fluorescence intensity after 16 hours for this mixture is indicated by the bar marked as ZVAD-FMK (inhibitor). Lastly, pre-incubated cell lysate with iodoacetamide( alkylating agent for sulfhydryl group) and PMSF ( for inhibiting serine proteases) was added to the substrate solution. The fluorescence intensity after 16 hours at 37° C. is indicated by bar marked as Iodoacetamide/PMSF. The DEVN substrate is a negative control substrate where the P1, Asp, residue is replaced by Asn. The CPP32 protease requires the P1 residue to be aspartic acid residue. The four bar graphs for the DEVN substrate (FIG. 5) clearly indicate that the activated cell lysate do not contain any other protease that digest the DEVD substrate, since the intensity for 16 hour digestion is the same as the substrate alone. The bar graphs for the DEVD substrate indicate that the activate cell lysate do contain CPP32 protease and this protease activities are inhibited by ZVAD-FMK, known CPP32 protease inhibitor. The contribution of any other proteases in digesting DEVD substrate is very small as indicated by the difference between the intensities of ZVAD-FMK bar to Iodoacetamide/PMSF bar.

In a second approach, the inhibitor is produced by replacing the critical $P_1$ or $P_1'$ residue which makes it difficult to distort the cleavage site peptide bond. Normally, the amino acid side chains of $P_1$ and $P_1'$ residues interact specifically with the side chains of the protease catalytic domain. These specific interactions facilitate coordination of the peptide bond distortion into a transition conformation of the hydrolysis reaction. Thus, for example, when the critical $P_1$ residue of aspartic acid residue in the CPP32 protease substrate is replaced with non-charged asparagine then normal interaction between the substrate and aprotease does not take place even though the modified substrate binds to the protease's substrate binding site. Again, this leads to a slower or zero hydrolysis rate. The example of this $P_1$ residue substitution effect in designing an inhibitor is illustrated by the properties of the DEVN peptide (see, e.g., FIG. 5 and Example 12). The biological conformation that the substrate DEVN is an inhibitor is demonstrated in Example 13. Additional evidence that the peptide DEVN does bind to protease is given in Example 15.

The $P_1$ residue can be changed to introduce either charged amino acid side chains or a structurally rigid, e.g., proline, residue as illustrated in the Table 3, substrate sequences for Hepatitis C viral protease substrate NS3 NS5A/5B of DVVC CSMS (SEQ ID NO:212, normal substrate) and DVVC CPdMS (SEQ ID NO:213, inhibitor). The underlined residues are the $P_1$ residues.

In a third approach, the amide bond between $P_1$ and $P_1'$ residues of a substrate can be changed to a non-hydrolyzable chemical bond including, but not limited to an ether, thioether, methylene bond, or alkylene (C=C) or ether bond (C—O—C(=O)) keeping the same amino acid side chains for the $P_1$ and $P_1'$ residues. Also the amide bond can be substituted with a retroinverso bond or other pseudoamino acid bond such as $CH_2$—NH or C(=O)—S replacing the carbonyl group with a $CH_2$ group.

EXAMPLES

The invention is illustrated by the following examples. These examples are offered by way of illustration, not by way of limitation.

Example 1

Synthesis of Fluorogenic Molecule for Detecting Protease Activity

Peptide syntheses and derivitizations were performed as described in PCT publication PCT/US98/03000 (WO 98/37226) which is incorporated herein by reference.

Example 2

The Fluorotenic Protease Indicators Provide a Strong Signal when Digested

In order to demonstrate that the fluorogenic protease indicators of this invention are easily digested by a protease, the degree of cleavage was determined by assaying for the appearance of indicator cleavage products in the presence of a protease.

Approximately 1 microgram of protease indicator, having the formula $F^1$-Asp-Ala-Ile-Pro-Nle-Ser-Ile-Pro-Cys-$F^2$ (SEQ ID No:1) where $F^1$ is a donor fluorophore (5'-carboxytetramethylrhodamine (5-TMR)) linked to aspartic acid via the alpha amino group and $F^2$ is an acceptor fluorophore (rhodamine X acetamide (R492)) linked via the sulfhydryl group of the cysteine was dissolved in a buffer consisting of 50 mM sodium phosphate, 1 mM EDTA at pH 8.9. To this solution was added 1 unit of elastase. The solution was analyzed by HPLC before and about 30 minutes after the addition of elastase. The digestion was carried out at 37° C. The HPLC separated components were monitored at a wavelength of 550 nm which allowed detection of both the 5-TMR fluorophore the R492 fluorophore and at 580 nm which allowed detection of the R492 fluorophore.

Figure 1B:
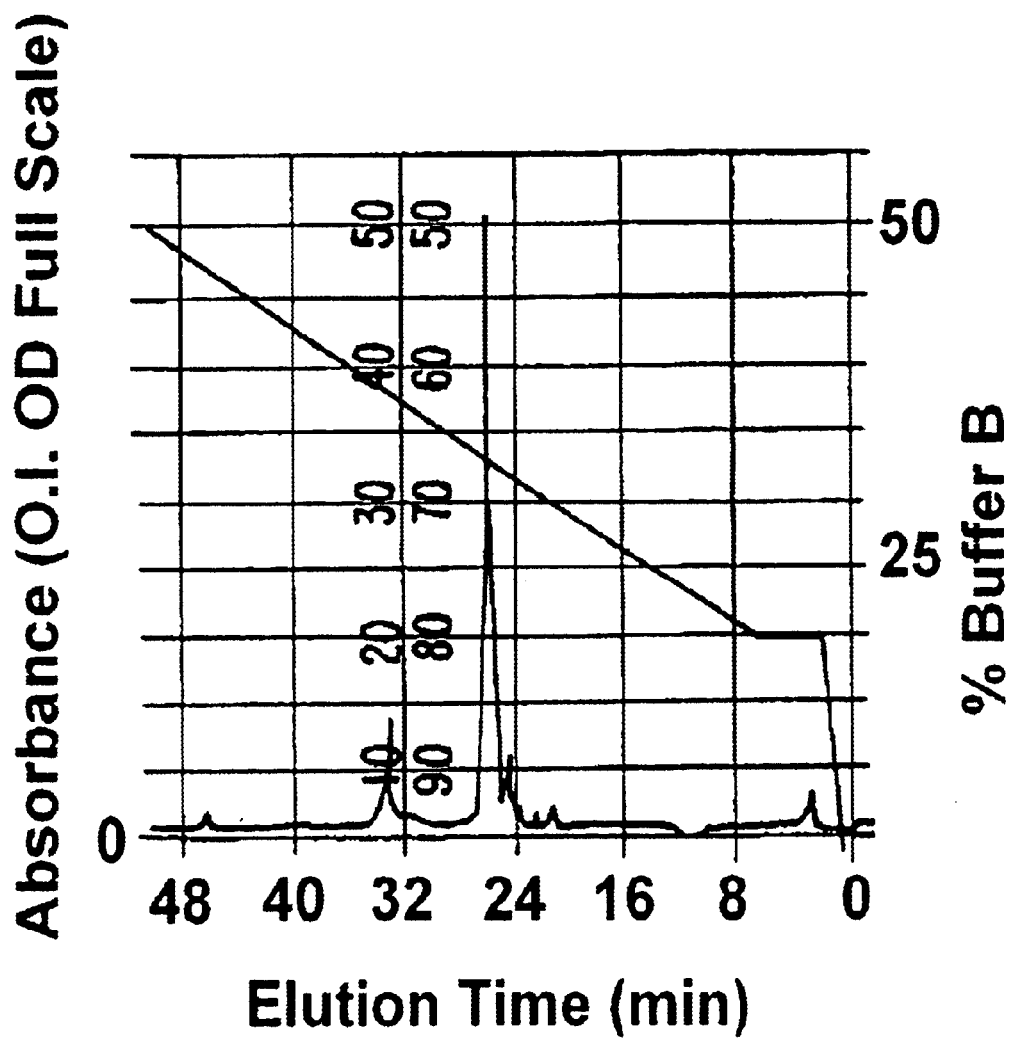
Figure 1C:
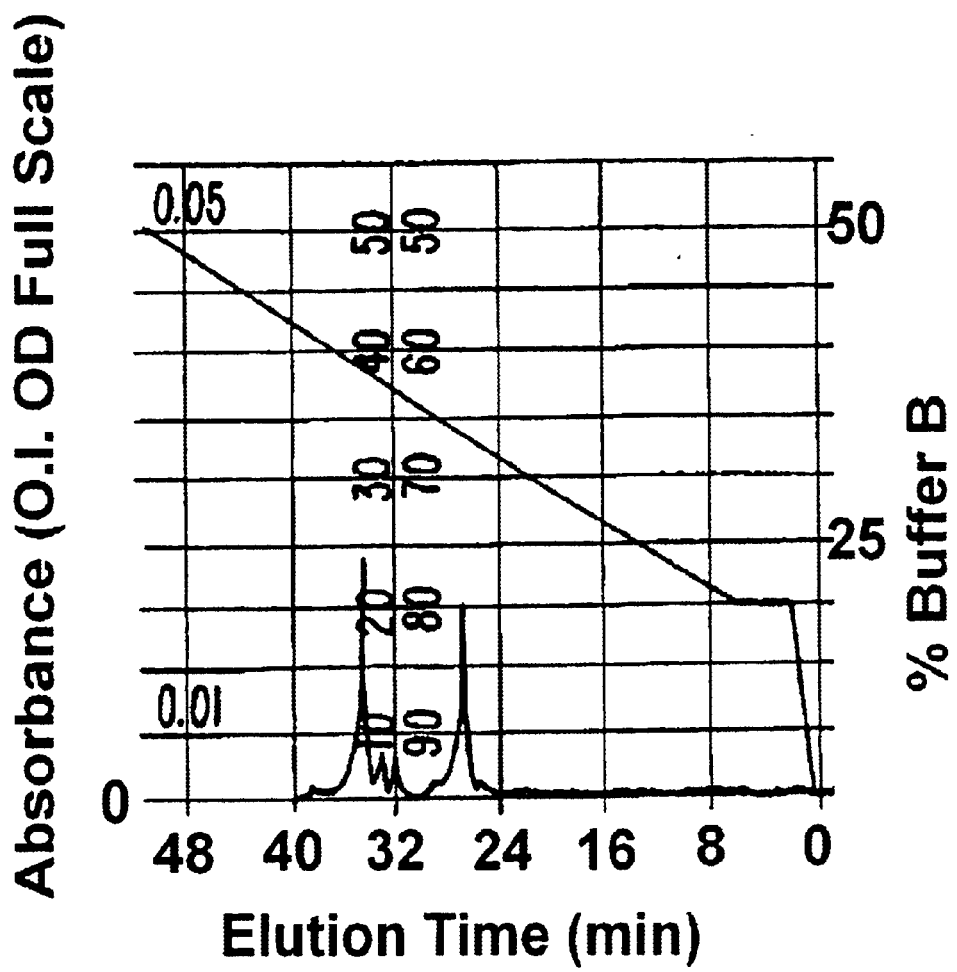

The results are indicated in FIG. 1 which shows the HPLC profiles of the fluorogenic protease indicator solution before and after addition of the protease elastase. FIG. 1(a) shows the HPLC before addition of the elastase showing a single peak representing the intact fluorogenic protease inhibitor. After addition of the elastase (FIGS. 1(b) and 1(c)) there was no trace of the late eluting single peak (FIG. 1(a)) indicating complete digestion of the fluorogenic protease indicator. In addition, the two predominant peaks in FIGS. 1(b) and 1(c) indicate that the digestion occurred primarily at a single site. There are a few smaller peaks indicating a low degree of digestion at other sites within the peptide sequence, however, the striking predominance of only two digestion peaks suggests that these secondary sites were not readily accessible to the elastase.

Changes in the emission spectrum of the fluorogenic protease indicator after the addition of an elastase protease was monitored using an SLM spectrofluorometer model 48000 with slit widths set at 4 nm on both the excitation and emission sides. All measurements were carried out at 37° C.

Figure 2A:
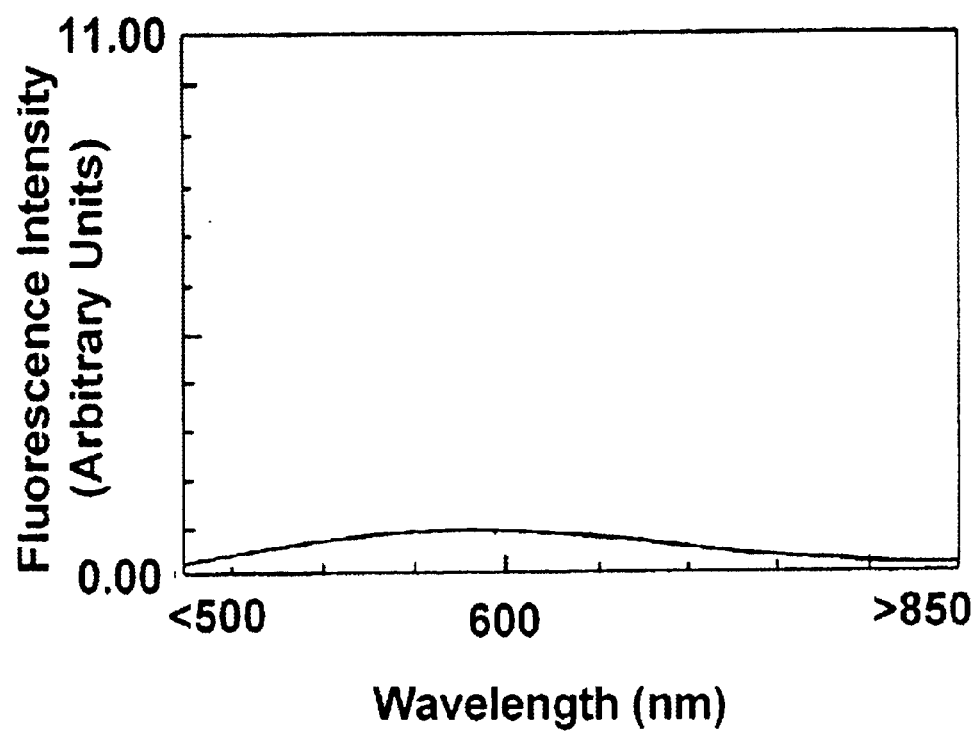
FIGS. 2A and 2B show the emission spectra of the D-NorFES-A fluorogenic protease indicator (FIG. 2A) before and (FIG. 2B) after the addition of elastase.
Figure 2B:
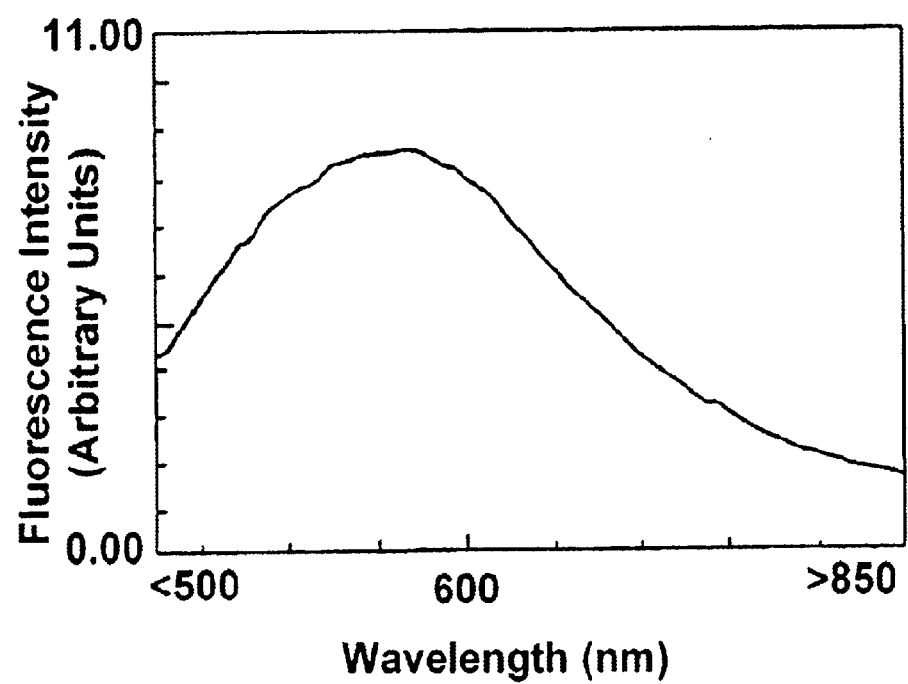
Figure 3:
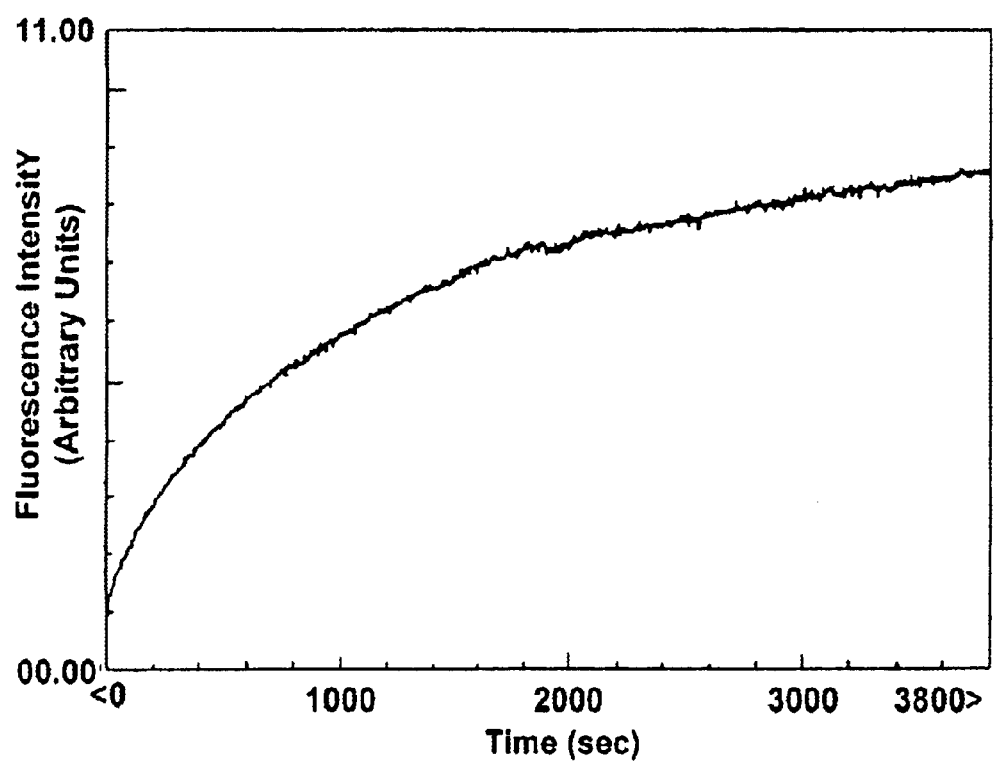
FIG. 3 shows the time-dependent increase of the fluorogenic protease indicator of FIG. 1, as a function of time after addition of 1 unit of elastase.

Spectra in FIG. 2 show emission of the fluorogenic protease indicator (a) before and (b) after addition of elastase, while the time dependent increase of the indicator's donor fluorophore emission intensity, after addition of elastase, is plotted in FIG. 3. The fluorogenic protease inhibitor showed more than a 10 fold increase in fluorescence at 589 nm after treatment with the elastase protease (FIG. 2(a) compared to FIG. 2(b)) with over a 5 fold increase in fluorescence occurring within the first 1000 seconds of exposure to the protease. The changes in intensity between treated and untreated indicators are, to some degree, a function of slit widths used, since they represent the signal integrated across the particular slit width. Thus, if wider slit widths were used (e.g. 8 or 16 nm slits) an even greater signal would be provided in response to digestion.

Example 3

The Fluorescence Signal was Due to Intramolecular Energy Dequenching

In order to show that the fluorescence increase observed after protease treatment was due to intramolecular energy dequenching, the signal produced by elastase digestion of the fluorogenic protease indicator was compared to the signal produced by elastase treatment of the same peptide backbone coupled to either $F^1$ (5-TMR) or to $F^2$ (R492). The change in fluorescence intensity of the donor fluorophore after addition of 1 unit of elastase to equal concentrations of the double-fluorophore molecule and the two single-fluorophore molecules.

Figure 4A:
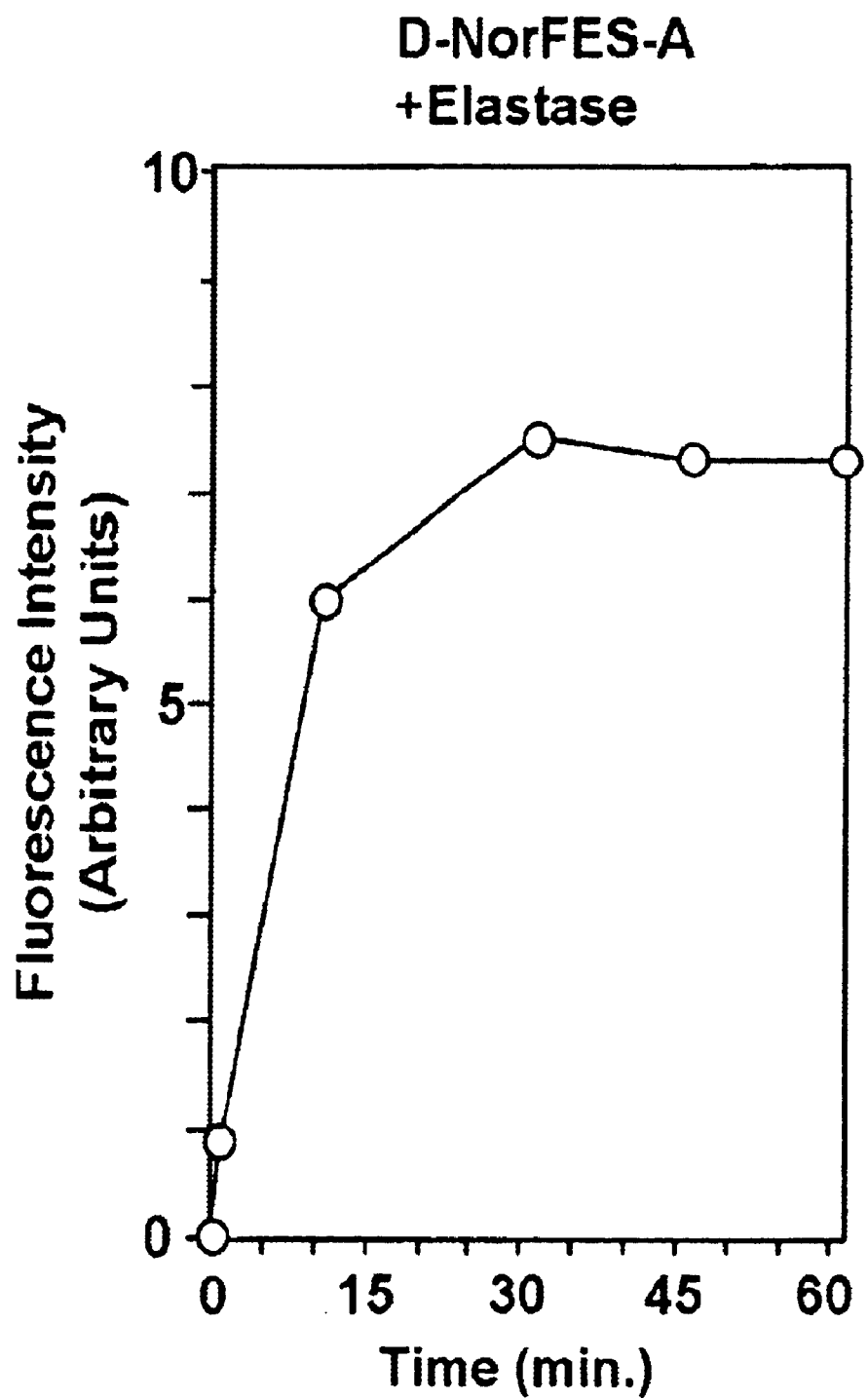
FIGS. 4A and 4B show the fluorescence intensity of the donor fluorophore as a function of time after addition of 1 unit of elastase.
Figure 4B:
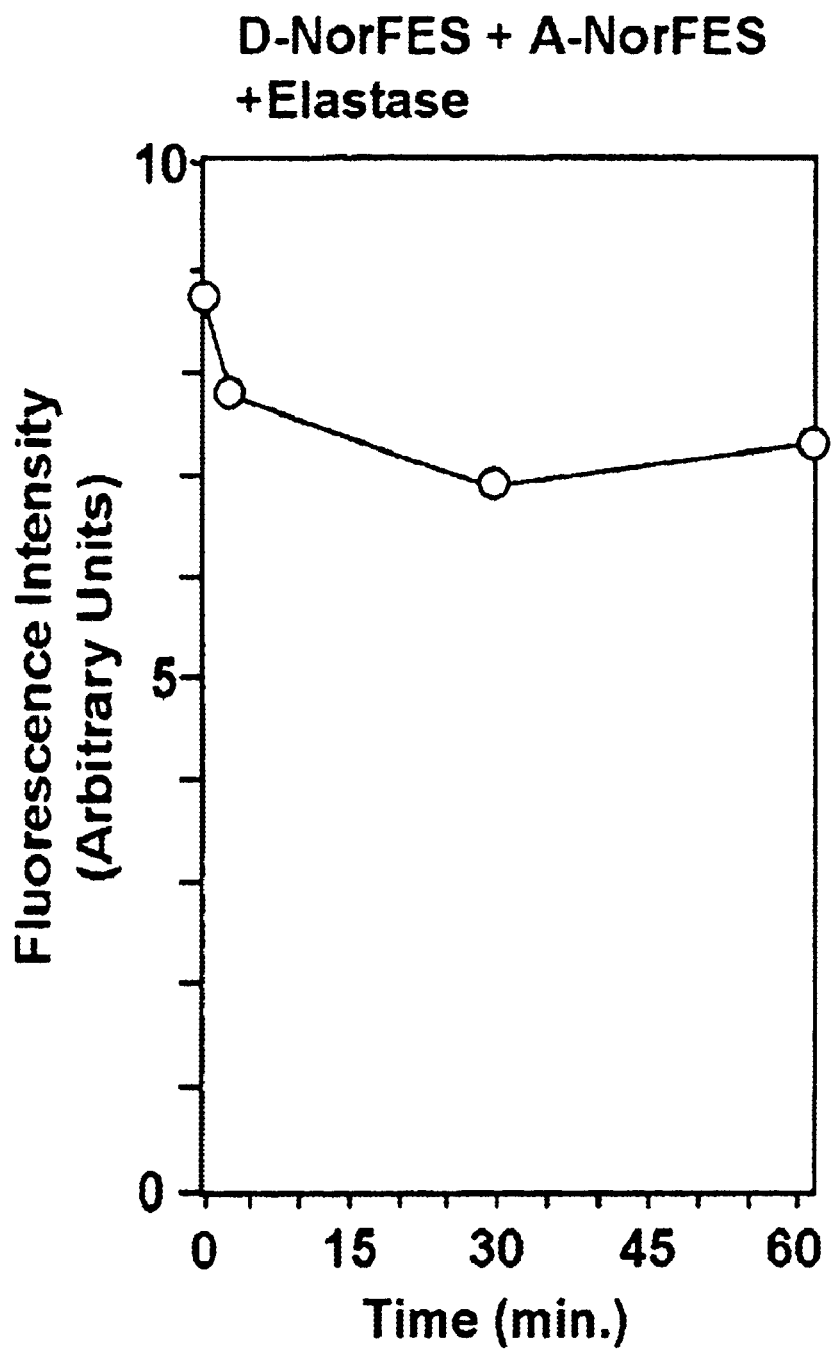

The results are illustrated in FIG. 4. The double-fluorophore molecule showed nearly complete quenching initially, followed by a dramatic increase in fluorescence after addition of the elastase which reached a constant value approximately 30 minutes after addition of the elastase (FIG. 4(a)). In contrast, the two single-fluorophore molecules showed virtually no initial quenching and no significant change in fluorescence after addition of the elastase. In fact, the fluorescence level was comparable to the fluorescence level of the fully digested double-fluorophore indicator molecule (FIG. 4(b)).

These results indicate that the increase in fluorescence intensity of the fluorogenic protease indicator is due to interruption of the resonance energy transferred intramolecularly from the donor fluorophore to the acceptor fluorophore and not to interaction between the fluorophore and the peptide backbone. This is significant since it is known that upon binding to a large protein or hydrophobic peptide the fluorescence of many hydrophobic fluorophores is quenched.

Example 4

Protease Specificity is a Function of the Indicator Conformation.

Without being bound to a particular theory, it is believed that the fluorogenic protease indicators of the present invention achieve a high degree of protease specificity due to their folded structure, more particularly due to their relatively rigid U-shaped conformation. The degree of quenching obtained from the molecule reflects the average separation of two fluorophores. Thus, it was predicted that if the protease indicators existed in a relatively unfolded or flexible state, conditions that tend to cause unfolding (denaturation) would have little or no effect on the fluorescence of the molecule in the absence of a protease. Conversely, if the molecule is relatively rigid, then denaturing conditions would be expected to increase the fluorescence signal as the average separation of the fluorophores would be expected to increase thereby decreasing the quenching effect.

Thus, the effect of denaturing conditions on the fluorescence of the fluorogenic protease indicator in the absence of a protease was determined. First the change of fluorescence of the indicator of Example 1, as a function of added chaotropic reagent concentration (2M or 8M urea) was measured. When the fluorogenic protease indicator was denatured with a chaotropic reagent the fluorescence intensity increased with time to a plateau as the molecule denatured (unfolded).

These data indicate that the fluorogenic protease indicator normally exists in a stable folded conformation created by the conformation determining regions, as was predicted by a model based on an energy minimization algorithm. The plateau fluorescence level represents residual quenching of the fluorophores still joined by the fully denatured peptide backbone. Digestion of the extended (denatured) peptide results in greater than a 2 fold increase in fluorescence as the fluorophores are able to move farther away from each other.

Example 5

Quenching and Release of a Peptide Doubly-Labeled with One Fluorophore

It was a surprising discovery of this invention that the peptide backbones of this invention doubly labeled with one fluorophore still achieve fluorescence quenching thus suggesting quenching through another mechanism besides resonance energy transfer.

In order to assess the extent ground-state dimerization and collisional quenching contribute to the total observed quenching, the series of doubly-labeled peptides listed in Table 5 was synthesized.

In addition to comparing absorption spectra of the dyes alone with the NorFes peptides singly labeled with each dye, emission spectra taken before and after cleavage were compared to determine the percent of quenching and the existence of fluorescent signal quenching by means other than resonance energy transfer (RET).

Fluorophores were linked to the amino terminus via the α-amino group of Aspartic acid residue (D) and to the ε-amino group of lysine (K). Labeling was accomplished by the displacement of a succinimidyl group linked to 6-TMR or DER. The structure of the peptide, called NorFES is:

As determined from absorption spectroscopy, all doubly-labeled peptides, except fluorescein-NorFES-fluorescein, showed the existence of so called ground-state dimers. This was indicated by shift of absorption maxima to shorter wavelengths as well as a shape change of the absorption spectra as compared with the spectra for the enzyme digested doubly-labeled samples. Upon cleavage with elastase, the ground-state dimers were destroyed and the resulting spectra were the same as a solution containing equal concentrations of the respective singly labeled peptides.

Without being bound to a particular theory, it is believed that the ground-state dimer formation observed in the compounds designed and synthesized according to the present invention indicates that the U-shaped conformation of the peptide backbone brings the fluorophores into close spatial proximity thus allowing quenching through ground-state dimerization. It was a surprising discovery that the polypeptides of this invention allowed the formation of ground-state dimers at a significantly lower dye concentration than previously observed. For example, ground-state dimerization of free fluorescein dye in solution was only observed at concentrations higher than 0.74 M, ground-state dimerization of free Eosin dye in solution was only observed at concentrations higher than $2.8 \times 10^{-2}$ M (see, Forster and Konig (1957) *Zeitschrift fur Electrochemie*, 61: 344), and ground-state dimerization of Rhodamine B dye in solution was only observed at concentrations higher than $6 \times 10^{-4}$ M (see Arbeloa and Ojeda (1982) *Chemical Physics Letters*, 87: 556). In contrast, in the present invention, the effects are observed at $4.0 \times 10^{-7}$ M or about a 1000 fold lower concentration than the reported values.

The observation of the ground-state dimer for the compounds synthesized according to the present invention predicted a significant level of fluorescent quenching for doubly-labeled peptide with the same fluorophore as those compounds listed in Table 11. In fact this prediction was confirmed; a comparison of 6-TMR-NorFES-DER with 6-TMR-NorFES-6-TMR, i.e., the hetero doubly-labeled with the homo doubly-labeled peptides, indicates the degree of quenching is slightly higher in the hetero- vs. the homo- (94 vs. 90%). The fluorescein derivative, however, exhibited only 55% quenching. The symbols $I_0$ and $I_c$ for the percent fluorescent quenching (%Q) refer to the fluorescence intensity for the intact labeled peptide and the enzyme digested labeled peptide solution respectively.

TABLE 5

Cleavage rate ($T_{1/2}$) and percentage of quenching (% Q) of hetero- and homo-labeled peptides. $T_{1/2}$ is the time in seconds after addition of a protease (e.g. elastase) at which the fluorescence signal is ½ maximum. The symbols $I_0$ and $I_c$ refer to the fluorescence intensity (I) for the intact labeled peptide and the enzyme digested labeled peptide solution respectively.

| Compound | $T_{1/2}$ | % Q = (1 − ($I_0/I_c$)) × 100 |
|---|---|---|
| 6-TMR-NorFes-DER | 80 | 94 |
| 6-TMR-NorFes-6-TMR | 44 | 90 |
| 6-TMR-NorFes-6-TMR | 44 | 90 |
| DER-NorFes-DER | 152 | 90 |
| Fl-NorFes-Fl | 18 | 55 |
| 6-TMR-NorFes-DER | 80 | 94 |
| 6-TMR-K-NorFes-DER | 125 | 97 |
| 6-TMR-NorFes-6-TMR | 44 | 90 |
| 6-TMR-K-NorFes-6-TMR | 84 | 92 |

The substrate sequence could be extended by one amino acid residue and the fluorophore could be attached through the episilon amino group on the lysine residue's side chain without major perturbation to the amount of observed quenching. Specifically, this addition (peptides designated resulted in a slight decrease in cleavability rate and a very slight inceease in the percent quenching for both the hetero- and homo-doubly-labled peptide (in the peptides, N-terminal labeling was via the epsilon-amino group of lysine rather than the α-amino terminus).

Rates of cleavage ($T_{1/2}$) of these substrates by elastase were also measured by recording in time after addition of the protease at which the signal was one-half maximum (see, Table 5). a comparison of three homo-doubly-labeled peptides, i.e., NorFES labeled with two molecules of 6-TMR, DER, and fluorescein (Fl), shows the order of cleavability to be: Fl-NorFES-Fl>6-TMR-NorFES-6-TMR>DER-NorFES-DER.

Example 6

Dye-dye Dimers are Formed in Long Peptides

In addition, (homodoubly-labeled) PAI-2, CS-1 (a 31 residue long peptide) and two DEVD-like peptides were synthesized and derivatized. PAI-2 and CS-1 allowed the dye-dye dimer formation. The CS-1 peptide showed that in a significantly longer peptide the dye-dye dimer structure can be formed. Note this pepticle contained four proline residues in the amino terminal side of the putative cleavage site Ile-Leu bond. There was one proline in the carboxyl domain as well. The results from the CS-1 peptide support a potentially larger sequence between the two dyes (fluorophores). Two DEVD-like peptide's amino acid sequences that did not allow the formation of productive H-type dimers are $F_1$-DEVDGIDPK[$F_1$]GY (SEQ ID NO:215) and $F_1$-PDEVDGIDPK[$F_1$]GY (SEQ ID NO;216).

Example 7

Cellular Uptake of Substrates Examined by Flow Cytometric and Fluorescence Microscopic Analysis The compounds listed in Table 12 were synthesized and assayed for cellular uptake. Cellular internalization of the substrates was tested using Jurkat cells (a human acute T cell leukemic line), HL-60 cells (a human promyelocytic leukemic line), human lymphocyte lines, A1.1 cells (a murine T-cell line), and murine primary thymocytes. Procedures used in determining substrate uptake by viable cells are provided in Example 6 (for the HPLC procedures), in Example 2 (for the fluorescence microscopic analysis), and in Example 3 (for the flow cytometric analysis). a summary of these analyses with respect to cellular uptake of substrates is presented in this example.

TABLE 6

Compounds assayed for cellular uptake.
Abbreviations used in the following table
are: $F^1$: carboxytetramethylrhodamine;
Z: benzyloxycarbonyl group; Fm: Fmoc group;
K[F1]: $F^1$ is covalently attached
through the epsilon amino group of lysine (K).
Single letter amino acid residues are used in
the sequences except for Nlu for norleucine,
B for aminoisobutyric acid and J for epsilon
amino caproic acid residue. H: HPLC, FM:
Fluorescence microscopy, FC: flow cytometry.

| | Structure | Cellular uptake/ magnitude | Uptake checked by | SEQ ID NO |
|---|---|---|---|---|
| 1 | Fm-K[F1]DAIPNluSIPK[F1]GY | Yes/high | FM | 217 |
| 2 | K[F1]DAIPNluSIPK[F1]GY | Yes/weak | FM | 218 |
| 3 | Fm-DAIPNluSIPK[F1]GY | No/ | FM | 219 |
| 4 | Fm-K[F1]DBDEVDGIDPK[F1]GY | Yes/high | FM & FC | 220 |
| 5 | K[F1]DBDEVDGIDPK[F1]GY | Yes/weak | FM | 221 |
| 6 | Fm-K[F1]DBDEVNGIDPK[F1]GY | Yes/high | FM | 222 |
| 7 | K[F1]DBDEVNGIDPK[F1]GY | Yes/weak | FM & H | 223 |
| 8 | Fm-K[F1]DBEVDGIDPK[F1]GY | Yes/high | FM & FC | 224 |
| 9 | K[F1]DYBADGIDPK[F1]GY | Yes/weak | FM | 225 |
| 10 | Fm-K[F1]DBGDEVDGIDGPK[F1]GY | Yes/high | H & FC | 226 |
| 11 | Fm-K[F1]DBJGDEVDGIDGJPK[F1]GY | Yes/high | FC | 227 |
| 12 | Z-K[F1]DBJGDEVDGIDGJPK[F1]GY | Yes/weak | FM | 228 |
| 13 | Fm-K[F1]DYBADGIDPK[F1]GY | Yes/high | FM | 229 |
| 14 | K[F1]DBEVDGIDPK[F1]GY | Yes/weak | FM | 230 |

The data listed in Table 6 indicate that: (1) the presence of two fluorophores alone is not optimum for cellular uptake as illustrated by structures 2, 5, 7, and 9; (2) addition of a 9-fluorenylmethoxycarbonyl (Fmoc) group at the alpha amino group plus attachment of only one fluorophore, does not result in significant cellular uptake (e.g., compound 3); and (3) two fluorophores plus at least one Fmoc group allows efficient cellular uptake of the substrates (structures 1, 4, 6, 8, 10, 11, and 12).

Other experiments utilizing protease substrates of this invention labeled with two identical fluorophores and at least one additional hydrophobic group such as an Fmoc group fits this paradigm. Replacing this Fmoc group with the less hydrophobic and smaller benzyloxycarbonyl group resulted in lower levels of cellular uptake, but was significantly better than a compound without a hydrophobic group such as DEVD peptide compound structure 5.

These data indicate that Fmoc may be replaced with Benzyloxycarbonyl, Z, or other hydrophobic groups such as Xanthyl (Xan), Trityl (Trt), 4-methyltrityl (Mtt), 4-methyltrityl (Mmt), 4-methoxy-2,3,6-trimethyl-benzenesulphonyl (Mtr), Mesitylene-2-sulphonyl (Mts), 4,4'-dimethoxybenzhydryl (Mbh),Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), Benzyloxymethyl (Bom), t-butoxycarbonyl (Boc), cyclohexyloxy (cHxO),t-butoxymethyl (Bum), t-butoxy (tBuO), t-Butyl (tBu), Acetyl (Ac), and Trifluoroacetyl (TFA).

When the acid groups on compound 5, DEVD peptide, were ethyl esterified, this modified peptide did not show any enhanced cellular uptake by viable cells. Hence the importance of the Fmoc group and the two fluorophores forming H-type dimers are illustrated by this negative example.

Example 8

Fluorescence Microscopic Analysis of Cells Incubated with Elastase or Apoptosis-Related Protease Substrates The elastase substrate, Fm-K[F1]DAIPNluSIPK[F1]GY (SEQ ID NO:231), (where F1 was carboxytetramethylrhodamine, Fm was Fmoc, K[F1] was F1 covalently attached through the epsilon amino group of lysine (K), and Fm-K is the Fmoc group covalently attached at the alpha amino group of the amino terminal lysine residue) was used with HL-60 cells. Cells were incubated with various concentrations of elastase substrate ranging from 10 nM to 10 μM for 5 minutes to 60 minutes. Then the cells were diluted 5-fold with RPMI 1640 medium containing 5% serum or with phosphate buffered saline. The samples were centrifuged and washed once more with 1 ml of washing solution. After centrifugation and removal of the washing solution, cell pellets were loosened with about 25 ul of medium and these cells were transferred to a glass capillary. Capillary tubes were then placed on a glass microscope slide and examined under a fluorescence microscope using standard rhodamine filters.

For apoptosis-related protease activity determination, 10 μM concentration of the compounds listed in Example 7

(compound structures 2 through 13) were incubated with cells for 30 min. to 3 hours. The cells were then washed similarly twice. Using glass capillary tubes, the washed cells were transferred and examined under a fluorescence microscope.

Example 9

Flow Cytometric Analysis of Cells Incubated with Apoptosis-Related Protease Substrates The concentration of substrates used in flow cytometric analysis was 10 μM in RPMI1640 medium containing 4 to 10% fetal calf serum. Cell densities during incubation with the chosen substrates ranged from 50,000 cells per ml to 4,000,000 per ml. Incubation times were from 30 min. to 3 hours at 37° C. and incubation volumes were 50 μl to 2 ml. After incubation with substrate for 30 to 60 min, cell suspensions were diluted 10-fold with ice cold Hank's Buffered Saline Solution (HBSS). This filtered cell suspension was then subjected to flow cytometric analysis using a 488 nm excitation source. Becton Dickenson, Inc.'s flow cytometer, FacSort, was used in the flow cytometric analysis. Typically, 10,000 to 30,000 events per sample were collected.

Control cells without substrate incubation and the sample with the greatest expected fluorescence signals were used to set the instrument detector parameters. For example after 15 minutes incubation of Jurkat cells with substrate compound #11 Fm-CGD2D: Fm-K[F1]DBJGDEVDGIDGJPK[F1]GY (SEQ D NO:232, where F1 was carboxytetramethylrhodamine; Fm was Fmoc, K[F1] was F1 covalently attached through the epsilon amino group of lysine (K), Nlu was norleucine, B was aminoisobutyric acid, and J was epsilon-aminocaproic acid) an increase of about 10 channels indicating cellular uptake of the substrates was measured. Note substrate #11 was not completely quenched. Hence, a small amount of background fluorescence would be expected from the intact substrate. Signals from the cells that had been activated with 1 μ/ml of ant-Fas antibody, CH11 clone for 1 to 6 hours indicated an increase in peak channel number. As much as a ten-fold increase in fluorescence intensity was observed. When the cells were co-incubated with the CPP32 protease inhibitor ZVAD-fluoromethylketone at 50 μM along with an apoptosis inducing agent, e.g., anti-Fas antibody, this observed increase in fluorescence intensity was eliminated. This indicated that the signal from compound 11 was due to the CPP32 protease activity which was inhibitable by ZVAD-FMK. Hence, the observed fluorescence intensity in each cell as determined by flow cytometric analysis served as a direct measure of the intracellular CPP32 protease activity.

Example 10

Competitive Substrate Inhibitors Illustrated by Their Effects on Cell Lysate Hydrolysis of Apoptosis-related Protease Substrates The level of CPP32 protease activity in the 6 hr ant-Fas-stimulated Jurkat cell lysate was examined using the protease substrate, DEVD-AFC (where AFC is aminofluoromethyl coumarin) 50 μM substrate concentration at 37° C. The buffer used was 50 mM HEPES, pH7.5, 10% w/v sucrose, 0.1% w/v CHAPS.) Fluorescence intensity changes were monitored with an SLM 48000 spectrofluorometer. The hydrolysis rate of DEVD-AFC was found to depend upon the concentration of DEVD, DEVN, and ICE substrates (compounds 5, 7, and 9 in Table 6) present in the reaction mixtures. As the concentrations of DEVD, DEVN, and ICE were raised to 25 μM, the rate of DEVD-AFC hydrolysis was decreased. Hence, DEVD, DEVN and ICE substrates do bind to the substrate binding site of target proteases such as CPP32 and act as competitive inhibitors since their hydrolysis rates are slower than that of DEVD-AFC substrate. It was surprising to find that the substrate control peptide with its $P_1$ residue mutated with a conservative uncharged residue Asn still retained the ability to bind to the protease substrate binding site and exhibit enzyme inhibition.

Example 11

Substrates Delay and Inhibit Apoptosis Stimuli in Whole Cells

Jurkat cells are normally grown in 10% fetal calf serum containing RPMI 1640, at 37° C. in a 5% $CO_2$ atmosphere. When the serum content was dropped to 4%, the Jurkat cell growth rate not only slowed down but also a significant number of cells died within 36 hours. The cell density used was about 400,000 cell per ml. After 36 hours, control wells contained about 50% dead cells (trypan blue-positive cells), whereas the wells containing 0.1 or 1.0 μM concentration of compound #11 (Table 6) "Fm-CGD2D" or Fm-K[F1] DBJGDEVDGIDGJPK[F1]GY (SEQ ID NO:233) showed only 10% or 8% nonviable cells. Hence, compound #11 which exhibits efficient cellular uptake slowed down apoptosis in these Jurkat cells where it acted as a CPP32 protease inhibitor or a CPP32 activating protease inhibitor.

Example 12

Isolation of Intact and Cleaved Substrate Fragments from Cells

Jurkat cells, which had been induced into apoptosis by the ant-Fas antibody (1 μg/ml for 2 hours at 37° C.) were incubated with 10 μM substrate compound #10 Fm-G2D2D. After one hour incubation with this substrate, the cells were washed with 4% serum containing RPMI 1640 medium (1 ml wash solution for every 100 μl of incubation medium). Cells were washed three times, and then solubilized with cell lysis buffer containing Triton X-100. This cell lysate was then analyzed using a $C_4$ reverse phase chromatography column and a water/acetonitrile eluent system containing 0.075% trifluoroacetic acid throughout. Analysis showed the presence of intact substrate with two major new peaks that eluted earlier than the intact substrate. The two recovered major peaks showed rhodamine absorption spectra; hence, these correspond to two major substrate fragments that are generated upon protease cleavage of the substrate.

Example 13

Fluorescence Signal from DEVN Substrates when Mixed with Target Enzyme Containing Solution DEVN (10 μM), a substrate control peptide, compound 7 of Table 6, was found to be resistant to protease digestion by an apoptosis-activated Jurkat cell lysate. Extensive digestion time did not result in any further increase in fluorescence intensity. HPLC reverse phase analysis of this reaction mixture confirmed the presence of a totally uncleaved substrate. Substitution of the $P_1$ residue, Asp, by a non-charged amino acid Asn resulted in converting a protease substrate into a protease non-substrate.

This control peptide exhibited competitive substrate inhibition in the experiment as described in Example 12. In addition, fluorescence intensity monitoring as a function of time after addition of cell lysate showed a significant increase in fluorescence intensity initially but after 15 minutes this initial intensity level stabilized. Recalling that there was no substrate cleavage by the proteases present in the cell lysate, the best explanation of this initial fluorescence intensity is due to the DEVN substrate binding to the protease and the substrate undergoing a conformational change. This conformational change involving the substrate's backbone also affects the conformation of two covalently attached fluorescent dye molecules with respect to each other in terms of mean distance and relative orientation. The degree of fluorescence quenching of these two fluorophores in the substrate structure has been found to be sensitive to their distance and the specific orientation with respect to their dipoles. Hence, any conformational change that affects these two aspects of the fluorescence reporting molecules would be expected to affect the fluorescence quenching as well. Thus, conformational changes induced by a substrate binding to a protease's substrate binding site is reflected in the observed initial fluorescence intensity changes, i.e., an increase in its fluorescence intensity. Since the substrate cannot be cleaved, the initial fluorescence intensity increase levels off. One can utilize this observed fluorescence intensity increase due to conformational change of the substrate rather than substrate cleavage as a new kind of readout such as degree of association between the substrate and its target binding molecule.

Example 14

Variation of Hydrolysis Rates Induced by Varying the Flexibility of the Protease Recognition Domain by Various Conformation Determining Domain (CDR) Amino Acid Sequences Protease cleavage sites of physiologically relevant substrates for any give protease may be classified into two cases. One is the serine protease inhibitors such as neutrophil elastase inhibitor or alpha 1 antitrypsin where the elastase recognition sequence is rather rigidly held by the remaining inhibitor molecule. Upon cleavage by elastase, this protease reactive site and its newly formed terminal residues undergoes significant conformational change as evidenced by high resolution crystallographic structural analyses of reactive and cleaved inhibitor structures. In the second class of protease cleavage sites the cleavage sequences are in domains where conformations are not well defined or there is a significant amount of flexibility, as much as in free linear peptides. It is said that some degree of defined conformation or a less than maximally available backbone flexibility difference between two potential substrates results in a given protease's preference for one substrate over another.

Compounds 4 (Fm-DEVD), 10 (Fm-G2D2D), and 11 (Fm-CGD2D) illustrate how one can introduce varying amount of constrained conformational space or flexibility into a given substrate with the same protease recognition domain but with different conformation determining domains or regions (CDRs) while retaining the bent forming function of the CDRs. This example illustrates how one can vary relative rigidity or flexibility of the central protease recognition domain by changing the CDR's conformational flexibility or rigidity.

The parent compound Fm-DEVD has the following composition: Fmoc-K[F1]DBDEVDGIDPK[F1]GY (SEQ ID NO:234). The bold face underlined letters are the protease recognition sequence consisting of 7 amino acid residues. Compound #10 contains two glycine extensions at both ends of this protease recognition sequence. The central protease recognition domain now is 8 residues long GDEVDGID (SEQ ID NO:235), since the glycine residue at the amino terminus is a part of native sequence. The two glycine residues which are inherently more flexible than other amino acids, e.g., alanine, provide less conformational constraint or, conversely, more flexibility than compound 4 (Table 6 thereby permit greater flexion when combined with Aib or Pro residues. Additional insertion of amino caproic acid at both termini with five methylene groups in addition to the one present in glycine provides further relaxation of the constrained conformation and, thus, greater flexibility for the protease recognition domain, GDEVDGID (SEQ ID NO:236). This progression of flexibility resulted in an increased hydrolysis rate with the CPP32 protease since CPP32 recognizes a more flexible protease recognition domain than does elastase. Support for this statement is that the CPP32 protease cleavage site in the proform of its physiological substrate, poly(ADP-ribose) polymerase, PARP, is located between two well-folded domains. . In addition, the cleavage site within the inactive proform of CPP32 which is a member of proteases family called caspases by another caspase family member protease, caspase-8, has been shown to localized between the two folded domains of CPP32 called p17 and p12. Hence, it is expected that such a protease cleavage site would not be rigidly held or its conformation would be expected to be less defined than the remaining molecule. In order to provide these structural features to the substrate, introduction of flexible residues such as glycine, epsilon amino caproic acid, beta alanine, and amino butyric acid would be expected to play important roles in regulating the backbone flexibility of the substrates central protease recognition domain. These additional preferred residues for the conformation determining domain are also expected to provide the needed bend-inducing influence.

The observed varied hydrolysis rates for these three substrates point to success in regulating the flexibilities of the protease recognition domains. This is reflected in the observed difference in proteolysis rates while maintaining the appropriate orientation for the two fluorophores to interact with each other through space. The importance of this conformation determining domain in providing a means to regulate flexibility as well as allowing the amino and carboxyl termini to orient in space appropriately close is exemplified by these compounds (4, 10, and 11).

These examples provide a tetrapeptide and a pentapeptide comprising Lys-Asp-Aib-Gly (SEQ ID NO:237) or Lys-Asp-Aib-Ahx-Gly (SEQ ID NO:238) where Ahx is episilon amino caproic acid (i.e. $NH_2$—$(CH_2)_5$—COOH). The fluorophore is attached to episilon amino group of the lysine residue. The carboxyl terminal CDR domain is defined as a tripeptide Gly-Pro-Lys and a tetrapeptide Gly-Ahx-Pro-Lys (SEQ ID NO:239). The hydrolysis rate was increased by 3-fold between compounds 4 (Fm-DEVD: Fm-K[F1]DBDEVDGIDPK[F1]GY (SEQ ID NO:240)) and 10 (Fm-G2D2D: Fm-K[F1]DBGDEVDGIDGPK[F1]GY] (SEQ ID NO:241))

As illustrated in FIG. 5, the hydrolysis rate was further increased by ca. 3-fold over the above glycine residue insertion with the amino caproic amino acid (Ahx) addition, compound 11 (Fm-CGD2D: Fm-K[F1]DB Ahx GDEVDG-IDG Ahx PK[F1]GY, (SEQ ID NO:242). Hence, overall at least a 9-fold increase in substrate hydrolysis rate was accomplished (compounds 4 and 11, Table 6).

Example 15

Structural Characteristics of Fluorophores which Form Intramolecular H-type Dimers in a Protease Substrate The strongest correlations between H-dimer formation and structural elements of various potential fluorophores for use in the homo-doubly labeled fluorogenic compositions of this invention are in order: delocalized charge, symmetry, and transition dipole magnitude. Hydrophobicity was not observed to be a major determinant in this type of dimerization.

In the experiments described herein, a new class of profluorescent protease substrate was designed and synthesized. These new fluorogenic indicators have spectral properties that fit the exciton model; More specifically, spectra of these polypeptides which were doubly labeled with rhodamines showed a blue-shifted absorption peak and fluorescence quenching, both indicators of H-dimer formation.

For example, NorFes, an undecapeptide which is cleaved by the serine protease elastase, was homodoubly labeled on opposite sides of its cleavage site with six fluorophores in order to identify structural elements of dyes which influence intramolecular H-type dimer formation. Absorption and fluorescence spectra of these six substrate obtained before and after enzymatic cleavage suggest that the presence of a delocalized charge in the intramolecular dimer followed by symmetry and then magnitude of the transition dipole are important factors in dimer formation. Surprisingly, there was no evidence that hydrophobic interactions were important in the fluorophores used in this study.

The six fluorophores used in this study were rhodamine-X, tetramethylrhodamine, fluorescein, diethylaminocoumarin, hydroxycoumarin and pyrene.

While the xanthene components of these two rhodamines (rhodamine-X, tetramethylrhodamine) have the same charge and symmetric structure, the distinguishing characteristics between them are a higher transition dipole magnitude and lower hydrophobicity of the tetramethylrhodamine. One notes that the spectrum of the intact tetramethylrhodamine-derivatized substrate shows a more prominent change than that of rhodamine-X when comparing the absorption spectra of the two doubly-labeled intact peptides with those from the respective cleaved solution.

As noted above, in contrast to the two rhodamine derivatives where a charge of +1 is localized over each of the xanthene structure, the three conjugated ring component of the fluorescein was not positively charged at pH 9. The lack of any significant shape changes in the absorption spectra after separation of the dyes (fluorescein) by cleavage of the peptide suggests a role for positive charge in xanthene H-dimer formation. The less pronounced, but nevertheless finite quenching observed with this derivative points toward a diminished but finite degree of interaction between two fluoresceins compared with interactions between either of the two rhodamines is consistent with previous studies of xanthene in solution where the association constant for dimer formation for fluorescein is four order of magnitude lower than that for rhodamines.

The influence of dye symmetry was next examined using two coumarins, i.e. diethylaminocoumarin and hydroxycoumarin. This class of molecules contains no symmetrical elements. The diethylaminocoumarin bears a positive charge delocalized over its two conjugated rings, similar to the rhodamines and the hydroxycoumarin is neutral at pH 9, similar to fluorescein. The spectrum of diethylaminocoumarin-labeled NorFes exhibits a blue shift of 11 nm while that of hydroxycoumarin-labeled NorFes shows just a slight blue shoulder. The respective degree of quenching, 76% and 28% of the intact peptides relative to the cleaved solutions is consistent with the importance of delocalized charge. Comparing the less pronounced spectral changes of the diethylaminocoumarin-derivatized peptide with those of the xanthene gives support to the role of symmetry as an important element in H-dimer formation.

Finally, the role of hydrophobicity was studied using pyrene, a fluorophore with S2 symmetry containing only carbons and hydrogens. No spectral changes were observed in either the absorption or the fluorescence mode and the magnitude of the transition dipole is extremely small. These results provide evidence against a dominant role for hydrophobicity in H-dimer formation.

In summary, the strongest correlations between H-dimer formation and structural elements are in order: delocalized charge, symmetry, and transition dipole magnitude. Hydrophobicity was not observed to be a major determinant in this type of dimerization.

Example 16

High Throughput Screening

When the indicators of this invention utilize fluorescent molecules that emit at a wavelength ranging from about 650 nm to about 720 nm, they are well suited for use in a variety of instruments suitable for high-throughput screening. One such instrument is the Perkin Elmer Applied Biosystems FMAT™ System 8100 automated, macro-confocal high-throughput screening (HTS) system for fluorescent, homogeneous, multiplexed, live cell- and bead-based screening assays.

Cells were plated at a density of between 3 and $15 \times 10^3$ cells per well in a 96-well flat-bottomed plate. One population of cells was incubated with an apoptosis inducing agent, e.g., staurosporine at a concentration of ca. 1 $\mu$M for ca. 3–4 hours, and a second was treated with the vehicle, e.g., DMSO, for an equal time. Following the induction period, PhiPhiLux (Oncolmmunin, Inc.) cell permeable fluorogenic substrate comprising two IC5 fluorophores, was added at a final concentration of ca. 2 $\mu$M. Incubation was carried out for 1 hour. The plate was placed in an FMAT™ 8100 instrument and the number of fluorescent cells in each well was counted.

In preferred embodiments, the system simply was used "as is" by turning down the gain on the photomultiplier tube (reducing detector sensitivity) until a desirable signal to background level was obtained.

Other modifications to the FMAT™ 8100 to enhance the utility of this instrument, particularly for detection of intracellular protease activity using the indicators of this invention can be made. In one modification, the machine is modified to permit the introduction of a neutral density filter at the emission side to reduce the total emission signal provided by the fluorescence indicator. This allows the detector to be run without a decrease in sensitivity. A continuously variable filter stepped filters (e.g. in a filter wheel) allow the appropriate degree of signal reduction to be selected.

A variable pin hole can be provided rather than the fixed pin hole in the FMAT™ to permit selection of optical section thickness. The current instrument utilizes a fixed 100 $\mu$m optical section. A preferred thickness range would be from 0.1 $\mu$M to 100 $\mu$m, and for use with the indicators of this invention, an optical section thickness of about 10 to 20 $\mu$m is most preferred.

The introduction of an option for bright field and/or phase contract image capture permits one to switch between imaging the protease indicator signal and the cell. This facilitates determination of the total cell number within the field.

Increasing the magnification settings on the FMAT allows one to capture subcelluar localized images rather than low resolution whole cell images. This facilitates localization of protease activities to particular subcellular organelles or domains.

Introduction of UV laser excitation option along with the existing helium-neon laser permits the use of existing nuclear stains such as Hoechst dye to count the nucleus and thereby facilitate cell counting.

Modifications to the image analysis software accompanying the FMAT™ 8100 can also be made. For example, the software can be modified to permit grouping one or more subpopulation groups by applying various measured parameters such as particular feature shape, brightness, size, the existence of particular labels, and the like. This allows, for example, correlation of the enzyme activity with one or more physiological parameters or markers.

Modification of the software for real-time captured image analysis allows counting of cell number or number of subcellular features thereby permitting the device to normal its data acquisition protocols.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference for all purposes.

What is claimed is:

1. A mammalian cell comprising a fluorogenic composition comprising a polypeptide backbone joining two identical fluorophores whereby said fluorophores form an H-dimer resulting in the quenching of the fluorescence of said fluorophores.

2. The cell of claim 1, wherein said fluorophores are linked to the polypeptide backbone by linkers.

3. The cell of claim 1, wherein said fluorophores have an excitation wavelength between about 315 nm and about 700 nm.

4. The cell of claim 1, wherein said fluorophores are selected from the group consisting of carboxytetramethylrhodamine, carboxyrhodamine-X, carboxyrhodamine 110, diethylaminocoumarin, and carbocyanine dyes.

5. The cell of claim 4, wherein said fluorophores are carboxytetramethylrhodamine.

6. The cell of claim 4, wherein said fluorophores are carboxyrhodamine-X.

7. The cell of claim 4, wherein said fluorophores are carboxyrhodamine 110.

8. The cell of claim 4, wherein said fluorophores are diethylaminocoumarin.

9. The cell of claim 4, wherein said fluorophores are carbocyanine dyes.

10. The cell of claim 1, wherein said polypeptide backbone comprises a protease cleavage site.

11. The cell of claims 4, wherein said fluorophores are xanthenes.

12. A mammalian cell comprising a fluorogenic composition comprising a polypeptide backbone joining two fluorophores of the same species, wherein said fluorophores are xanthenes, whereby said fluorophores form an H-dimer resulting in the quenching of the fluorescence of said fluorophores.

13. A mammalian cell comprising a fluorogenic composition comprising a polypeptide backbone joining two fluorophores of the same species, wherein said fluorophores are carbocyanine dyes, whereby said fluorophores form an H-dimer resulting in the quenching of the fluorescence of said fluorophores.

14. The cell of claims 1, 10, 12, 13, wherein said composition bears a hydrophobic group.

15. The cell of claim 14, wherein said hydrophobic group is selected from the group consisting of: Fmoc (9-fluorenylmethoxycarbonyl), 9-fluoreneacetyl group, 1-fluorenecarboxylic group, 9-florenecarboxylic group, and 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4'-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), Benzyloxymethyl (Bom), t-butoxycarbonyl (Boc), cyclohexyloxy (cHxO), t-butoxymethyl (Bum), t-butoxy (tBuO), t-Butyl (tBu), Acetyl (Ac), and Trifluoroacetyl (TFA).

16. The cell of claim 14, wherein said hydrophobic group is Fmoc (9-fluorenylmethoxycarbonyl).

17. The cell of claim 14, wherein said hydrophobic group is Fa (9-fluoreneacetyl group).

18. The cell of claim 14, wherein said hydrophobic group is attached to an amino terminus of the polypeptide.

* * * * *

SEQUENCE LISTING

```
<160> NUMBER OF SEQ ID NOS: 246

<210> SEQ ID NO 1
<211> LENGTH: 9
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (5)..(5)
<223> OTHER INFORMATION: Xaa is norleucine

<400> SEQUENCE: 1

Asp Ala Ile Pro Xaa Ser Ile Pro Cys
1               5

<210> SEQ ID NO 2
<211> LENGTH: 5
<212> TYPE: PRT
<213> ORGANISM: Artificial
<220> FEATURE:
<223> OTHER INFORMATION: Synthetic peptide.

<400> SEQUENCE: 2

Ile Pro Met Ser Ile
1               5

<210> SEQ ID NO 3
<211> LENGTH: 4
<212> TYPE: PRT
<213> ORGANISM: Artificial
<220> FEATURE:
<223> OTHER INFORMATION: Synthetic peptide.

<400> SEQUENCE: 3

Pro Met Ser Ile
1

<210> SEQ ID NO 4
<211> LENGTH: 4
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (2)..(2)
<223> OTHER INFORMATION: Xaa is norleucine

<400> SEQUENCE: 4
```

```
Pro Xaa Ser Ile
1

<210> SEQ ID NO 5
<211> LENGTH: 9
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa is Pro or alpha-aminoisobutyric acid
<220> FEATURE:
<221> NAME/KEY: misc_feature
<222> LOCATION: (9)..(9)
<223> OTHER INFORMATION: Xaa is Cys or Lys

<400> SEQUENCE: 5

Asp Ala Ile Pro Xaa Ser Ile Xaa Xaa
1               5

<210> SEQ ID NO 6
<211> LENGTH: 9
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (2)..(2)
<223> OTHER INFORMATION: Xaa is Met, alpha-aminoisobutyric acid, or Pro
<220> FEATURE:
<221> NAME/KEY: misc_feature
<222> LOCATION: (3)..(3)
<223> OTHER INFORMATION: Xaa is Thr, alpha-aminoisobutyric acid, or Pro
<220> FEATURE:
<221> NAME/KEY: misc_feature
<222> LOCATION: (8)..(8)
<223> OTHER INFORMATION: Xaa is Pro or alpha-aminoisobutyric acid
<220> FEATURE:
<221> NAME/KEY: misc_feature
<222> LOCATION: (9)..(9)
<223> OTHER INFORMATION: Xaa is Cys or Lys

<400> SEQUENCE: 6

Asp Xaa Xaa Gly Arg Thr Gly Xaa Xaa
1               5

<210> SEQ ID NO 7
<211> LENGTH: 9
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (2)..(2)
<223> OTHER INFORMATION: Xaa is alpha-aminoisobutyric acid or Ala
<220> FEATURE:
<221> NAME/KEY: misc_feature
<222> LOCATION: (3)..(3)
<223> OTHER INFORMATION: Xaa is Thr, alpha-aminoisobutyric acid, or Pro
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
```

```
<222> LOCATION: (8)..(8)
<223> OTHER INFORMATION: Xaa is Pro or alpha-aminoisobutyric acid
<220> FEATURE:
<221> NAME/KEY: misc_feature
<222> LOCATION: (9)..(9)
<223> OTHER INFORMATION: Xaa is Cys or Lys

<400> SEQUENCE: 7

Asp Xaa Xaa Phe Cys Xaa Leu Xaa Xaa
1               5

<210> SEQ ID NO 8
<211> LENGTH: 9
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (2)..(2)
<223> OTHER INFORMATION: Xaa is alpha-aminoisobutyric acid
<220> FEATURE:
<221> NAME/KEY: misc_feature
<222> LOCATION: (3)..(3)
<223> OTHER INFORMATION: Xaa is Ser, alpha-aminoisobutyric acid, or Pro
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa is Pro or alpha-aminoisobutyric acid
<220> FEATURE:
<221> NAME/KEY: misc_feature
<222> LOCATION: (9)..(9)
<223> OTHER INFORMATION: Xaa is Cys or Lys

<400> SEQUENCE: 8

Asp Xaa Xaa Arg Xaa Ser Leu Xaa Xaa
1               5

<210> SEQ ID NO 9
<211> LENGTH: 9
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (2)..(2)
<223> OTHER INFORMATION: Xaa is alpha-aminoisobutyric acid, or Ile
<220> FEATURE:
<221> NAME/KEY: misc_feature
<222> LOCATION: (3)..(3)
<223> OTHER INFORMATION: Xaa is Ala, alpha-aminoisobutyric acid, or Pro
<220> FEATURE:
<221> NAME/KEY: misc_feature
<222> LOCATION: (8)..(8)
<223> OTHER INFORMATION: Xaa is Pro or alpha-aminoisobutyric acid
<220> FEATURE:
<221> NAME/KEY: misc_feature
<222> LOCATION: (9)..(9)
<223> OTHER INFORMATION: Xaa is Cys or Lys

<400> SEQUENCE: 9

Asp Xaa Xaa Gly Arg Ser Leu Xaa Xaa
1               5

<210> SEQ ID NO 10
<211> LENGTH: 9
<212> TYPE: PRT
<213> ORGANISM: Artificial
```

-continued

<220> FEATURE:
<223> OTHER INFORMATION: Synthetic peptide.
<220> FEATURE:
<221> NAME/KEY: misc_feature
<222> LOCATION: (2)..(2)
<223> OTHER INFORMATION: Xaa is alpha-aminoisobutyric acid
<220> FEATURE:
<221> NAME/KEY: misc_feature
<222> LOCATION: (3)..(3)
<223> OTHER INFORMATION: Xaa is Thr, alpha-aminoisobutyric acid, or Pro
<220> FEATURE:
<221> NAME/KEY: misc_feature
<222> LOCATION: (8)..(8)
<223> OTHER INFORMATION: Xaa is Pro or alpha-aminoisobutyric acid
<220> FEATURE:
<221> NAME/KEY: misc_feature
<222> LOCATION: (9)..(9)
<223> OTHER INFORMATION: Xaa is Cys or Lys

<400> SEQUENCE: 10

```
Asp Xaa Xaa Leu Leu Ser Leu Xaa Xaa
1               5
```

<210> SEQ ID NO 11
<211> LENGTH: 9
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (2)..(2)
<223> OTHER INFORMATION: Xaa is alpha-aminoisobutyric acid, or Gly
<220> FEATURE:
<221> NAME/KEY: misc_feature
<222> LOCATION: (3)..(3)
<223> OTHER INFORMATION: Xaa is alpha-aminoisobutyric acid, or Pro
<220> FEATURE:
<221> NAME/KEY: misc_feature
<222> LOCATION: (8)..(8)
<223> OTHER INFORMATION: Xaa is Pro or alpha-aminoisobutyric acid
<220> FEATURE:
<221> NAME/KEY: misc_feature
<222> LOCATION: (9)..(9)
<223> OTHER INFORMATION: Xaa is Cys or Lys

<400> SEQUENCE: 11

```
Asp Xaa Xaa Leu Gly Ile Ala Xaa Xaa
1               5
```

<210> SEQ ID NO 12
<211> LENGTH: 9
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (2)..(2)
<223> OTHER INFORMATION: Xaa is alpha-aminoisobutyric acid, Gly, or Pro
<220> FEATURE:
<221> NAME/KEY: misc_feature
<222> LOCATION: (3)..(3)
<223> OTHER INFORMATION: Xaa is alpha-aminoisobutyric acid, or Pro
<220> FEATURE:
<221> NAME/KEY: misc_feature
<222> LOCATION: (8)..(8)
<223> OTHER INFORMATION: Xaa is Pro or alpha-aminoisobutyric acid
<220> FEATURE:
<221> NAME/KEY: misc_feature
<222> LOCATION: (9)..(9)
<223> OTHER INFORMATION: Xaa is Cys or Lys

<400> SEQUENCE: 12

```
Asp Xaa Xaa Gln Gly Ile Leu Xaa Xaa
1               5
```

<210> SEQ ID NO 13
<211> LENGTH: 9
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (2)..(2)
<223> OTHER INFORMATION: Xaa is alpha-aminoisobutyric acid, Pro, or Gly
<220> FEATURE:
<221> NAME/KEY: misc_feature
<222> LOCATION: (3)..(3)
<223> OTHER INFORMATION: Xaa is alpha-aminoisobutyric acid, or Pro
<220> FEATURE:
<221> NAME/KEY: misc_feature
<222> LOCATION: (8)..(8)
<223> OTHER INFORMATION: Xaa is Pro or alpha-aminoisobutyric acid
<220> FEATURE:
<221> NAME/KEY: misc_feature
<222> LOCATION: (9)..(9)
<223> OTHER INFORMATION: Xaa is Cys or Lys

<400> SEQUENCE: 13

```
Asp Xaa Xaa Gln Gly Leu Leu Xaa Xaa
1               5
```

<210> SEQ ID NO 14
<211> LENGTH: 9
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (2)..(2)
<223> OTHER INFORMATION: Xaa is alpha-aminoisobutyric acid, , Gly, or
      Pro
<220> FEATURE:
<221> NAME/KEY: misc_feature
<222> LOCATION: (3)..(3)
<223> OTHER INFORMATION: Xaa is alpha-aminoisobutyric acid, or Pro
<220> FEATURE:
<221> NAME/KEY: misc_feature
<222> LOCATION: (8)..(8)
<223> OTHER INFORMATION: Xaa is Pro or alpha-aminoisobutyric acid
<220> FEATURE:
<221> NAME/KEY: misc_feature
<222> LOCATION: (9)..(9)
<223> OTHER INFORMATION: Xaa is Cys or Lys

<400> SEQUENCE: 14

```
Asp Xaa Xaa Gln Gly Ile Ala Xaa Xaa
1               5
```

<210> SEQ ID NO 15
<211> LENGTH: 9
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (2)..(2)
<223> OTHER INFORMATION: Xaa is alpha-aminoisobutyric acid, Gly, or Pro
<220> FEATURE:
<221> NAME/KEY: misc_feature
<222> LOCATION: (3)..(3)
<223> OTHER INFORMATION: Xaa is alpha-aminoisobutyric acid, or Pro
<220> FEATURE:
<221> NAME/KEY: misc_feature

```
<222> LOCATION: (8)..(8)
<223> OTHER INFORMATION: Xaa is Pro or alpha-aminoisobutyric acid
<220> FEATURE:
<221> NAME/KEY: misc_feature
<222> LOCATION: (9)..(9)
<223> OTHER INFORMATION: Xaa is Cys or Lys

<400> SEQUENCE: 15

Asp Xaa Xaa Gln Ala Ile Ala Xaa Xaa
1               5

<210> SEQ ID NO 16
<211> LENGTH: 9
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (2)..(2)
<223> OTHER INFORMATION: Xaa is alpha-aminoisobutyric acid, Gly, or Pro
<220> FEATURE:
<221> NAME/KEY: misc_feature
<222> LOCATION: (3)..(3)
<223> OTHER INFORMATION: Xaa is alpha-aminoisobutyric acid, or Pro
<220> FEATURE:
<221> NAME/KEY: misc_feature
<222> LOCATION: (8)..(8)
<223> OTHER INFORMATION: Xaa is Pro or alpha-aminoisobutyric acid
<220> FEATURE:
<221> NAME/KEY: misc_feature
<222> LOCATION: (9)..(9)
<223> OTHER INFORMATION: Xaa is Cys or Lys

<400> SEQUENCE: 16

Asp Xaa Xaa Gln Gly Ile Ala Xaa Xaa
1               5

<210> SEQ ID NO 17
<211> LENGTH: 9
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (2)..(2)
<223> OTHER INFORMATION: Xaa is alpha-aminoisobutyric acid, Gly, or Pro
<220> FEATURE:
<221> NAME/KEY: misc_feature
<222> LOCATION: (3)..(3)
<223> OTHER INFORMATION: Xaa is alpha-aminoisobutyric acid, or Pro
<220> FEATURE:
<221> NAME/KEY: misc_feature
<222> LOCATION: (8)..(8)
<223> OTHER INFORMATION: Xaa is Pro or alpha-aminoisobutyric acid
<220> FEATURE:
<221> NAME/KEY: misc_feature
<222> LOCATION: (9)..(9)
<223> OTHER INFORMATION: Xaa is Cys or Lys

<400> SEQUENCE: 17

Asp Xaa Xaa Glu Gly Leu Arg Xaa Xaa
1               5

<210> SEQ ID NO 18
<211> LENGTH: 9
<212> TYPE: PRT
<213> ORGANISM: Artificial
<220> FEATURE:
<223> OTHER INFORMATION: Synthetic peptide.
<220> FEATURE:
<221> NAME/KEY: misc_feature
```

```
<222> LOCATION: (2)..(2)
<223> OTHER INFORMATION: Xaa is alpha-aminoisobutyric acid, Asp, or Pro
<220> FEATURE:
<221> NAME/KEY: misc_feature
<222> LOCATION: (3)..(3)
<223> OTHER INFORMATION: Xaa is Val, alpha-aminoisobutyric acid, or Pro
<220> FEATURE:
<221> NAME/KEY: misc_feature
<222> LOCATION: (8)..(8)
<223> OTHER INFORMATION: Xaa is Pro or alpha-aminoisobutyric acid
<220> FEATURE:
<221> NAME/KEY: misc_feature
<222> LOCATION: (9)..(9)
<223> OTHER INFORMATION: Xaa is Cys or Lys

<400> SEQUENCE: 18

Asp Xaa Xaa Gly His Phe Arg Xaa Xaa
1               5

<210> SEQ ID NO 19
<211> LENGTH: 9
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (2)..(2)
<223> OTHER INFORMATION: Xaa is alpha-aminoisobutyric acid, Asp, or Pro
<220> FEATURE:
<221> NAME/KEY: misc_feature
<222> LOCATION: (3)..(3)
<223> OTHER INFORMATION: Xaa is Thr, alpha-aminoisobutyric acid, or Pro
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa is Pro or alpha-aminoisobutyric acid
<220> FEATURE:
<221> NAME/KEY: misc_feature
<222> LOCATION: (9)..(9)
<223> OTHER INFORMATION: Xaa is Cys or Lys

<400> SEQUENCE: 19

Asp Xaa Xaa Leu Glu Val Xaa Xaa Xaa
1               5

<210> SEQ ID NO 20
<211> LENGTH: 9
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (2)..(2)
<223> OTHER INFORMATION: Xaa is alpha-aminoisobutyric acid, Arg, or Pro
<220> FEATURE:
<221> NAME/KEY: misc_feature
<222> LOCATION: (3)..(3)
<223> OTHER INFORMATION: Xaa is Alal, alpha-aminoisobutyric acid, or Pro
<220> FEATURE:
<221> NAME/KEY: misc_feature
<222> LOCATION: (8)..(8)
<223> OTHER INFORMATION: Xaa is Pro or alpha-aminoisobutyric acid
<220> FEATURE:
<221> NAME/KEY: misc_feature
<222> LOCATION: (9)..(9)
<223> OTHER INFORMATION: Xaa is Cys or Lys

<400> SEQUENCE: 20
```

-continued

```
Asp Xaa Xaa Ile His Ile Gln Xaa Xaa
1               5

<210> SEQ ID NO 21
<211> LENGTH: 9
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (2)..(2)
<223> OTHER INFORMATION: Xaa is alpha-aminoisobutyric acid, Asp, or Pro
<220> FEATURE:
<221> NAME/KEY: misc_feature
<222> LOCATION: (3)..(3)
<223> OTHER INFORMATION: Xaa is Val, alpha-aminoisobutyric acid, or Pro
<220> FEATURE:
<221> NAME/KEY: misc_feature
<222> LOCATION: (8)..(8)
<223> OTHER INFORMATION: Xaa is Pro or alpha-aminoisobutyric acid
<220> FEATURE:
<221> NAME/KEY: misc_feature
<222> LOCATION: (9)..(9)
<223> OTHER INFORMATION: Xaa is Cys or Lys

<400> SEQUENCE: 21

Asp Xaa Xaa Ala Asn Tyr Asn Xaa Xaa
1               5

<210> SEQ ID NO 22
<211> LENGTH: 9
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (2)..(2)
<223> OTHER INFORMATION: Xaa is alpha-aminoisobutyric acid, Gly, or Pro
<220> FEATURE:
<221> NAME/KEY: misc_feature
<222> LOCATION: (3)..(3)
<223> OTHER INFORMATION: Xaa is alpha-aminoisobutyric acid, or Pro
<220> FEATURE:
<221> NAME/KEY: misc_feature
<222> LOCATION: (8)..(8)
<223> OTHER INFORMATION: Xaa is Pro or alpha-aminoisobutyric acid
<220> FEATURE:
<221> NAME/KEY: misc_feature
<222> LOCATION: (9)..(9)
<223> OTHER INFORMATION: Xaa is Cys or Lys

<400> SEQUENCE: 22

Asp Xaa Xaa Ala Gly Glu Arg Xaa Xaa
1               5

<210> SEQ ID NO 23
<211> LENGTH: 9
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (2)..(22)
<223> OTHER INFORMATION: Xaa is alpha-aminoisobutyric acid, Gly, or Pro
<220> FEATURE:
<221> NAME/KEY: misc_feature
<222> LOCATION: (3)..(3)
<223> OTHER INFORMATION: Xaa is alpha-aminoisobutyric acid, or Pro
<220> FEATURE:
<221> NAME/KEY: misc_feature
<222> LOCATION: (8)..(8)
```

```
<223> OTHER INFORMATION: Xaa is Pro or alpha-aminoisobutyric acid
<220> FEATURE:
<221> NAME/KEY: misc_feature
<222> LOCATION: (9)..(9)
<223> OTHER INFORMATION: Xaa is Cys or Lys

<400> SEQUENCE: 23

Asp Xaa Xaa Ala Gly Phe Ala Xaa Xaa
1               5

<210> SEQ ID NO 24
<211> LENGTH: 9
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (2)..(2)
<223> OTHER INFORMATION: Xaa is alpha-aminoisobutyric acid, Gly, or Pro
<220> FEATURE:
<221> NAME/KEY: misc_feature
<222> LOCATION: (3)..(3)
<223> OTHER INFORMATION: Xaa is  alpha-aminoisobutyric acid, or Pro
<220> FEATURE:
<221> NAME/KEY: misc_feature
<222> LOCATION: (8)..(8)
<223> OTHER INFORMATION: Xaa is Pro or alpha-aminoisobutyric acid
<220> FEATURE:
<221> NAME/KEY: misc_feature
<222> LOCATION: (9)..(9)
<223> OTHER INFORMATION: Xaa is Cys or Lys

<400> SEQUENCE: 24

Asp Xaa Xaa Gln Gly Leu Ala Xaa Xaa
1               5

<210> SEQ ID NO 25
<211> LENGTH: 9
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (2)..(2)
<223> OTHER INFORMATION: Xaa is alpha-aminoisobutyric acid, Asp, or Pro
<220> FEATURE:
<221> NAME/KEY: misc_feature
<222> LOCATION: (3)..(3)
<223> OTHER INFORMATION: Xaa is Val, alpha-aminoisobutyric acid, or Pro
<220> FEATURE:
<221> NAME/KEY: misc_feature
<222> LOCATION: (8)..(8)
<223> OTHER INFORMATION: Xaa is Pro or alpha-aminoisobutyric acid
<220> FEATURE:
<221> NAME/KEY: misc_feature
<222> LOCATION: (9)..(9)
<223> OTHER INFORMATION: Xaa is Cys or Lys

<400> SEQUENCE: 25

Asp Xaa Xaa Ala Gln Phe Val Xaa Xaa
1               5

<210> SEQ ID NO 26
<211> LENGTH: 9
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (2)..(2)
```

<223> OTHER INFORMATION: Xaa is alpha-aminoisobutyric acid, Asp, or Pro
<220> FEATURE:
<221> NAME/KEY: misc_feature
<222> LOCATION: (3)..(3)
<223> OTHER INFORMATION: Xaa is Glyl, alpha-aminoisobutyric acid, or Pro
<220> FEATURE:
<221> NAME/KEY: misc_feature
<222> LOCATION: (8)..(8)
<223> OTHER INFORMATION: Xaa is Pro or alpha-aminoisobutyric acid
<220> FEATURE:
<221> NAME/KEY: misc_feature
<222> LOCATION: (9)..(9)
<223> OTHER INFORMATION: Xaa is Cys or Lys

<400> SEQUENCE: 26

Asp Xaa Xaa His Phe Leu Arg Xaa Xaa
1               5

<210> SEQ ID NO 27
<211> LENGTH: 9
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (2)..(2)
<223> OTHER INFORMATION: Xaa is alpha-aminoisobutyric acid, Thr, or Pro
<220> FEATURE:
<221> NAME/KEY: misc_feature
<222> LOCATION: (3)..(3)
<223> OTHER INFORMATION: Xaa is Thrl, alpha-aminoisobutyric acid, or Pro
<220> FEATURE:
<221> NAME/KEY: misc_feature
<222> LOCATION: (8)..(8)
<223> OTHER INFORMATION: Xaa is Pro or alpha-aminoisobutyric acid
<220> FEATURE:
<221> NAME/KEY: misc_feature
<222> LOCATION: (9)..(9)
<223> OTHER INFORMATION: Xaa is Cys or Lys

<400> SEQUENCE: 27

Asp Xaa Xaa Glu Leu Phe Ser Xaa Xaa
1               5

<210> SEQ ID NO 28
<211> LENGTH: 9
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (2)..(2)
<223> OTHER INFORMATION: Xaa is alpha-aminoisobutyric acid, Lys, or Pro
<220> FEATURE:
<221> NAME/KEY: misc_feature
<222> LOCATION: (3)..(3)
<223> OTHER INFORMATION: Xaa is Phe, alpha-aminoisobutyric acid, or Pro
<220> FEATURE:
<221> NAME/KEY: misc_feature
<222> LOCATION: (8)..(8)
<223> OTHER INFORMATION: Xaa is Pro or alpha-aminoisobutyric acid
<220> FEATURE:
<221> NAME/KEY: misc_feature
<222> LOCATION: (9)..(9)
<223> OTHER INFORMATION: Xaa is Cys or Lys

<400> SEQUENCE: 28

Asp Xaa Xaa Leu Ala Phe Leu Xaa Xaa
1               5

<210> SEQ ID NO 29

```
<211> LENGTH: 9
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (2)..(2)
<223> OTHER INFORMATION: Xaa is alpha-aminoisobutyric acid, Phe, or Pro
<220> FEATURE:
<221> NAME/KEY: misc_feature
<222> LOCATION: (3)..(3)
<223> OTHER INFORMATION: Xaa is Ser, alpha-aminoisobutyric acid, or Pro
<220> FEATURE:
<221> NAME/KEY: misc_feature
<222> LOCATION: (8)..(8)
<223> OTHER INFORMATION: Xaa is Pro or alpha-aminoisobutyric acid
<220> FEATURE:
<221> NAME/KEY: misc_feature
<222> LOCATION: (9)..(9)
<223> OTHER INFORMATION: Xaa is Cys or Lys

<400> SEQUENCE: 29

Asp Xaa Xaa His Phe Val Arg Xaa Xaa
1               5

<210> SEQ ID NO 30
<211> LENGTH: 9
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (2)..(2)
<223> OTHER INFORMATION: Xaa is alpha-aminoisobutyric acid, Gln, or Pro
<220> FEATURE:
<221> NAME/KEY: misc_feature
<222> LOCATION: (3)..(3)
<223> OTHER INFORMATION: Xaa is Gln, alpha-aminoisobutyric acid, or Pro
<220> FEATURE:
<221> NAME/KEY: misc_feature
<222> LOCATION: (8)..(8)
<223> OTHER INFORMATION: Xaa is Pro or alpha-aminoisobutyric acid
<220> FEATURE:
<221> NAME/KEY: misc_feature
<222> LOCATION: (9)..(9)
<223> OTHER INFORMATION: Xaa is Cys or Lys

<400> SEQUENCE: 30

Asp Xaa Xaa Leu Leu His Asn Xaa Xaa
1               5

<210> SEQ ID NO 31
<211> LENGTH: 9
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (2)..(2)
<223> OTHER INFORMATION: Xaa is alpha-aminoisobutyric acid, Ser, or Pro
<220> FEATURE:
<221> NAME/KEY: misc_feature
<222> LOCATION: (3)..(3)
<223> OTHER INFORMATION: Xaa is Ile, alpha-aminoisobutyric acid, or Pro
<220> FEATURE:
<221> NAME/KEY: misc_feature
<222> LOCATION: (8)..(8)
<223> OTHER INFORMATION: Xaa is Pro or alpha-aminoisobutyric acid
<220> FEATURE:
<221> NAME/KEY: misc_feature
<222> LOCATION: (9)..(9)
<223> OTHER INFORMATION: Xaa is Cys or Lys
```

```
<400> SEQUENCE: 31

Asp Xaa Xaa Gln Tyr Thr Tyr Xaa Xaa
1               5

<210> SEQ ID NO 32
<211> LENGTH: 9
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (2)..(2)
<223> OTHER INFORMATION: Xaa is alpha-aminoisobutyric acid, Ser, or Pro
<220> FEATURE:
<221> NAME/KEY: misc_feature
<222> LOCATION: (3)..(3)
<223> OTHER INFORMATION: Xaa is Ser, alpha-aminoisobutyric acid, or Pro
<220> FEATURE:
<221> NAME/KEY: misc_feature
<222> LOCATION: (8)..(8)
<223> OTHER INFORMATION: Xaa is Pro or alpha-aminoisobutyric acid
<220> FEATURE:
<221> NAME/KEY: misc_feature
<222> LOCATION: (9)..(9)
<223> OTHER INFORMATION: Xaa is Cys or Lys

<400> SEQUENCE: 32

Asp Xaa Xaa Gln Tyr Ser Asn Xaa Xaa
1               5

<210> SEQ ID NO 33
<211> LENGTH: 9
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (2)..(2)
<223> OTHER INFORMATION: Xaa is alpha-aminoisobutyric acid, Ser, or Pro
<220> FEATURE:
<221> NAME/KEY: misc_feature
<222> LOCATION: (3)..(3)
<223> OTHER INFORMATION: Xaa is Ser, alpha-aminoisobutyric acid, or Pro
<220> FEATURE:
<221> NAME/KEY: misc_feature
<222> LOCATION: (8)..(8)
<223> OTHER INFORMATION: Xaa is Pro or alpha-aminoisobutyric acid
<220> FEATURE:
<221> NAME/KEY: misc_feature
<222> LOCATION: (9)..(9)
<223> OTHER INFORMATION: Xaa is Cys or Lys

<400> SEQUENCE: 33

Asp Xaa Xaa Ile Tyr Ser Gln Xaa Xaa
1               5

<210> SEQ ID NO 34
<211> LENGTH: 9
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (2)..(2)
<223> OTHER INFORMATION: Xaa is alpha-aminoisobutyric acid, Gly, or Pro
<220> FEATURE:
<221> NAME/KEY: misc_feature
<222> LOCATION: (3)..(3)
<223> OTHER INFORMATION: Xaa is alpha-aminoisobutyric acid, or Pro
```

```
<220> FEATURE:
<221> NAME/KEY: misc_feature
<222> LOCATION: (8)..(8)
<223> OTHER INFORMATION: Xaa is Pro or alpha-aminoisobutyric acid
<220> FEATURE:
<221> NAME/KEY: misc_feature
<222> LOCATION: (9)..(9)
<223> OTHER INFORMATION: Xaa is Cys or Lys

<400> SEQUENCE: 34

Asp Xaa Xaa Ala Gly Val Gln Xaa Xaa
1               5

<210> SEQ ID NO 35
<211> LENGTH: 4
<212> TYPE: PRT
<213> ORGANISM: Artificial
<220> FEATURE:
<223> OTHER INFORMATION: Synthetic peptide.

<400> SEQUENCE: 35

Gly Gly Gly Gly
1

<210> SEQ ID NO 36
<211> LENGTH: 12
<212> TYPE: PRT
<213> ORGANISM: Artificial
<220> FEATURE:
<223> OTHER INFORMATION: Synthetic peptide.

<400> SEQUENCE: 36

Lys Asp Asx Thr Gly Arg Thr Gly Pro Lys Gly Tyr
1               5                   10

<210> SEQ ID NO 37
<211> LENGTH: 14
<212> TYPE: PRT
<213> ORGANISM: Artificial
<220> FEATURE:
<223> OTHER INFORMATION: Synthetic peptide.

<400> SEQUENCE: 37

Lys Asp Pro Pro Thr Gly Arg Thr Gly Pro Pro Lys Gly Tyr
1               5                   10

<210> SEQ ID NO 38
<211> LENGTH: 14
<212> TYPE: PRT
<213> ORGANISM: Artificial
<220> FEATURE:
<223> OTHER INFORMATION: Synthetic peptide.

<400> SEQUENCE: 38

Lys Asp Asx Asp Glu Val Asp Gly Ile Asp Pro Lys Gly Tyr
1               5                   10

<210> SEQ ID NO 39
<211> LENGTH: 14
<212> TYPE: PRT
<213> ORGANISM: Artificial
<220> FEATURE:
<223> OTHER INFORMATION: Synthetic peptide.

<400> SEQUENCE: 39

Lys Asp Asx Asp Glu Val Asn Gly Ile Asp Pro Lys Gly Tyr
1               5                   10
```

```
<210> SEQ ID NO 40
<211> LENGTH: 13
<212> TYPE: PRT
<213> ORGANISM: Artificial
<220> FEATURE:
<223> OTHER INFORMATION: Synthetic peptide.

<400> SEQUENCE: 40

Lys Asp Asx Glu Val Asp Gly Ile Asp Pro Lys Gly Tyr
1               5                   10

<210> SEQ ID NO 41
<211> LENGTH: 13
<212> TYPE: PRT
<213> ORGANISM: Artificial
<220> FEATURE:
<223> OTHER INFORMATION: Synthetic peptide.

<400> SEQUENCE: 41

Lys Asp Tyr Asx Ala Asp Gly Ile Asp Pro Lys Gly Tyr
1               5                   10

<210> SEQ ID NO 42
<211> LENGTH: 14
<212> TYPE: PRT
<213> ORGANISM: Artificial
<220> FEATURE:
<223> OTHER INFORMATION: Synthetic peptide.

<400> SEQUENCE: 42

Lys Asp Asx Asp Glu Val Asp Gly Ile Asp Pro Lys Gly Tyr
1               5                   10

<210> SEQ ID NO 43
<211> LENGTH: 14
<212> TYPE: PRT
<213> ORGANISM: Artificial
<220> FEATURE:
<223> OTHER INFORMATION: Synthetic peptide.

<400> SEQUENCE: 43

Lys Asp Asx Asp Glu Val Asn Gly Ile Asp Pro Lys Gly Tyr
1               5                   10

<210> SEQ ID NO 44
<211> LENGTH: 13
<212> TYPE: PRT
<213> ORGANISM: Artificial
<220> FEATURE:
<223> OTHER INFORMATION: Synthetic peptide.

<400> SEQUENCE: 44

Lys Asp Asx Glu Val Asp Gly Ile Asp Pro Lys Gly Tyr
1               5                   10

<210> SEQ ID NO 45
<211> LENGTH: 12
<212> TYPE: PRT
<213> ORGANISM: Artificial
<220> FEATURE:
<223> OTHER INFORMATION: Synthetic peptide.

<400> SEQUENCE: 45

Lys Asp Ala Ile Pro Met Ser Ile Pro Lys Gly Tyr
1               5                   10
```

```
<210> SEQ ID NO 46
<211> LENGTH: 14
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (6)..(6)
<223> OTHER INFORMATION: Xaa is norleucine

<400> SEQUENCE: 46

Lys Asp Ala Ile Pro Xaa Ala Ala Ser Ile Pro Lys Gly Tyr
1               5                   10

<210> SEQ ID NO 47
<211> LENGTH: 16
<212> TYPE: PRT
<213> ORGANISM: Artificial
<220> FEATURE:
<223> OTHER INFORMATION: Synthetic peptide.

<400> SEQUENCE: 47

Lys Asp Asx Gly Asp Glu Val Asp Gly Ile Asp Gly Pro Lys Gly Tyr
1               5                   10                  15

<210> SEQ ID NO 48
<211> LENGTH: 17
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid

<400> SEQUENCE: 48

Lys Asp Asx Xaa Gly Asp Glu Val Asp Gly Ile Asp Gly Pro Lys Gly
1               5                   10                  15

Tyr

<210> SEQ ID NO 49
<211> LENGTH: 17
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid

<400> SEQUENCE: 49

Lys Asp Asx Xaa Gly Asp Glu Val Asp Gly Ile Asp Gly Pro Lys Gly
1               5                   10                  15

Tyr

<210> SEQ ID NO 50
<211> LENGTH: 13
<212> TYPE: PRT
<213> ORGANISM: Artificial
<220> FEATURE:
<223> OTHER INFORMATION: Synthetic peptide.

<400> SEQUENCE: 50

Lys Asp Tyr Asx Ala Asp Gly Ile Asp Pro Lys Gly Tyr
1               5                   10
```

<210> SEQ ID NO 51
<211> LENGTH: 18
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (14)..(14)
<223> OTHER INFORMATION: Xaa is episilon-aminocaproic acid

<400> SEQUENCE: 51

Lys Asp Pro Xaa Gly Asp Glu Val Asp Gly Ile Asn Gly Xaa Pro Lys
1               5                   10                  15

Gly Tyr

<210> SEQ ID NO 52
<211> LENGTH: 16
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (14)..(14)
<223> OTHER INFORMATION: Xaa is episilon-aminocaproic acid
<220> FEATURE:
<221> NAME/KEY: misc_feature
<222> LOCATION: (16)..(16)
<223> OTHER INFORMATION: K is blocked with amide

<400> SEQUENCE: 52

Lys Asp Pro Xaa Gly Asp Glu Val Asp Gly Ile Asn Gly Xaa Pro Xaa
1               5                   10                  15

<210> SEQ ID NO 53
<211> LENGTH: 19
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (6)..(6)
<223> OTHER INFORMATION: Xaa is tetrahydroisoquinoline-3-carboxylic
      acid.
<220> FEATURE:
<221> NAME/KEY: misc_feature
<222> LOCATION: (15)..(15)
<223> OTHER INFORMATION: Xaa is episilon-aminocaproic acid

<400> SEQUENCE: 53

Lys Asp Pro Xaa Gly Xaa Asp Glu Val Asp Gly Ile Asn Gly Xaa Pro
1               5                   10                  15

Lys Gly Tyr

<210> SEQ ID NO 54

```
<211> LENGTH: 17
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid

<400> SEQUENCE: 54

Lys Asp Pro Xaa Gly Asp Glu Val Asp Gly Ile Asn Gly Pro Lys Gly
1               5                   10                  15

Tyr

<210> SEQ ID NO 55
<211> LENGTH: 17
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (13)..(13)
<223> OTHER INFORMATION: Xaa is episilon-aminocaproic acid

<400> SEQUENCE: 55

Lys Asp Pro Gly Asp Glu Val Asp Gly Ile Asn Gly Xaa Pro Lys Gly
1               5                   10                  15

Tyr

<210> SEQ ID NO 56
<211> LENGTH: 16
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (14)..(14)
<223> OTHER INFORMATION: Xaa is episilon-aminocaproic acid
<220> FEATURE:
<221> NAME/KEY: misc_feature
<222> LOCATION: (16)..(16)
<223> OTHER INFORMATION: K is blocked with amide

<400> SEQUENCE: 56

Lys Asp Pro Xaa Gly Asp Glu Val Asp Gly Ile Asp Gly Xaa Pro Xaa
1               5                   10                  15

<210> SEQ ID NO 57
<211> LENGTH: 18
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (14)..(14)
<223> OTHER INFORMATION: Xaa is episilon-aminocaproic acid

<400> SEQUENCE: 57
```

```
Lys Asp Pro Xaa Gly Glu Glu Val Glu Gly Ile Asn Gly Xaa Pro Lys
1               5                   10                  15

Gly Tyr

<210> SEQ ID NO 58
<211> LENGTH: 18
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (7)..(7)
<223> OTHER INFORMATION: Xaa is D Phe
<220> FEATURE:
<221> NAME/KEY: misc_feature
<222> LOCATION: (14)..(14)
<223> OTHER INFORMATION: Xaa is episilon-aminocaproic acid

<400> SEQUENCE: 58

Lys Asp Pro Xaa Gly Asp Xaa Val Asp Gly Ile Asn Gly Xaa Pro Lys
1               5                   10                  15

Gly Tyr

<210> SEQ ID NO 59
<211> LENGTH: 18
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (6)..(6)
<223> OTHER INFORMATION: Xaa is D form Asp
<220> FEATURE:
<221> NAME/KEY: misc_feature
<222> LOCATION: (9)..(9)
<223> OTHER INFORMATION: Xaa is D form Asp
<220> FEATURE:
<221> NAME/KEY: misc_feature
<222> LOCATION: (14)..(14)
<223> OTHER INFORMATION: Xaa is episilon-aminocaproic acid

<400> SEQUENCE: 59

Lys Asp Pro Xaa Gly Xaa Glu Val Xaa Gly Ile Asn Gly Xaa Pro Lys
1               5                   10                  15

Gly Tyr

<210> SEQ ID NO 60
<211> LENGTH: 18
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (14)..(14)
<223> OTHER INFORMATION: Xaa is episilon-aminocaproic acid
```

```
<400> SEQUENCE: 60

Lys Asp Pro Xaa Gly Asp Glu Val Asp Gly Ile Asn Gly Xaa Pro Lys
1               5                   10                  15

Gly Tyr

<210> SEQ ID NO 61
<211> LENGTH: 18
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (14)..(14)
<223> OTHER INFORMATION: Xaa is episilon-aminocaproic acid

<400> SEQUENCE: 61

Lys Asp Asx Xaa Gly Asp Glu Val Asn Gly Ile Asn Gly Xaa Pro Lys
1               5                   10                  15

Gly Tyr

<210> SEQ ID NO 62
<211> LENGTH: 18
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 62

Lys Asp Asx Xaa Gly Asp Glu Val Asp Gly Ile Asp Gly Xaa Pro Lys
1               5                   10                  15

Gly Tyr

<210> SEQ ID NO 63
<211> LENGTH: 18
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 63

Lys Asp Asx Xaa Gly Asp Glu Val Asp Gly Ile Asn Gly Xaa Pro Lys
1               5                   10                  15

Gly Tyr

<210> SEQ ID NO 64
<211> LENGTH: 18
```

<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (14)..(14)
<223> OTHER INFORMATION: Xaa is episilon-aminocaproic acid

<400> SEQUENCE: 64

Lys Asp Asx Xaa Gly Asp Glu Val Asn Gly Ile Asp Gly Xaa Pro Lys
1               5                   10                  15

Gly Tyr

<210> SEQ ID NO 65
<211> LENGTH: 19
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid

<400> SEQUENCE: 65

Lys Asp Asx Xaa Xaa Gly Asp Glu Val Asp Gly Ile Asp Xaa Xaa Pro
1               5                   10                  15

Lys Gly Tyr

<210> SEQ ID NO 66
<211> LENGTH: 18
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (14)..(14)
<223> OTHER INFORMATION: Xaa is episilon-aminocaproic acid

<400> SEQUENCE: 66

Lys Asp Asx Xaa Gly Asn Glu Val Asp Gly Ile Asp Gly Xaa Pro Lys
1               5                   10                  15

Gly Tyr

<210> SEQ ID NO 67
<211> LENGTH: 18
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature

```
<222> LOCATION: (14)..(14)
<223> OTHER INFORMATION: Xaa is episilon-aminocaproic acid

<400> SEQUENCE: 67

Lys Asp Asx Xaa Gly Asp Glu Val Asp Gly Ile Asn Gly Xaa Pro Lys
1               5                   10                  15

Gly Tyr

<210> SEQ ID NO 68
<211> LENGTH: 18
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (14)..(14)
<223> OTHER INFORMATION: Xaa is episilon-aminocaproic acid

<400> SEQUENCE: 68

Lys Asp Asx Xaa Gly Asn Glu Val Asp Gly Ile Asn Gly Xaa Pro Lys
1               5                   10                  15

Gly Tyr

<210> SEQ ID NO 69
<211> LENGTH: 18
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (14)..(14)
<223> OTHER INFORMATION: Xaa is episilon-aminocaproic acid

<400> SEQUENCE: 69

Lys Asp Asx Xaa Gly Asp Glu Val Asn Gly Ile Asn Gly Xaa Pro Lys
1               5                   10                  15

Gly Tyr

<210> SEQ ID NO 70
<211> LENGTH: 18
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (14)..(14)
<223> OTHER INFORMATION: Xaa is episilon-aminocaproic acid

<400> SEQUENCE: 70

Lys Asp Asx Xaa Gly Asn Glu Val Asn Gly Ile Asn Gly Xaa Pro Lys
1               5                   10                  15

Gly Tyr
```

<210> SEQ ID NO 71
<211> LENGTH: 19
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 71

Lys Asp Asx Xaa Gly Xaa Asp Glu Val Asp Gly Ile Asp Gly Xaa Pro
1               5                   10                  15

Lys Gly Lys

<210> SEQ ID NO 72
<211> LENGTH: 19
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa is episilon-aminocaproic acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 72

Lys Asp Asx Xaa Gly Xaa Asp Glu Val Asp Gly Ile Asp Gly Xaa Pro
1               5                   10                  15

Lys Gly Tyr

<210> SEQ ID NO 73
<211> LENGTH: 19
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (14)..(14)
<223> OTHER INFORMATION: Xaa is episilon-aminocaproic acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 73

Lys Asp Asx Xaa Gly Trp Asp Glu Val Asp Gly Ile Asp Gly Xaa Pro
1               5                   10                  15

Lys Gly Tyr

<210> SEQ ID NO 74
<211> LENGTH: 19
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (6)..(6)
<223> OTHER INFORMATION: Xaa is D form Trp
<220> FEATURE:
<221> NAME/KEY: misc_feature
<222> LOCATION: (15)..(15)
<223> OTHER INFORMATION: Xaa is episilon-aminocaproic acid

<400> SEQUENCE: 74

Lys Asp Asx Xaa Gly Xaa Asp Glu Val Asp Gly Ile Asp Gly Xaa Pro
1               5                   10                  15

Lys Gly Tyr

<210> SEQ ID NO 75
<211> LENGTH: 20
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (6)..(7)
<223> OTHER INFORMATION: Xaa is D form tetrahydroisoquinoline-3-
    carboxylic acid
<220> FEATURE:
<221> NAME/KEY: misc_feature
<222> LOCATION: (16)..(16)
<223> OTHER INFORMATION: Xaa is episilon-aminocaproic acid

<400> SEQUENCE: 75

Lys Asp Asx Xaa Gly Xaa Xaa Asp Glu Val Asp Gly Ile Asp Gly Xaa
1               5                   10                  15

Pro Lys Gly Tyr
            20

<210> SEQ ID NO 76
<211> LENGTH: 20
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (6)..(7)
<223> OTHER INFORMATION: Xaa is D form Trp
<220> FEATURE:
<221> NAME/KEY: misc_feature

```
<222> LOCATION: (16)..(16)
<223> OTHER INFORMATION: Xaa is episilon-aminocaproic acid

<400> SEQUENCE: 76

Lys Asp Asx Xaa Gly Xaa Xaa Asp Glu Val Asp Gly Ile Asp Gly Xaa
1               5                   10                  15

Pro Lys Gly Tyr
            20

<210> SEQ ID NO 77
<211> LENGTH: 14
<212> TYPE: PRT
<213> ORGANISM: Artificial
<220> FEATURE:
<223> OTHER INFORMATION: Synthetic peptide.

<400> SEQUENCE: 77

Lys Asp Asx Tyr Val Ala Asp Gly Ile Asp Pro Lys Gly Tyr
1               5                   10

<210> SEQ ID NO 78
<211> LENGTH: 14
<212> TYPE: PRT
<213> ORGANISM: Artificial
<220> FEATURE:
<223> OTHER INFORMATION: Synthetic peptide.

<400> SEQUENCE: 78

Lys Asp Asx Tyr Val Ala Asp Gly Ile Asn Pro Lys Gly Tyr
1               5                   10

<210> SEQ ID NO 79
<211> LENGTH: 14
<212> TYPE: PRT
<213> ORGANISM: Artificial
<220> FEATURE:
<223> OTHER INFORMATION: Synthetic peptide.

<400> SEQUENCE: 79

Lys Asp Asx Tyr Val Ala Asn Gly Ile Asn Pro Lys Gly Tyr
1               5                   10

<210> SEQ ID NO 80
<211> LENGTH: 16
<212> TYPE: PRT
<213> ORGANISM: Artificial
<220> FEATURE:
<223> OTHER INFORMATION: Synthetic peptide.

<400> SEQUENCE: 80

Lys Asp Asx Gly Tyr Val Ala Asp Gly Ile Asp Gly Pro Lys Gly Tyr
1               5                   10                  15

<210> SEQ ID NO 81
<211> LENGTH: 16
<212> TYPE: PRT
<213> ORGANISM: Artificial
<220> FEATURE:
<223> OTHER INFORMATION: Synthetic peptide.

<400> SEQUENCE: 81

Lys Asp Asx Gly Tyr Val Ala Asp Gly Ile Asn Gly Pro Lys Gly Tyr
1               5                   10                  15

<210> SEQ ID NO 82
<211> LENGTH: 16
```

```
<212> TYPE: PRT
<213> ORGANISM: Artificial
<220> FEATURE:
<223> OTHER INFORMATION: Synthetic peptide.

<400> SEQUENCE: 82

Lys Asp Asx Gly Tyr Val Ala Asn Gly Ile Asn Gly Pro Lys Gly Tyr
1               5                   10                  15

<210> SEQ ID NO 83
<211> LENGTH: 18
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(14)
<223> OTHER INFORMATION: Xaa is episilon-aminocaproic acid
<220> FEATURE:
<221> NAME/KEY: misc_feature
<222> LOCATION: (14)..(14)
<223> OTHER INFORMATION: Xaa is episilon-aminocaproic acid

<400> SEQUENCE: 83

Lys Asp Asx Xaa Gly Tyr Val Ala Asp Gly Ile Asp Gly Xaa Pro Lys
1               5                   10                  15

Gly Tyr

<210> SEQ ID NO 84
<211> LENGTH: 18
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (14)..(14)
<223> OTHER INFORMATION: Xaa is episilon-aminocaproic acid

<400> SEQUENCE: 84

Lys Asp Asx Xaa Gly Tyr Val Ala Asn Gly Ile Asp Gly Xaa Pro Lys
1               5                   10                  15

Gly Tyr

<210> SEQ ID NO 85
<211> LENGTH: 18
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (14)..(14)
<223> OTHER INFORMATION: Xaa is episilon-aminocaproic acid

<400> SEQUENCE: 85

Lys Asp Asx Xaa Gly Tyr Val Ala Asn Gly Ile Asn Gly Xaa Pro Lys
1               5                   10                  15

Gly Tyr
```

```
<210> SEQ ID NO 86
<211> LENGTH: 18
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (14)..(14)
<223> OTHER INFORMATION: Xaa is episilon-aminocaproic acid

<400> SEQUENCE: 86

Lys Asp Asx Xaa Gly Tyr Val Ala Asp Gly Ile Asn Gly Xaa Pro Lys
1               5                   10                  15

Gly Tyr

<210> SEQ ID NO 87
<211> LENGTH: 18
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (6)..(6)
<223> OTHER INFORMATION: Xaa is D form Tyr
<220> FEATURE:
<221> NAME/KEY: misc_feature
<222> LOCATION: (14)..(14)
<223> OTHER INFORMATION: Xaa is episilon-aminocaproic acid

<400> SEQUENCE: 87

Lys Asp Asx Xaa Gly Xaa Val Ala Asp Gly Ile Asn Gly Xaa Pro Lys
1               5                   10                  15

Gly Tyr

<210> SEQ ID NO 88
<211> LENGTH: 14
<212> TYPE: PRT
<213> ORGANISM: Artificial
<220> FEATURE:
<223> OTHER INFORMATION: Synthetic peptide.

<400> SEQUENCE: 88

Lys Asp Asx Tyr Val His Asp Ala Pro Val Pro Lys Gly Tyr
1               5                   10

<210> SEQ ID NO 89
<211> LENGTH: 14
<212> TYPE: PRT
<213> ORGANISM: Artificial
<220> FEATURE:
<223> OTHER INFORMATION: Synthetic peptide.

<400> SEQUENCE: 89

Lys Asp Asx Tyr Val His Asp Ala Pro Val Pro Lys Gly Tyr
1               5                   10

<210> SEQ ID NO 90
<211> LENGTH: 14
```

```
<212> TYPE: PRT
<213> ORGANISM: Artificial
<220> FEATURE:
<223> OTHER INFORMATION: Synthetic peptide.

<400> SEQUENCE: 90

Lys Asp Asx Tyr Val His Asp Ala Pro Val Pro Lys Gly Tyr
1               5                   10

<210> SEQ ID NO 91
<211> LENGTH: 16
<212> TYPE: PRT
<213> ORGANISM: Artificial
<220> FEATURE:
<223> OTHER INFORMATION: Synthetic peptide.

<400> SEQUENCE: 91

Lys Asp Asx Gly Tyr Val His Asp Ala Pro Val Gly Pro Lys Gly Tyr
1               5                   10                  15

<210> SEQ ID NO 92
<211> LENGTH: 16
<212> TYPE: PRT
<213> ORGANISM: Artificial
<220> FEATURE:
<223> OTHER INFORMATION: Synthetic peptide.

<400> SEQUENCE: 92

Lys Asp Asx Gly Tyr Val His Asp Ala Pro Val Gly Pro Lys Gly Tyr
1               5                   10                  15

<210> SEQ ID NO 93
<211> LENGTH: 16
<212> TYPE: PRT
<213> ORGANISM: Artificial
<220> FEATURE:
<223> OTHER INFORMATION: Synthetic peptide.

<400> SEQUENCE: 93

Lys Asp Asx Gly Tyr Val His Asp Ala Pro Val Gly Pro Lys Gly Tyr
1               5                   10                  15

<210> SEQ ID NO 94
<211> LENGTH: 18
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (14)..(14)
<223> OTHER INFORMATION: Xaa is episilon-aminocaproic acid

<400> SEQUENCE: 94

Lys Asp Asx Xaa Gly Tyr Val His Asp Ala Pro Val Gly Xaa Pro Lys
1               5                   10                  15

Gly Tyr

<210> SEQ ID NO 95
<211> LENGTH: 18
<212> TYPE: PRT
<213> ORGANISM: Artificial
<220> FEATURE:
<223> OTHER INFORMATION: Synthetic peptide.
```

```
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (14)..(14)
<223> OTHER INFORMATION: Xaa is episilon-aminocaproic acid

<400> SEQUENCE: 95

Lys Asp Asx Xaa Gly Tyr Val His Asp Ala Pro Val Gly Xaa Pro Lys
1               5                   10                  15

Gly Tyr

<210> SEQ ID NO 96
<211> LENGTH: 18
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (14)..(14)
<223> OTHER INFORMATION: Xaa is episilon-aminocaproic acid

<400> SEQUENCE: 96

Lys Asp Asx Xaa Gly Tyr Val His Asp Ala Pro Val Gly Xaa Pro Lys
1               5                   10                  15

Gly Tyr

<210> SEQ ID NO 97
<211> LENGTH: 18
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (14)..(14)
<223> OTHER INFORMATION: Xaa is episilon-aminocaproic acid

<400> SEQUENCE: 97

Lys Asp Asx Xaa Gly Tyr Val His Asp Ala Pro Val Gly Xaa Pro Lys
1               5                   10                  15

Gly Tyr

<210> SEQ ID NO 98
<211> LENGTH: 18
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (14)..(14)
<223> OTHER INFORMATION: Xaa is episilon-aminocaproic acid

<400> SEQUENCE: 98
```

-continued

Lys Asp Asx Xaa Gly Tyr Val His Asp Ala Pro Val Gly Xaa Pro Lys
1               5                   10                  15

Gly Tyr

<210> SEQ ID NO 99
<211> LENGTH: 18
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (6)..(6)
<223> OTHER INFORMATION: Xaa is D form Tyr
<220> FEATURE:
<221> NAME/KEY: misc_feature
<222> LOCATION: (14)..(14)
<223> OTHER INFORMATION: Xaa is episilon-aminocaproic acid

<400> SEQUENCE: 99

Lys Asp Asx Xaa Gly Xaa Val His Asp Ala Pro Val Gly Xaa Pro Lys
1               5                   10                  15

Gly Tyr

<210> SEQ ID NO 100
<211> LENGTH: 17
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (13)..(13)
<223> OTHER INFORMATION: Xaa is episilon-aminocaproic acid

<400> SEQUENCE: 100

Lys Asp Pro Xaa Gly Leu Val Glu Ile Asp Asn Gly Xaa Pro Lys Gly
1               5                   10                  15

Tyr

<210> SEQ ID NO 101
<211> LENGTH: 17
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (13)..(13)
<223> OTHER INFORMATION: Xaa is episilon-aminocaproic acid

<400> SEQUENCE: 101

Lys Asp Pro Xaa Gly Leu Val Glu Ile Glu Asn Gly Xaa Pro Lys Gly
1               5                   10                  15

Tyr

<210> SEQ ID NO 102
<211> LENGTH: 14
<212> TYPE: PRT
<213> ORGANISM: Artificial
<220> FEATURE:
<223> OTHER INFORMATION: Synthetic peptide.

<400> SEQUENCE: 102

Lys Asp Asx Leu Val Glu Ile Asp Asn Gly Pro Lys Gly Tyr
1               5                   10

<210> SEQ ID NO 103
<211> LENGTH: 16
<212> TYPE: PRT
<213> ORGANISM: Artificial
<220> FEATURE:
<223> OTHER INFORMATION: Synthetic peptide.

<400> SEQUENCE: 103

Lys Asp Asx Gly Leu Val Glu Ile Asp Asn Gly Gly Pro Lys Gly Tyr
1               5                   10                  15

<210> SEQ ID NO 104
<211> LENGTH: 18
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (14)..(14)
<223> OTHER INFORMATION: Xaa is episilon-aminocaproic acid

<400> SEQUENCE: 104

Lys Asp Asx Xaa Gly Leu Val Glu Ile Asp Asn Gly Gly Xaa Pro Lys
1               5                   10                  15

Gly Tyr

<210> SEQ ID NO 105
<211> LENGTH: 18
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 105

Lys Asp Asx Xaa Gly Leu Val Glu Ile Asn Asn Gly Gly Xaa Pro Lys
1               5                   10                  15

Gly Tyr

<210> SEQ ID NO 106
<211> LENGTH: 18
<212> TYPE: PRT
<213> ORGANISM: Artificial
<220> FEATURE:
<223> OTHER INFORMATION: Synthetic peptide.

```
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (14)..(14)
<223> OTHER INFORMATION: Xaa is episilon-aminocaproic acid

<400> SEQUENCE: 106

Lys Asp Pro Xaa Gly Ile Glu Thr Glu Ser Gly Val Gly Xaa Pro Lys
1               5                   10                  15

Gly Tyr

<210> SEQ ID NO 107
<211> LENGTH: 16
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (12)..(12)
<223> OTHER INFORMATION: Xaa is episilon-aminocaproic acid

<400> SEQUENCE: 107

Lys Asp Pro Xaa Gly Ile Glu Thr Asp Ser Gly Xaa Pro Lys Gly Tyr
1               5                   10                  15

<210> SEQ ID NO 108
<211> LENGTH: 16
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (12)..(12)
<223> OTHER INFORMATION: Xaa is episilon-aminocaproic acid

<400> SEQUENCE: 108

Lys Asp Pro Xaa Gly Ile Glu Thr Glu Ser Gly Xaa Pro Lys Gly Tyr
1               5                   10                  15

<210> SEQ ID NO 109
<211> LENGTH: 17
<212> TYPE: PRT
<213> ORGANISM: Artificial
<220> FEATURE:
<223> OTHER INFORMATION: Synthetic peptide.

<400> SEQUENCE: 109

Lys Asp Asx Gly Ile Glu Thr Asp Ser Gly Val Asp Asp Pro Lys Gly
1               5                   10                  15

Tyr

<210> SEQ ID NO 110
<211> LENGTH: 17
<212> TYPE: PRT
<213> ORGANISM: Artificial
<220> FEATURE:
```

<223> OTHER INFORMATION: Synthetic peptide.

<400> SEQUENCE: 110

Lys Asp Asx Gly Ile Glu Thr Asn Ser Gly Val Asp Asp Pro Lys Gly
1               5                   10                  15

Tyr

<210> SEQ ID NO 111
<211> LENGTH: 19
<212> TYPE: PRT
<213> ORGANISM: Artificial
<220> FEATURE:
<223> OTHER INFORMATION: Synthetic peptide.

<400> SEQUENCE: 111

Lys Asp Asx Gly Gly Ile Glu Thr Asp Ser Gly Val Asp Asp Gly Pro
1               5                   10                  15

Lys Gly Tyr

<210> SEQ ID NO 112
<211> LENGTH: 17
<212> TYPE: PRT
<213> ORGANISM: Artificial
<220> FEATURE:
<223> OTHER INFORMATION: Synthetic peptide.

<400> SEQUENCE: 112

Lys Asp Asx Gly Gly Ile Glu Thr Asn Ser Gly Val Gly Pro Lys Gly
1               5                   10                  15

Tyr

<210> SEQ ID NO 113
<211> LENGTH: 17
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (13)..(13)
<223> OTHER INFORMATION: Xaa is episilon-aminocaproic acid

<400> SEQUENCE: 113

Lys Asp Asx Xaa Gly Ile Glu Thr Asp Ser Gly Val Xaa Pro Lys Gly
1               5                   10                  15

Tyr

<210> SEQ ID NO 114
<211> LENGTH: 17
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (13)..(13)
<223> OTHER INFORMATION: Xaa is episilon-aminocaproic acid

<400> SEQUENCE: 114

Lys Asp Asx Xaa Gly Ile Glu Thr Asn Ser Gly Val Xaa Pro Lys Gly
1               5                   10                  15

Tyr

<210> SEQ ID NO 115
<211> LENGTH: 19
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 115

Lys Asp Asx Xaa Gly Gly Ile Glu Thr Asp Ser Gly Val Gly Xaa Pro
1               5                   10                  15

Lys Gly Tyr

<210> SEQ ID NO 116
<211> LENGTH: 19
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (15)..(15)
<223> OTHER INFORMATION: Xaa is episilon-aminocaproic acid

<400> SEQUENCE: 116

Lys Asp Asx Xaa Gly Gly Ile Glu Thr Asn Ser Gly Val Gly Xaa Pro
1               5                   10                  15

Lys Gly Tyr

<210> SEQ ID NO 117
<211> LENGTH: 19
<212> TYPE: PRT
<213> ORGANISM: Artificial
<220> FEATURE:
<223> OTHER INFORMATION: Synthetic peptide.

<400> SEQUENCE: 117

Lys Asp Asx Gly Ser Glu Ser Met Asp Ser Gly Ile Ser Leu Asp Pro
1               5                   10                  15

Lys Gly Tyr

<210> SEQ ID NO 118
<211> LENGTH: 17
<212> TYPE: PRT
<213> ORGANISM: Artificial
<220> FEATURE:
<223> OTHER INFORMATION: Synthetic peptide.

<400> SEQUENCE: 118

Lys Asp Asx Gly Gly Ser Glu Ser Met Asp Ser Gly Gly Pro Lys Gly
1               5                   10                  15

Tyr

<210> SEQ ID NO 119
<211> LENGTH: 19
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (15)..(15)
<223> OTHER INFORMATION: Xaa is episilon-aminocaproic acid

<400> SEQUENCE: 119

Lys Asp Asx Xaa Gly Gly Ser Glu Ser Met Asp Ser Gly Gly Xaa Pro
1               5                   10                  15

Lys Gly Tyr

<210> SEQ ID NO 120
<211> LENGTH: 19
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (15)..(15)
<223> OTHER INFORMATION: Xaa is episilon-aminocaproic acid

<400> SEQUENCE: 120

Lys Asp Asx Xaa Gly Asp Val Val Cys Cys Ser Met Ser Gly Xaa Pro
1               5                   10                  15

Lys Gly Tyr

<210> SEQ ID NO 121
<211> LENGTH: 19
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (15)..(15)
<223> OTHER INFORMATION: Xaa is episilon-aminocaproic acid

<400> SEQUENCE: 121

Lys Asp Asx Xaa Gly Asp Val Val Cys Asp Ser Met Ser Gly Xaa Pro
1               5                   10                  15

Lys Gly Tyr

<210> SEQ ID NO 122
<211> LENGTH: 20
<212> TYPE: PRT
<213> ORGANISM: Artificial
<220> FEATURE:
<223> OTHER INFORMATION: Synthetic peptide.

```
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (16)..(16)
<223> OTHER INFORMATION: Xaa is episilon-aminocaproic acid

<400> SEQUENCE: 122

Lys Asp Asx Xaa Gly Asp Val Val Cys Cys Ser Asp Met Ser Gly Xaa
1               5                   10                  15

Pro Lys Gly Tyr
            20

<210> SEQ ID NO 123
<211> LENGTH: 20
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (16)..(16)
<223> OTHER INFORMATION: Xaa is episilon-aminocaproic acid

<400> SEQUENCE: 123

Lys Asp Asx Xaa Gly Asp Val Val Cys Asp Ser Asp Met Ser Gly Xaa
1               5                   10                  15

Pro Lys Gly Tyr
            20

<210> SEQ ID NO 124
<211> LENGTH: 20
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (16)..(16)
<223> OTHER INFORMATION: Xaa is episilon-aminocaproic acid

<400> SEQUENCE: 124

Lys Asp Asx Xaa Gly Asp Val Val Cys Cys Pro Asp Met Ser Gly Xaa
1               5                   10                  15

Pro Lys Gly Tyr
            20

<210> SEQ ID NO 125
<211> LENGTH: 18
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (14)..(14)
```

<223> OTHER INFORMATION: Xaa is episilon-aminocaproic acid

<400> SEQUENCE: 125

Lys Asp Asx Xaa Gly Glu Asp Val Val Cys Cys Ser Gly Xaa Pro Lys
1               5                   10                  15

Gly Tyr

<210> SEQ ID NO 126
<211> LENGTH: 18
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (14)..(14)
<223> OTHER INFORMATION: Xaa is episilon-aminocaproic acid

<400> SEQUENCE: 126

Lys Asp Asx Xaa Gly Glu Asp Val Val Cys Asp Ser Gly Xaa Pro Lys
1               5                   10                  15

Gly Tyr

<210> SEQ ID NO 127
<211> LENGTH: 19
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (15)..(15)
<223> OTHER INFORMATION: Xaa is episilon-aminocaproic acid

<400> SEQUENCE: 127

Lys Asp Asx Xaa Gly Glu Asp Asp Val Val Cys Cys Pro Gly Xaa Pro
1               5                   10                  15

Lys Gly Tyr

<210> SEQ ID NO 128
<211> LENGTH: 19
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (15)..(15)
<223> OTHER INFORMATION: Xaa is episilon-aminocaproic acid

<400> SEQUENCE: 128

Lys Asp Asx Xaa Gly Glu Asp Asp Val Val Cys Asp Pro Gly Xaa Pro
1               5                   10                  15

Lys Gly Tyr

```
<210> SEQ ID NO 129
<211> LENGTH: 21
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 129

Lys Asp Asx Xaa Gly Asp Asp Val Val Cys Cys Ser Asp Met Ser Gly
1               5                   10                  15

Xaa Pro Lys Gly Tyr
            20

<210> SEQ ID NO 130
<211> LENGTH: 20
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (13)..(13)
<223> OTHER INFORMATION: Xaa is D form Met
<220> FEATURE:
<221> NAME/KEY: misc_feature
<222> LOCATION: (16)..(16)
<223> OTHER INFORMATION: Xaa is episilon-aminocaproic acid

<400> SEQUENCE: 130

Lys Asp Asx Xaa Gly Asp Val Asp Val Cys Asp Ser Xaa Ser Gly Xaa
1               5                   10                  15

Pro Lys Gly Tyr
            20

<210> SEQ ID NO 131
<211> LENGTH: 20
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (13)..(13)
<223> OTHER INFORMATION: Xaa is D form Met
<220> FEATURE:
<221> NAME/KEY: misc_feature
<222> LOCATION: (16)..(16)
<223> OTHER INFORMATION: Xaa is episilon-aminocaproic acid

<400> SEQUENCE: 131

Lys Asp Asx Xaa Gly Asp Val Val Cys Cys Pro Xaa Ser Gly Xaa
1               5                   10                  15

Pro Lys Gly Tyr
            20
```

```
<210> SEQ ID NO 132
<211> LENGTH: 18
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (14)..(14)
<223> OTHER INFORMATION: Xaa is episilon-aminocaproic acid

<400> SEQUENCE: 132

Lys Asp Asx Xaa Gly Asp Val Val Cys Cys Ser Met Gly Xaa Pro Lys
1               5                   10                  15

Gly Tyr

<210> SEQ ID NO 133
<211> LENGTH: 18
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (14)..(14)
<223> OTHER INFORMATION: Xaa is episilon-aminocaproic acid

<400> SEQUENCE: 133

Lys Asp Asx Xaa Gly Asp Val Val Cys Asp Ser Met Gly Xaa Pro Lys
1               5                   10                  15

Gly Tyr

<210> SEQ ID NO 134
<211> LENGTH: 16
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (12)..(12)
<223> OTHER INFORMATION: Xaa is episilon-aminocaproic acid

<400> SEQUENCE: 134

Lys Asp Asx Xaa Gly Val Cys Cys Ser Met Gly Xaa Pro Lys Gly Tyr
1               5                   10                  15

<210> SEQ ID NO 135
<211> LENGTH: 16
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
```

```
<221> NAME/KEY: misc_feature
<222> LOCATION: (12)..(12)
<223> OTHER INFORMATION: Xaa is episilon-aminocaproic acid

<400> SEQUENCE: 135

Lys Asp Asx Xaa Gly Val Cys Asp Ser Met Gly Xaa Pro Lys Gly Tyr
1               5                   10                  15

<210> SEQ ID NO 136
<211> LENGTH: 19
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa can be any naturally occurring amino acid

<400> SEQUENCE: 136

Lys Asp Asx Xaa Gly Asp Glu Met Glu Glu Cys Ser Gln His Leu Pro
1               5                   10                  15

Lys Gly Tyr

<210> SEQ ID NO 137
<211> LENGTH: 19
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid

<400> SEQUENCE: 137

Lys Asp Asx Xaa Gly Asp Glu Met Glu Glu Cys Pro Gln His Leu Pro
1               5                   10                  15

Lys Gly Tyr

<210> SEQ ID NO 138
<211> LENGTH: 19
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid

<400> SEQUENCE: 138

Lys Asp Asx Xaa Gly Asp Glu Met Glu Glu Asp Ser Gln His Leu Pro
1               5                   10                  15

Lys Gly Tyr

<210> SEQ ID NO 139
<211> LENGTH: 18
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid

<400> SEQUENCE: 139
```

-continued

Lys Asp Asx Xaa Gly Glu Met Glu Glu Cys Ser Gln His Leu Pro Lys
1               5                   10                  15

Gly Tyr

<210> SEQ ID NO 140
<211> LENGTH: 18
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid

<400> SEQUENCE: 140

Lys Asp Asx Xaa Gly Glu Met Glu Glu Cys Pro Gln His Leu Pro Lys
1               5                   10                  15

Gly Tyr

<210> SEQ ID NO 141
<211> LENGTH: 18
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid

<400> SEQUENCE: 141

Lys Asp Asx Xaa Gly Glu Met Glu Glu Asp Ser Gln His Leu Pro Lys
1               5                   10                  15

Gly Tyr

<210> SEQ ID NO 142
<211> LENGTH: 19
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid

<400> SEQUENCE: 142

Lys Asp Asx Xaa Gly Glu Met Glu Glu Cys Ser Gln His Leu Gly Pro
1               5                   10                  15

Lys Gly Tyr

<210> SEQ ID NO 143
<211> LENGTH: 19
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid

<400> SEQUENCE: 143

Lys Asp Asx Xaa Gly Glu Met Glu Glu Cys Pro Gln His Leu Gly Pro
1               5                   10                  15

Lys Gly Tyr

<210> SEQ ID NO 144
<211> LENGTH: 19
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid

<400> SEQUENCE: 144

Lys Asp Asx Xaa Gly Glu Met Glu Glu Asp Ser Gln His Leu Gly Pro
1               5                   10                  15

Lys Gly Tyr

<210> SEQ ID NO 145
<211> LENGTH: 20
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid

<400> SEQUENCE: 145

Lys Asp Asx Xaa Gly Glu Met Glu Glu Cys Ser Gln His Leu Gly Xaa
1               5                   10                  15

Pro Lys Gly Tyr
            20

<210> SEQ ID NO 146
<211> LENGTH: 20
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (16)..(16)
<223> OTHER INFORMATION: Xaa is episilon-aminocaproic acid

<400> SEQUENCE: 146

Lys Asp Asx Xaa Gly Glu Met Glu Glu Cys Pro Gln His Leu Gly Xaa
1               5                   10                  15

Pro Lys Gly Tyr
            20

<210> SEQ ID NO 147
<211> LENGTH: 20
<212> TYPE: PRT
<213> ORGANISM: Artificial
<220> FEATURE:
<223> OTHER INFORMATION: Synthetic peptide.
<220> FEATURE:
<221> NAME/KEY: misc_feature

```
<222> LOCATION: (4)..(4)
<223> OTHER INFORMATION: Xaa is episilon-aminocaproic acid
<220> FEATURE:
<221> NAME/KEY: misc_feature
<222> LOCATION: (16)..(16)
<223> OTHER INFORMATION: Xaa is episilon-aminocaproic acid

<400> SEQUENCE: 147

Lys Asp Asx Xaa Gly Glu Met Glu Glu Asp Ser Gln His Leu Gly Xaa
 1               5                  10                  15

Pro Lys Gly Tyr
            20

<210> SEQ ID NO 148
<211> LENGTH: 17
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (13)..(13)
<223> OTHER INFORMATION: Xaa is episilon-aminocaproic acid

<400> SEQUENCE: 148

Lys Asp Asx Xaa Gly Val Met Thr Gly Arg Thr Gly Xaa Pro Lys Gly
 1               5                  10                  15

Tyr

<210> SEQ ID NO 149
<211> LENGTH: 17
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 149

Lys Asp Asx Xaa Gly Val Xaa Thr Gly Arg Thr Gly Xaa Pro Lys Gly
 1               5                  10                  15

Tyr

<210> SEQ ID NO 150
<211> LENGTH: 17
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (13)..(13)
```

```
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa is episilon-aminocaproic acid

<400> SEQUENCE: 150

Lys Asp Asx Xaa Gly Val Met Thr Gly Arg Thr Gly Xaa Pro Lys Gly
1               5                   10                  15
Tyr

<210> SEQ ID NO 151
<211> LENGTH: 17
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (13)..(13)
<223> OTHER INFORMATION: Xaa is episilon-aminocaproic acid

<400> SEQUENCE: 151

Lys Asp Asx Xaa Gly Val Met Thr Gly Arg Thr Gly Xaa Pro Lys Gly
1               5                   10                  15
Tyr

<210> SEQ ID NO 152
<211> LENGTH: 16
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (12)..(12)
<223> OTHER INFORMATION: Xaa is episilon-aminocaproic acid

<400> SEQUENCE: 152

Lys Asp Asx Xaa Gly Val Met Thr Gly Arg Gly Xaa Pro Lys Gly Tyr
1               5                   10                  15

<210> SEQ ID NO 153
<211> LENGTH: 17
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (13)..(13)
<223> OTHER INFORMATION: Xaa is episilon-aminocaproic acid

<400> SEQUENCE: 153

Lys Asp Asx Xaa Gly Val Met Thr Gly Arg Gly Gly Xaa Pro Lys Gly
1               5                   10                  15
Tyr
```

-continued

```
<210> SEQ ID NO 154
<211> LENGTH: 17
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (7)..(7)
<223> OTHER INFORMATION: Xaa is D form Met
<220> FEATURE:
<221> NAME/KEY: misc_feature
<222> LOCATION: (13)..(13)
<223> OTHER INFORMATION: Xaa is episilon-aminocaproic acid

<400> SEQUENCE: 154

Lys Asp Asx Xaa Gly Val Xaa Thr Gly Arg Gly Gly Xaa Pro Lys Gly
 1               5                  10                  15

Tyr

<210> SEQ ID NO 155
<211> LENGTH: 8
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid

<400> SEQUENCE: 155

Lys Asp Pro Xaa Thr Gly Arg Thr
 1               5

<210> SEQ ID NO 156
<211> LENGTH: 11
<212> TYPE: PRT
<213> ORGANISM: Artificial
<220> FEATURE:
<223> OTHER INFORMATION: Synthetic peptide.

<400> SEQUENCE: 156

Asp Pro Thr Gly Arg Thr Gly Pro Lys Gly Tyr
 1               5                  10

<210> SEQ ID NO 157
<211> LENGTH: 15
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (11)..(11)
<223> OTHER INFORMATION: Xaa is episilon-aminocaproic acid

<400> SEQUENCE: 157

Lys Asp Pro Val Met Thr Gly Arg Thr Gly Xaa Pro Lys Gly Tyr
 1               5                  10                  15

<210> SEQ ID NO 158
<211> LENGTH: 13
<212> TYPE: PRT
```

```
<213> ORGANISM: Artificial
<220> FEATURE:
<223> OTHER INFORMATION: Synthetic peptide.
<220> FEATURE:
<221> NAME/KEY: misc_feature
<222> LOCATION: (9)..(9)
<223> OTHER INFORMATION: Xaa is episilon-aminocaproic acid

<400> SEQUENCE: 158

Lys Asp Pro Thr Gly Arg Thr Gly Xaa Pro Lys Gly Tyr
1               5                   10

<210> SEQ ID NO 159
<211> LENGTH: 15
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (11)..(11)
<223> OTHER INFORMATION: Xaa is episilon-aminocaproic acid

<400> SEQUENCE: 159

Lys Asp Pro Xaa Gly Thr Gly Arg Thr Gly Xaa Pro Lys Gly Tyr
1               5                   10                  15

<210> SEQ ID NO 160
<211> LENGTH: 14
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid

<400> SEQUENCE: 160

Lys Asp Pro Xaa Gly Thr Gly Arg Thr Gly Pro Lys Gly Tyr
1               5                   10

<210> SEQ ID NO 161
<211> LENGTH: 13
<212> TYPE: PRT
<213> ORGANISM: Artificial
<220> FEATURE:
<223> OTHER INFORMATION: Synthetic peptide.

<400> SEQUENCE: 161

Lys Asp Pro Gly Thr Gly Arg Thr Gly Pro Lys Gly Tyr
1               5                   10

<210> SEQ ID NO 162
<211> LENGTH: 14
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (0)..(10)
<223> OTHER INFORMATION: Xaa is episilon-aminocaproic acid
<220> FEATURE:
<221> NAME/KEY: misc_feature
<222> LOCATION: (4)..(4)
<223> OTHER INFORMATION: Xaa is episilon-aminocaproic acid
```

```
<400> SEQUENCE: 162

Lys Asp Pro Xaa Thr Gly Arg Thr Gly Xaa Pro Lys Gly Tyr
1               5                   10

<210> SEQ ID NO 163
<211> LENGTH: 13
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is 4-aminobutyric acid

<400> SEQUENCE: 163

Lys Asp Pro Xaa Thr Gly Arg Thr Gly Pro Lys Gly Tyr
1               5                   10

<210> SEQ ID NO 164
<211> LENGTH: 13
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is 8-aminocaprylic acid

<400> SEQUENCE: 164

Lys Asp Pro Xaa Thr Gly Arg Thr Gly Pro Lys Gly Tyr
1               5                   10

<210> SEQ ID NO 165
<211> LENGTH: 17
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is 8-aminocaprylic acid
<220> FEATURE:
<221> NAME/KEY: misc_feature
<222> LOCATION: (13)..(13)
<223> OTHER INFORMATION: Xaa is 8-aminocaprylic acid

<400> SEQUENCE: 165

Lys Asp Asx Xaa Gly Val Met Thr Gly Arg Val Gly Xaa Pro Lys Gly
1               5                   10                  15

Tyr

<210> SEQ ID NO 166
<211> LENGTH: 17
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (7)..(7)
<223> OTHER INFORMATION: Xaa can be any naturally occurring amino acid
<220> FEATURE:
```

-continued

```
<221> NAME/KEY: misc_feature
<222> LOCATION: (13)..(13)
<223> OTHER INFORMATION: Xaa is episilon-aminocaproic acid

<400> SEQUENCE: 166

Lys Asp Asx Xaa Gly Val Xaa Thr Gly Arg Val Gly Xaa Pro Lys Gly
1               5                   10                  15

Tyr

<210> SEQ ID NO 167
<211> LENGTH: 17
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (13)..(13)
<223> OTHER INFORMATION: Xaa is episilon-aminocaproic acid

<400> SEQUENCE: 167

Lys Asp Asx Xaa Gly Val Met Thr Gly Arg Ala Gly Xaa Pro Lys Gly
1               5                   10                  15

Tyr

<210> SEQ ID NO 168
<211> LENGTH: 17
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa is episilon-aminocaproic acid

<400> SEQUENCE: 168

Lys Asp Asx Xaa Gly Val Xaa Thr Gly Arg Ala Gly Xaa Pro Lys Gly
1               5                   10                  15

Tyr

<210> SEQ ID NO 169
<211> LENGTH: 26
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (22)..(22)
```

```
<223> OTHER INFORMATION: Xaa is episilon-aminocaproic acid

<400> SEQUENCE: 169

Lys Asp Pro Xaa Gly Ser Glu Val Lys Leu Asp Ala Glu Phe Gly Xaa
1               5                   10                  15
Pro Lys Gly Tyr Gly Xaa Pro Lys Gly Tyr
            20                  25

<210> SEQ ID NO 170
<211> LENGTH: 20
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (7)..(7)
<223> OTHER INFORMATION: Xaa is D form Glu
<220> FEATURE:
<221> NAME/KEY: misc_feature
<222> LOCATION: (10)..(10)
<223> OTHER INFORMATION: Xaa is D form Leu
<220> FEATURE:
<221> NAME/KEY: misc_feature
<222> LOCATION: (14)..(14)
<223> OTHER INFORMATION: Xaa is D form Phe
<220> FEATURE:
<221> NAME/KEY: misc_feature
<222> LOCATION: (16)..(16)
<223> OTHER INFORMATION: Xaa is episilon-aminocaproic acid

<400> SEQUENCE: 170

Lys Asp Pro Xaa Gly Ser Xaa Val Lys Xaa Asp Ala Glu Xaa Gly Xaa
1               5                   10                  15
Pro Lys Gly Tyr
            20

<210> SEQ ID NO 171
<211> LENGTH: 20
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (7)..(7)
<223> OTHER INFORMATION: Xaa is D form Glu
<220> FEATURE:
<221> NAME/KEY: misc_feature
<222> LOCATION: (10)..(10)
<223> OTHER INFORMATION: Xaa is D form Leu
<220> FEATURE:
<221> NAME/KEY: misc_feature
<222> LOCATION: (14)..(14)
<223> OTHER INFORMATION: Xaa is D form Phe
<220> FEATURE:
<221> NAME/KEY: misc_feature
<222> LOCATION: (16)..(16)
<223> OTHER INFORMATION: Xaa is episilon-aminocaproic acid

<400> SEQUENCE: 171

Lys Asp Pro Xaa Gly Ser Xaa Val Lys Xaa Asp Ala Glu Xaa Gly Xaa
1               5                   10                  15
```

```
Pro Lys Gly Tyr
            20

<210> SEQ ID NO 172
<211> LENGTH: 21
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (16)..(16)
<223> OTHER INFORMATION: Xaa is episilon-aminocaproic acid

<400> SEQUENCE: 172

Lys Asp Asx Xaa Gly Ser Glu Val Asn Leu Asp Ala Glu Phe Gly Xaa
1               5                   10                  15

Pro Lys Asp Asp Tyr
            20

<210> SEQ ID NO 173
<211> LENGTH: 21
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (16)..(16)
<223> OTHER INFORMATION: Xaa is episilon-aminocaproic acid

<400> SEQUENCE: 173

Lys Asp Asx Xaa Gly Ser Glu Val Asn Leu Asp Ala Glu Phe Gly Xaa
1               5                   10                  15

Pro Lys Asp Asp Tyr
            20

<210> SEQ ID NO 174
<211> LENGTH: 21
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (16)..(16)
<223> OTHER INFORMATION: Xaa is episilon-aminocaproic acid

<400> SEQUENCE: 174

Lys Asp Asx Xaa Gly Ser Glu Val Lys Leu Asp Ala Glu Phe Gly Xaa
1               5                   10                  15

Pro Lys Asp Asp Tyr
            20

<210> SEQ ID NO 175
<211> LENGTH: 21
<212> TYPE: PRT
```

```
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (16)..(16)
<223> OTHER INFORMATION: Xaa is episilon-aminocaproic acid

<400> SEQUENCE: 175

Lys Asp Asx Xaa Gly Ser Glu Val Lys Met Asp Ala Glu Phe Gly Xaa
1               5                   10                  15

Pro Lys Asp Asp Tyr
            20

<210> SEQ ID NO 176
<211> LENGTH: 21
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (16)..(16)
<223> OTHER INFORMATION: Xaa is episilon-aminocaproic acid

<400> SEQUENCE: 176

Lys Asp Asx Xaa Gly Ser Glu Val Lys Met Asp Asp Glu Phe Gly Xaa
1               5                   10                  15

Pro Lys Asp Asp Tyr
            20

<210> SEQ ID NO 177
<211> LENGTH: 21
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (16)..(16)
<223> OTHER INFORMATION: Xaa is episilon-aminocaproic acid

<400> SEQUENCE: 177

Lys Asp Asx Xaa Gly Ser Glu Val Asn Leu Asp Asp Glu Phe Gly Xaa
1               5                   10                  15

Pro Lys Asp Asp Tyr
            20

<210> SEQ ID NO 178
<211> LENGTH: 23
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
```

```
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa is episilon-aminocaproic acid

<400> SEQUENCE: 178

Lys Asp Asx Xaa Gly Gly Val Val Ile Ala Thr Val Ile Val Ile Thr
 1               5                  10                  15

Gly Xaa Pro Lys Asp Asp Tyr
            20

<210> SEQ ID NO 179
<211> LENGTH: 24
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (19)..(19)
<223> OTHER INFORMATION: Xaa is episilon-aminocaproic acid

<400> SEQUENCE: 179

Lys Asp Asx Xaa Gly Tyr Gly Val Val Ile Ala Thr Val Ile Val Ile
 1               5                  10                  15

Thr Gly Xaa Pro Lys Asp Asp Tyr
            20

<210> SEQ ID NO 180
<211> LENGTH: 18
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (13)..(13)
<223> OTHER INFORMATION: Xaa is episilon-aminocaproic acid

<400> SEQUENCE: 180

Lys Asp Asx Xaa Gly Val Ile Ala Thr Val Ile Gly Xaa Pro Lys Asp
 1               5                  10                  15

Asp Tyr

<210> SEQ ID NO 181
<211> LENGTH: 18
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (13)..(13)
<223> OTHER INFORMATION: Xaa is episilon-aminocaproic acid
```

<400> SEQUENCE: 181

Lys Asp Asx Xaa Asx Tyr Gly Val Val Ile Ala Gly Xaa Pro Lys Asp
1               5                   10                  15

Asp Tyr

<210> SEQ ID NO 182
<211> LENGTH: 15
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(5)
<223> OTHER INFORMATION: Xaa is episilon-aminocaproic acid
<220> FEATURE:
<221> NAME/KEY: misc_feature
<222> LOCATION: (12)..(13)
<223> OTHER INFORMATION: Xaa is episilon-aminocaproic acid

<400> SEQUENCE: 182

Lys Asp Asx Xaa Xaa Gln Gln Leu Leu His Asn Xaa Xaa Pro Lys
1               5                   10                  15

<210> SEQ ID NO 183
<211> LENGTH: 15
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 183

Lys Asp Asx Xaa Gly Gln Gln Leu Leu His Asn Gly Xaa Pro Lys
1               5                   10                  15

<210> SEQ ID NO 184
<211> LENGTH: 13
<212> TYPE: PRT
<213> ORGANISM: Artificial
<220> FEATURE:
<223> OTHER INFORMATION: Synthetic peptide.

<400> SEQUENCE: 184

Lys Asp Asx Gly Gln Gln Leu Leu His Asn Gly Pro Lys
1               5                   10

<210> SEQ ID NO 185
<211> LENGTH: 11
<212> TYPE: PRT
<213> ORGANISM: Artificial
<220> FEATURE:
<223> OTHER INFORMATION: Synthetic peptide.

<400> SEQUENCE: 185

Lys Asp Asx Gln Gln Leu Leu His Asn Pro Lys
1               5                   10

<210> SEQ ID NO 186
<211> LENGTH: 15

```
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(5)
<223> OTHER INFORMATION: Xaa is episilon-aminocaproic acid
<220> FEATURE:
<221> NAME/KEY: misc_feature
<222> LOCATION: (12)..(13)
<223> OTHER INFORMATION: Xaa is episilon-aminocaproic acid

<400> SEQUENCE: 186

Lys Asp Asx Xaa Xaa Ser Ile Gln Tyr Thr Tyr Xaa Xaa Pro Lys
1               5                   10                  15

<210> SEQ ID NO 187
<211> LENGTH: 15
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (13)..(13)
<223> OTHER INFORMATION: Xaa is episilon-aminocaproic acid

<400> SEQUENCE: 187

Lys Asp Asx Xaa Gly Ser Ile Gln Tyr Thr Tyr Gly Xaa Pro Lys
1               5                   10                  15

<210> SEQ ID NO 188
<211> LENGTH: 13
<212> TYPE: PRT
<213> ORGANISM: Artificial
<220> FEATURE:
<223> OTHER INFORMATION: Synthetic peptide.

<400> SEQUENCE: 188

Lys Asp Asx Gly Ser Ile Gln Tyr Thr Tyr Gly Pro Lys
1               5                   10

<210> SEQ ID NO 189
<211> LENGTH: 11
<212> TYPE: PRT
<213> ORGANISM: Artificial
<220> FEATURE:
<223> OTHER INFORMATION: Synthetic peptide.

<400> SEQUENCE: 189

Lys Asp Asx Ser Ile Gln Tyr Thr Tyr Pro Lys
1               5                   10

<210> SEQ ID NO 190
<211> LENGTH: 15
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(5)
<223> OTHER INFORMATION: Xaa is episilon-aminocaproic acid
<220> FEATURE:
<221> NAME/KEY: misc_feature
<222> LOCATION: (12)..(13)
```

<223> OTHER INFORMATION: Xaa is episilon-aminocaproic acid

<400> SEQUENCE: 190

Lys Asp Asx Xaa Xaa Ser Ser Gln Tyr Ser Asn Xaa Xaa Pro Lys
1               5                   10                  15

<210> SEQ ID NO 191
<211> LENGTH: 15
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (13)..(13)
<223> OTHER INFORMATION: Xaa is episilon-aminocaproic acid

<400> SEQUENCE: 191

Lys Asp Asx Xaa Gly Ser Ser Gln Tyr Ser Asn Gly Xaa Pro Lys
1               5                   10                  15

<210> SEQ ID NO 192
<211> LENGTH: 13
<212> TYPE: PRT
<213> ORGANISM: Artificial
<220> FEATURE:
<223> OTHER INFORMATION: Synthetic peptide.

<400> SEQUENCE: 192

Lys Asp Asx Gly Ser Ser Gln Tyr Ser Asn Gly Pro Lys
1               5                   10

<210> SEQ ID NO 193
<211> LENGTH: 11
<212> TYPE: PRT
<213> ORGANISM: Artificial
<220> FEATURE:
<223> OTHER INFORMATION: Synthetic peptide.

<400> SEQUENCE: 193

Lys Asp Asx Ser Ser Gln Tyr Ser Asn Pro Lys
1               5                   10

<210> SEQ ID NO 194
<211> LENGTH: 15
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(5)
<223> OTHER INFORMATION: Xaa is episilon-aminocaproic acid
<220> FEATURE:
<221> NAME/KEY: misc_feature
<222> LOCATION: (12)..(13)
<223> OTHER INFORMATION: Xaa is episilon-aminocaproic acid

<400> SEQUENCE: 194

Lys Asp Asx Xaa Xaa Ser Ser Ile Tyr Ser Gln Xaa Xaa Pro Lys
1               5                   10                  15

<210> SEQ ID NO 195
<211> LENGTH: 15
<212> TYPE: PRT

```
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (13)..(13)
<223> OTHER INFORMATION: Xaa is episilon-aminocaproic acid

<400> SEQUENCE: 195

Lys Asp Asx Xaa Gly Ser Ser Ile Tyr Ser Gln Gly Xaa Pro Lys
1               5                   10                  15

<210> SEQ ID NO 196
<211> LENGTH: 13
<212> TYPE: PRT
<213> ORGANISM: Artificial
<220> FEATURE:
<223> OTHER INFORMATION: Synthetic peptide.

<400> SEQUENCE: 196

Lys Asp Asx Gly Ser Ser Ile Tyr Ser Gln Gly Pro Lys
1               5                   10

<210> SEQ ID NO 197
<211> LENGTH: 11
<212> TYPE: PRT
<213> ORGANISM: Artificial
<220> FEATURE:
<223> OTHER INFORMATION: Synthetic peptide.

<400> SEQUENCE: 197

Lys Asp Asx Ser Ser Ile Tyr Ser Gln Pro Lys
1               5                   10

<210> SEQ ID NO 198
<211> LENGTH: 20
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (16)..(16)
<223> OTHER INFORMATION: Xaa is episilon-aminocaproic acid

<400> SEQUENCE: 198

Lys Asp Pro Xaa Gly Ser Glu Val Asn Leu Asp Ala Glu Phe Gly Xaa
1               5                   10                  15

Pro Lys Gly Tyr
            20

<210> SEQ ID NO 199
<211> LENGTH: 18
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
```

```
<221> NAME/KEY: misc_feature
<222> LOCATION: (14)..(14)
<223> OTHER INFORMATION: Xaa is episilon-aminocaproic acid

<400> SEQUENCE: 199

Lys Asp Pro Xaa Gly Leu Glu His Asp Gly Ile Asn Gly Xaa Pro Lys
1               5                   10                  15

Gly Tyr

<210> SEQ ID NO 200
<211> LENGTH: 18
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 200

Lys Asp Pro Xaa Gly Leu Glu Thr Asp Gly Ile Asn Gly Xaa Pro Lys
1               5                   10                  15

Gly Tyr

<210> SEQ ID NO 201
<211> LENGTH: 18
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (14)..(14)
<223> OTHER INFORMATION: Xaa is episilon-aminocaproic acid

<400> SEQUENCE: 201

Lys Asp Pro Xaa Gly Trp Glu His Asp Gly Ile Asn Gly Xaa Pro Lys
1               5                   10                  15

Gly Tyr

<210> SEQ ID NO 202
<211> LENGTH: 15
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 202

Lys Asp Pro Xaa Gly Tyr Val His Asp Gly Xaa Pro Lys Gly Tyr
1               5                   10                  15
```

```
<210> SEQ ID NO 203
<211> LENGTH: 18
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (14)..(14)
<223> OTHER INFORMATION: Xaa is episilon-aminocaproic acid

<400> SEQUENCE: 203

Lys Asp Pro Xaa Gly Tyr Val His Asp Gly Ile Asn Gly Xaa Pro Lys
1               5                   10                  15

Gly Tyr

<210> SEQ ID NO 204
<211> LENGTH: 18
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 204

Lys Asp Pro Xaa Gly Tyr Val His Asp Ala Pro Val Gly Xaa Pro Lys
1               5                   10                  15

Gly Tyr

<210> SEQ ID NO 205
<211> LENGTH: 16
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa can be any naturally occurring amino acid

<400> SEQUENCE: 205

Lys Asp Pro Xaa Gly Tyr Val His Asp Ala Pro Val Pro Lys Gly Tyr
1               5                   10                  15

<210> SEQ ID NO 206
<211> LENGTH: 16
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (12)..(12)
<223> OTHER INFORMATION: Xaa is episilon-aminocaproic acid

<400> SEQUENCE: 206
```

Lys Asp Pro Tyr Val His Asp Ala Pro Val Gly Xaa Pro Lys Gly Tyr
1               5                   10                  15

<210> SEQ ID NO 207
<211> LENGTH: 14
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid

<400> SEQUENCE: 207

Lys Asp Pro Xaa Gly Tyr Val His Asp Ala Pro Lys Gly Tyr
1               5                   10

<210> SEQ ID NO 208
<211> LENGTH: 16
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (12)..(12)
<223> OTHER INFORMATION: Xaa is episilon-aminocaproic acid

<400> SEQUENCE: 208

Lys Asp Pro Xaa Gly Ile Glu Pro Asp Ser Gly Xaa Pro Lys Gly Tyr
1               5                   10                  15

<210> SEQ ID NO 209
<211> LENGTH: 18
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (14)..(14)
<223> OTHER INFORMATION: Xaa is episilon-aminocaproic acid

<400> SEQUENCE: 209

Lys Asp Pro Xaa Gly Pro Leu Gly Ile Ala Gly Ile Gly Xaa Pro Lys
1               5                   10                  15

Gly Tyr

<210> SEQ ID NO 210
<211> LENGTH: 19
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (15)..(15)

```
<223> OTHER INFORMATION: Xaa is episilon-aminocaproic acid

<400> SEQUENCE: 210

Lys Asp Pro Xaa Gly Ser Gln Asn Tyr Pro Ile Val Gln Gly Xaa Pro
1               5                   10                  15

Lys Gly Tyr

<210> SEQ ID NO 211
<211> LENGTH: 18
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (14)..(14)
<223> OTHER INFORMATION: Xaa is episilon-aminocaproic acid

<400> SEQUENCE: 211

Lys Asp Pro Xaa Gly Glu Asp Val Val Cys Cys Ser Gly Xaa Pro Lys
1               5                   10                  15

Gly Tyr

<210> SEQ ID NO 212
<211> LENGTH: 8
<212> TYPE: PRT
<213> ORGANISM: Artificial
<220> FEATURE:
<223> OTHER INFORMATION: Synthetic peptide

<400> SEQUENCE: 212

Asp Val Val Cys Cys Ser Met Ser
1               5

<210> SEQ ID NO 213
<211> LENGTH: 8
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (7)..(7)
<223> OTHER INFORMATION: Xaa is D form Met

<400> SEQUENCE: 213

Asp Val Val Cys Cys Pro Xaa Ser
1               5

<210> SEQ ID NO 214
<211> LENGTH: 11
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (5)..(5)
<223> OTHER INFORMATION: Xaa is norleucine

<400> SEQUENCE: 214

Asp Ala Ile Pro Xaa Ser Ile Pro Lys Gly Tyr
1               5                   10
```

```
<210> SEQ ID NO 215
<211> LENGTH: 11
<212> TYPE: PRT
<213> ORGANISM: Artificial
<220> FEATURE:
<223> OTHER INFORMATION: Synthetic peptide.  Artificial protease
      stubstrate.

<400> SEQUENCE: 215

Asp Glu Val Asp Gly Ile Asp Pro Lys Gly Tyr
1               5                   10

<210> SEQ ID NO 216
<211> LENGTH: 12
<212> TYPE: PRT
<213> ORGANISM: Artificial
<220> FEATURE:
<223> OTHER INFORMATION: Synthetic peptide.

<400> SEQUENCE: 216

Pro Asp Glu Val Asp Gly Ile Asp Pro Lys Gly Tyr
1               5                   10

<210> SEQ ID NO 217
<211> LENGTH: 12
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (6)..(6)
<223> OTHER INFORMATION: Xaa is norleucine

<400> SEQUENCE: 217

Lys Asp Ala Ile Pro Xaa Ser Ile Pro Lys Gly Tyr
1               5                   10

<210> SEQ ID NO 218
<211> LENGTH: 12
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (6)..(6)
<223> OTHER INFORMATION: Xaa is norleucine

<400> SEQUENCE: 218

Lys Asp Ala Ile Pro Xaa Ser Ile Pro Lys Gly Tyr
1               5                   10

<210> SEQ ID NO 219
<211> LENGTH: 11
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (5)..(5)
<223> OTHER INFORMATION: Xaa is norleucine

<400> SEQUENCE: 219

Asp Ala Ile Pro Xaa Ser Ile Pro Lys Gly Tyr
1               5                   10
```

```
<210> SEQ ID NO 220
<211> LENGTH: 14
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (3)..(3)
<223> OTHER INFORMATION: Xaa is aminoisobutyric acid

<400> SEQUENCE: 220

Lys Asp Xaa Asp Glu Val Asp Gly Ile Asp Pro Lys Gly Tyr
1               5                   10

<210> SEQ ID NO 221
<211> LENGTH: 14
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (3)..(3)
<223> OTHER INFORMATION: Xaa is aminoisobutyric acid

<400> SEQUENCE: 221

Lys Asp Xaa Asp Glu Val Asp Gly Ile Asp Pro Lys Gly Tyr
1               5                   10

<210> SEQ ID NO 222
<211> LENGTH: 14
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (3)..(3)
<223> OTHER INFORMATION: Xaa is aminoisobutyric acid

<400> SEQUENCE: 222

Lys Asp Xaa Asp Glu Val Asn Gly Ile Asp Pro Lys Gly Tyr
1               5                   10

<210> SEQ ID NO 223
<211> LENGTH: 14
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (3)..(3)
<223> OTHER INFORMATION: Xaa is aminoisobutyric acid

<400> SEQUENCE: 223

Lys Asp Xaa Asp Glu Val Asn Gly Ile Asp Pro Lys Gly Tyr
1               5                   10

<210> SEQ ID NO 224
<211> LENGTH: 13
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (3)..(3)
<223> OTHER INFORMATION: Xaa is aminoisobutyric acid
```

```
<400> SEQUENCE: 224

Lys Asp Xaa Glu Val Asp Gly Ile Asp Pro Lys Gly Tyr
1               5                   10

<210> SEQ ID NO 225
<211> LENGTH: 13
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is aminoisobutyric acid

<400> SEQUENCE: 225

Lys Asp Tyr Xaa Ala Asp Gly Ile Asp Pro Lys Gly Tyr
1               5                   10

<210> SEQ ID NO 226
<211> LENGTH: 16
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (3)..(3)
<223> OTHER INFORMATION: Xaa is aminoisobutyric acid

<400> SEQUENCE: 226

Lys Asp Xaa Gly Asp Glu Val Asp Gly Ile Asp Gly Pro Lys Gly Tyr
1               5                   10                  15

<210> SEQ ID NO 227
<211> LENGTH: 18
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (3)..(3)
<223> OTHER INFORMATION: Xaa is aminoisobutyric acid
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (14)..(14)
<223> OTHER INFORMATION: Xaa is episilon-aminocaproic acid

<400> SEQUENCE: 227

Lys Asp Xaa Xaa Gly Asp Glu Val Asp Gly Ile Asp Gly Xaa Pro Lys
1               5                   10                  15

Gly Tyr

<210> SEQ ID NO 228
<211> LENGTH: 18
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (3)..(3)
<223> OTHER INFORMATION: Xaa is aminoisobutyric acid
<220> FEATURE:
<221> NAME/KEY: misc_feature
```

```
<222> LOCATION: (4)..(4)
<223> OTHER INFORMATION: Xaa is episilon-aminocaproic acid
<220> FEATURE:
<221> NAME/KEY: misc_feature
<222> LOCATION: (14)..(14)
<223> OTHER INFORMATION: Xaa is episilon-aminocaproic acid

<400> SEQUENCE: 228

Lys Asp Xaa Xaa Gly Asp Glu Val Asp Gly Ile Asp Gly Xaa Pro Lys
1               5                   10                  15

Gly Tyr

<210> SEQ ID NO 229
<211> LENGTH: 13
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is aminoisobutyric acid

<400> SEQUENCE: 229

Lys Asp Tyr Xaa Ala Asp Gly Ile Asp Pro Lys Gly Tyr
1               5                   10

<210> SEQ ID NO 230
<211> LENGTH: 13
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (3)..(3)
<223> OTHER INFORMATION: Xaa is aminoisobutyric acid

<400> SEQUENCE: 230

Lys Asp Xaa Glu Val Asp Gly Ile Asp Pro Lys Gly Tyr
1               5                   10

<210> SEQ ID NO 231
<211> LENGTH: 12
<212> TYPE: PRT
<213> ORGANISM: Artificial
<220> FEATURE:
<223> OTHER INFORMATION: Synthetic peptide.  Artificial protease
      stubstrate.
<220> FEATURE:
<221> NAME/KEY: misc_feature
<222> LOCATION: (6)..(6)
<223> OTHER INFORMATION: Xaa is norleucine

<400> SEQUENCE: 231

Lys Asp Ala Ile Pro Xaa Ser Ile Pro Lys Gly Tyr
1               5                   10

<210> SEQ ID NO 232
<211> LENGTH: 18
<212> TYPE: PRT
<213> ORGANISM: Artificial
<220> FEATURE:
<223> OTHER INFORMATION: Synthetic peptide.  Artificial protease
      substrate
<220> FEATURE:
<221> NAME/KEY: misc_feature
<222> LOCATION: (3)..(3)
<223> OTHER INFORMATION: Xaa is aminoisobutyric acid
<220> FEATURE:
```

```
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (14)..(14)
<223> OTHER INFORMATION: Xaa is episilon-aminocaproic acid

<400> SEQUENCE: 232

Lys Asp Xaa Xaa Gly Asp Glu Val Asp Gly Ile Asp Gly Xaa Pro Lys
1               5                   10                  15

Gly Tyr

<210> SEQ ID NO 233
<211> LENGTH: 18
<212> TYPE: PRT
<213> ORGANISM: Artificial
<220> FEATURE:
<223> OTHER INFORMATION: Synthetic (chemically synthesized) peptide.
      Artificial protease substrate.
<220> FEATURE:
<221> NAME/KEY: misc_feature
<222> LOCATION: (3)..(3)
<223> OTHER INFORMATION: Xaa is aminoisobutyric acid
<220> FEATURE:
<221> NAME/KEY: misc_feature
<222> LOCATION: (4)..(4)
<223> OTHER INFORMATION: Xaa is episilon-aminocaproic acid
<220> FEATURE:
<221> NAME/KEY: misc_feature
<222> LOCATION: (14)..(14)
<223> OTHER INFORMATION: Xaa is episilon-aminocaproic acid

<400> SEQUENCE: 233

Lys Asp Xaa Xaa Gly Asp Glu Val Asp Gly Ile Asp Gly Xaa Pro Lys
1               5                   10                  15

Gly Tyr

<210> SEQ ID NO 234
<211> LENGTH: 14
<212> TYPE: PRT
<213> ORGANISM: Artificial
<220> FEATURE:
<223> OTHER INFORMATION: Synthetic (chemically synthesized) peptide.
      Artificial protease substrate.
<220> FEATURE:
<221> NAME/KEY: misc_feature
<222> LOCATION: (3)..(3)
<223> OTHER INFORMATION: Xaa is aminoisobutyric acid

<400> SEQUENCE: 234

Lys Asp Xaa Asp Glu Val Asp Gly Ile Asp Pro Lys Gly Tyr
1               5                   10

<210> SEQ ID NO 235
<211> LENGTH: 8
<212> TYPE: PRT
<213> ORGANISM: Artificial
<220> FEATURE:
<223> OTHER INFORMATION: Synthetic (chemically synthesized) peptide.
      Artificial protease substrate.

<400> SEQUENCE: 235

Gly Asp Glu Val Asp Gly Ile Asp
1               5

<210> SEQ ID NO 236
<211> LENGTH: 8
<212> TYPE: PRT
```

```
<213> ORGANISM: Artificial
<220> FEATURE:
<223> OTHER INFORMATION: Synthetic (chemically synthesized) peptide.
      Artificial protease substrate.

<400> SEQUENCE: 236

Gly Asp Glu Val Asp Gly Ile Asp
1               5

<210> SEQ ID NO 237
<211> LENGTH: 4
<212> TYPE: PRT
<213> ORGANISM: Artificial
<220> FEATURE:
<223> OTHER INFORMATION: Synthetic (chemically synthesized) peptide.
      Artificial protease substrate.
<220> FEATURE:
<221> NAME/KEY: misc_feature
<222> LOCATION: (3)..(3)
<223> OTHER INFORMATION: Xaa is alpha-aminoisobutyric acid

<400> SEQUENCE: 237

Lys Asp Xaa Gly
1

<210> SEQ ID NO 238
<211> LENGTH: 5
<212> TYPE: PRT
<213> ORGANISM: Artificial
<220> FEATURE:
<223> OTHER INFORMATION: Synthetic (chemically synthesized) peptide.
      Artificial protease substrate.
<220> FEATURE:
<221> NAME/KEY: misc_feature
<222> LOCATION: (3)..(3)
<223> OTHER INFORMATION: Xaa is alpha-aminoisobutyric acid
<220> FEATURE:
<221> NAME/KEY: misc_feature
<222> LOCATION: (4)..(4)
<223> OTHER INFORMATION: Xaa is episilon amino caproic acid

<400> SEQUENCE: 238

Lys Asp Xaa Xaa Gly
1               5

<210> SEQ ID NO 239
<211> LENGTH: 4
<212> TYPE: PRT
<213> ORGANISM: Artificial
<220> FEATURE:
<223> OTHER INFORMATION: Synthetic (chemically synthesized) peptide.
      Artificial protease substrate.
<220> FEATURE:
<221> NAME/KEY: misc_feature
<222> LOCATION: (2)..(2)
<223> OTHER INFORMATION: Xaa is episilon amino caproic acid

<400> SEQUENCE: 239

Gly Xaa Pro Lys
1

<210> SEQ ID NO 240
<211> LENGTH: 14
<212> TYPE: PRT
<213> ORGANISM: Artificial
<220> FEATURE:
<223> OTHER INFORMATION: Synthetic (chemically synthesized) peptide.
      Artificial protease substrate.
<220> FEATURE:
<221> NAME/KEY: misc_feature
<222> LOCATION: (3)..(3)
```

<223> OTHER INFORMATION: Xaa is aminoisobutyric acid

<400> SEQUENCE: 240

Lys Asp Xaa Asp Glu Val Asp Gly Ile Asp Pro Lys Gly Tyr
1               5                   10

<210> SEQ ID NO 241
<211> LENGTH: 16
<212> TYPE: PRT
<213> ORGANISM: Artificial
<220> FEATURE:
<223> OTHER INFORMATION: Synthetic (chemically synthesized) peptide.
      Artificial protease substrate.
<220> FEATURE:
<221> NAME/KEY: misc_feature
<222> LOCATION: (3)..(3)
<223> OTHER INFORMATION: Xaa is aminoisobutyric acid

<400> SEQUENCE: 241

Lys Asp Xaa Gly Asp Glu Val Asp Gly Ile Asp Gly Pro Lys Gly Tyr
1               5                   10                  15

<210> SEQ ID NO 242
<211> LENGTH: 18
<212> TYPE: PRT
<213> ORGANISM: Artificial
<220> FEATURE:
<223> OTHER INFORMATION: Synthetic peptide.
<220> FEATURE:
<221> NAME/KEY: misc_feature
<222> LOCATION: (4)..(4)
<223> OTHER INFORMATION: Xaa is episilon amino caproic acid
<220> FEATURE:
<221> NAME/KEY: misc_feature
<222> LOCATION: (14)..(14)
<223> OTHER INFORMATION: Xaa is episilon amino caproic acid

<400> SEQUENCE: 242

Lys Asp Asx Xaa Gly Asp Glu Val Asp Gly Ile Asp Gly Xaa Pro Lys
1               5                   10                  15

Gly Tyr

<210> SEQ ID NO 243
<211> LENGTH: 10
<212> TYPE: PRT
<213> ORGANISM: Artificial
<220> FEATURE:
<223> OTHER INFORMATION: Synthetic peptide linker.

<400> SEQUENCE: 243

Asp Gly Ser Gly Gly Gly Glu Asp Glu Lys
1               5                   10

<210> SEQ ID NO 244
<211> LENGTH: 7
<212> TYPE: PRT
<213> ORGANISM: Artificial
<220> FEATURE:
<223> OTHER INFORMATION: Synthetic peptide linker.

<400> SEQUENCE: 244

Lys Glu Asp Gly Gly Asp Lys
1               5

<210> SEQ ID NO 245
<211> LENGTH: 8
<212> TYPE: PRT
<213> ORGANISM: Artificial

-continued

```
<220> FEATURE:
<223> OTHER INFORMATION: Synthetic peptide linker.

<400> SEQUENCE: 245

Asp Gly Ser Gly Glu Asp Glu Lys
1               5

<210> SEQ ID NO 246
<211> LENGTH: 9
<212> TYPE: PRT
<213> ORGANISM: Artificial
<220> FEATURE:
<223> OTHER INFORMATION: Synthetic peptide linker.

<400> SEQUENCE: 246

Lys Glu Asp Glu Gly Ser Gly Asp Lys
1               5
```